US012351656B2

(12) United States Patent
Gravett et al.

(10) Patent No.: US 12,351,656 B2
(45) Date of Patent: *Jul. 8, 2025

(54) FUNCTIONALIZED AND CROSSLINKED POLYMERS

(71) Applicant: PMIDG, LLC, Anderson, SC (US)

(72) Inventors: David Gravett, Mountain View, CA (US); Kara Bethany Acampora, West Union, SC (US); Prabhjot Saini, Greenville, SC (US)

(73) Assignee: PMIDG, LLC, Anderson, SC (US)

( * ) Notice: Subject to any disclaimer, the term of this patent is extended or adjusted under 35 U.S.C. 154(b) by 100 days.

This patent is subject to a terminal disclaimer.

(21) Appl. No.: 17/942,017

(22) Filed: Sep. 9, 2022

(65) Prior Publication Data

US 2023/0312764 A1    Oct. 5, 2023

Related U.S. Application Data

(63) Continuation of application No. 16/643,438, filed as application No. PCT/US2018/049286 on Sep. 1, 2018, now Pat. No. 11,440,976.

(60) Provisional application No. 62/553,371, filed on Sep. 1, 2017.

(51) Int. Cl.

| | |
|---|---|
| *A61L 29/08* | (2006.01) |
| *A61L 27/20* | (2006.01) |
| *A61L 29/16* | (2006.01) |
| *A61L 31/10* | (2006.01) |
| *A61L 31/16* | (2006.01) |
| *C08B 37/08* | (2006.01) |
| *B33Y 70/00* | (2020.01) |
| *B33Y 80/00* | (2015.01) |

(52) U.S. Cl.
CPC .......... *C08B 37/0072* (2013.01); *A61L 27/20* (2013.01); *A61L 29/085* (2013.01); *A61L 31/10* (2013.01); *A61L 29/16* (2013.01); *A61L 31/16* (2013.01); *B33Y 70/00* (2014.12); *B33Y 80/00* (2014.12)

(58) Field of Classification Search
CPC .................................................. C08B 37/0072
See application file for complete search history.

(56) References Cited

U.S. PATENT DOCUMENTS

| 7,166,570 B2 * | 1/2007 | Hunter ............ A61B 17/12186 530/353 |
|---|---|---|
| 2002/0049281 A1 | 4/2002 | Zhao et al. |
| 2006/0089710 A1 | 4/2006 | Ornberg et al. |
| 2016/0193342 A1 | 7/2016 | Gravett et al. |
| 2017/0354758 A1 * | 12/2017 | Deng ...................... A61L 27/20 |

FOREIGN PATENT DOCUMENTS

| CN | 104086788 | 10/2014 |
|---|---|---|
| JP | 2013501091 A | 1/2013 |
| WO | 2012171335 | 12/2012 |
| WO | 2014081594 A | 5/2014 |
| WO | 2019057035 | 3/2019 |

OTHER PUBLICATIONS

Knopf-Marques, H. et al., Advanced Healthcare Materials, "Hyaluronic Acid and Its Derivatives in Coating and Delivery Systems: Applications in Tissue Engineering, Regenerative Medicine and Immunomodulation", 2016, vol. 5, pp. 2841-2855 (Year: 2016).*
Yu, Yu et al., Biomacromolecules, "One-Step "Click" Method for Generating Vinyl Sulfone Groups on Hydroxyl-Containing Water-Soluble Polymers", 2012, vol. 13, pp. 937-942 (Year: 2012).*
International Search Report and Written Opinion dated Jan. 11, 2011, for International Application No. PCT/ US2018/049286.
Yu et al., "One-Step 'Click' Method for Generating Vinyl Sulfone Goups on Hydroxyl-Containing Waler-Soluble Polymers, Biomacromolecules", vol. 13, No. 3, Jan. 9, 2012, pp. 937-942.
Nair et al., "The Thie-Michael Addition Click Reaction: A Powerful and Widely Used Tool in Materials Chemistry", Chemistry of Materials, vol. 26, Aug. 19, 2013, pp. 724-744.
Kong et al. "Long acting hyaluronate-exendin 4 conjugate for the treatment of type 2 diabetes." Biomaterials 31.14 (2010): 4121-4128.
Extended European Search Report issued for Application No. 18849527.9, dated May 19, 2021.
Japanese Office Action issued in JP2020-534807, mailed Dec. 17, 2024. English Translation. 14 pages.

\* cited by examiner

*Primary Examiner* — Bahar Craigo
(74) *Attorney, Agent, or Firm* — Meunier Carlin & Curfman LLC

(57) ABSTRACT

Polyhydric polymers may be converted to derivatives thereof by reaction with divinyl sulfone to provide vinyl sulfone substituted polymers, where the polymers may additionally be further derivatized, including crosslinked, and the crosslinked and non-crosslinked derivatives may be used in biomedical and other applications.

18 Claims, 9 Drawing Sheets

Specification includes a Sequence Listing.

FUNCTIONALIZED AND CROSSLINKED POLYMERS

INCORPORATION BY REFERENCE TO ANY PRIORITY APPLICATIONS

Any and all applications for which a foreign or domestic priority claim is identified in the Application Data Sheet as filed with the present application are hereby incorporated by reference.

INCORPORATION BY REFERENCE OF SEQUENCE LISTING PROVIDED AS AN XML FILE

A Sequence Listing is provided herewith as an XML file entitled "11607-030US2 2023_06_14 Sequence Listing.xml" created Jun. 14, 2023, and having a size of 6,623 bytes. The contents of the XML file are incorporated by reference herein in their entirety.

FIELD OF THE DISCLOSURE

The present disclosure relates generally to functionalized polymers including crosslinked versions thereof, and methods for preparation and uses thereof. The polymers of the present disclosure provide useful properties that are not available from polymers currently available.

BACKGROUND

The use of polymeric materials as biomaterials has grown in recent years, resulting in an expanding polymeric toolbox. Both synthetic and natural polymers have been used as components for biomaterials, and their unique chemical structures can provide specific functions for desired applications. The use of polymers as biomaterials has expanded because of advances in the synthesis of polymers with controlled and functional architectures, which has improved the range of materials possible, as well as their biocompatibility. While these biocompatible polymers are useful because they do not specifically interact with biological systems, this has also hindered their use in applications in which natural physiological interactions are desired to manipulate biological responses such as wound healing, cellular or growth factor binding, or enzymatic degradation. Thus, there is interest in using polymers, such as those found in living organisms, that are modified to provide properties that are improved or different from those of unmodified polymers. An example of such polymers are those comprising polyhydric alcohols. A non-limiting example of such a polymer is hyaluronic acid (HA) polymer.

HA is a non-sulphated glycosaminoglycan (GAG) and is composed of repeating polymeric disaccharides of D-glucuronic acid and N-acetyl-D-glucosamine linked by a glucuronidic β (1→3) bond. In aqueous solutions, HA forms specific stable tertiary structures. Despite the simplicity in its composition, without variations in its sugar composition or without branching points, HA has a variety of physicochemical properties. HA polymers occur in a number of configurations and shapes, depending on their size, salt concentration, pH, and associated cations. Unlike other GAG, in living organisms, HA is not covalently attached to a protein core, but it may form aggregates with proteoglycans. HA encompasses a large volume of water giving solutions high viscosity, even at low concentrations.

HA is involved in multiple physiological processes, for example, skin. A key molecule involved in skin moisture is hyaluronan or hyaluronic acid (HA), a glycosaminoglycan (GAG) with a unique capacity to bind and retain water molecules. HA belongs to the extracellular matrix (ECM) molecules. ECM molecules that lie between cells, in addition to providing a constructive framework, exert major effects on cellular function. These ECM molecules, although they appear amorphous by light microscopy, they form a highly organized structure, comprising mainly of GAG, proteoglycans, growth factors and structural proteins such as collagens, with the predominant component of the skin ECM is HA.

What is needed are derivatives of polyhydric polymers, compositions of such polymers and use of such polymers for medical treatments and production of medical devices and components.

SUMMARY

In brief, the present disclosure provides polymers, method of making polymers, and methods of using polymers.

1) For example, in one aspect, the present disclosure provides a derivative of a polyhydric polymer, such as a polysaccharide, e.g., polyhyaluronic acid, in which one or more hydroxyl groups of the hyaluronic acid is a modified hydroxyl group, wherein the derivative of hyaluronic acid or other polyhydric polymer has the structure HA-$(OCH_2CH_2SO_2CH_2CH_2—X—R_1—Y)_n$ where HA is a polyhydric polymer such as hyaluronic acid, X is S or NH, $R_1$ is a substituted or unsubstituted $C_1$-$C_{20}$ aliphatic or aromatic moiety and n is the number of modified hydroxyl groups where n is an integer and n≥1, and Y is one or more of H, a carboxylic acid group or a salt or ester thereof, a hydroxyl group, a sulfonic acid group or a salt thereof, or an amine group.

In another aspect, the present disclosure provides a derivative of a polyhydric polymer, such as a polysaccharide, e.g., hyaluronic acid, in which two or more hydroxyl groups of the hyaluronic acid are modified hydroxyl groups, wherein the derivative of hyaluronic acid or other polyhydric polymer has the structure $(Y—R_2—X—CH_2CH_2SO_2CH_2CH_2O)_m$-HA-$(OCH_2CH_2SO_2CH_2CH_2—X—R_1—Y)_n$ where HA is hyaluronic acid or other polyhydric polymer, X is S or NH, $R_1$ is a substituted or unsubstituted $C_1$-$C_{20}$ aliphatic or aromatic moiety, $R_2$ is a substituted or unsubstituted $C_1$-$C_{20}$ aliphatic or aromatic moiety wherein $R_1$ and $R_2$ are different from each other, wherein n and m are each integers, and n≥1 and m≥1, and Y is H; a carboxylic acid group, or a salt or ester; thereof; a hydroxyl group; a sulfonic acid group, or a salt thereof, or an amine group.

In another aspect, the present disclosure provides a derivative of polyhydric polymer, such as a polysaccharide, e.g., hyaluronic acid, in which two or more hydroxyl groups of the hyaluronic acid are modified hydroxyl groups, wherein the derivative of hyaluronic acid has the structure $(CH_2=CH—SO_2CH_2CH_2O)m$-HA-$(OCH_2CH_2SO_2CH_2CH_2—X—R_1—Y)_n$ where HA is hyaluronic acid or other polyhydric polymer, X is S or NH, $R_1$ is a substituted or unsubstituted $C_1$-$C_{20}$ aliphatic or aromatic moiety, each of n and m is an integer, and n≥1 and m≥1, and Y is H; a carboxylic acid group, or a salt or ester; thereof; a hydroxyl group; a sulfonic acid group, or a salt thereof; or an amine group.

In further aspects, the present disclosure provides derivatives of polyhydric polymers such as described above, which are further characterized by wherein 0.25-50% of a sum of the hydroxyl groups and the modified hydroxyl groups are a modified hydroxyl group.

In another aspect, the present disclosure comprises crosslinked polymers comprising a reaction product of a derivative of a polyhydric polymer disclosed herein, such as a polysaccharide, e.g., hyaluronic acid, and optionally, may comprise a crosslinking agent, wherein as used herein, a crosslinking agent may comprise known crosslinking agents, such as crosslinking compounds, for example, OH crosslinking agents or vinyl crosslinking agents, $FeCl_3$, or compounds and/or energy sources, including but not limited to, UV and related photoinitiator compounds.

In an aspect, the present disclosure comprises crosslinked polymers comprising a reaction product of a derivative of a polyhydric polymer disclosed herein, such as a polysaccharide, e.g., hyaluronic acid, and optionally, may comprise a crosslinking agent, wherein
   a) the derivative of the polyhydric polymer, such as hyaluronic acid has the structure HA-$(OCH_2CH_2SO_2CH_2CH_2-X-R_1-Y)_n$ wherein one or more hydroxyl groups of the hyaluronic acid is a modified hydroxyl group, and wherein HA is the polyhydric polymer, e.g., hyaluronic acid, comprising hydroxyl groups, X is S or NH, $R^1$ is a substituted or unsubstituted $C_1$-$C_{20}$ aliphatic or aromatic moiety and n is the number of modified hydroxyl groups where $n\geq 1$, and Y is H; a carboxylic acid group, or a salt or ester; thereof; a hydroxyl group; a sulfonic acid group, or a salt thereof; or an amine group; and
   b) the crosslinking agent comprises at least two functional groups that are capable of reacting with the hydroxyl groups of the derivative of hyaluronic acid.

In another aspect, the present disclosure provides a crosslinked polymer comprising a reaction product of a derivative of a polyhydric polymer disclosed herein, such as a polysaccharide, e.g., hyaluronic acid, and a crosslinking agent, wherein
   a) the derivative of a polyhydric polymer, comprises two or more hydroxyl groups of the hyaluronic acid as modified hydroxyl groups, wherein the derivative of hyaluronic acid or other polyhydric polymer has the structure $(Y-R_2-X-CH_2CH_2SO_2CH_2CH_2O)_m$-HA-$(OCH_2CH_2SO_2CH_2CH_2-X-R_1-Y)_n$ where HA is hyaluronic acid or other polyhydric polymer, X is S or NH, $R_1$ is a substituted or unsubstituted $C_1$-$C_{20}$ aliphatic or aromatic moiety, $R_2$ is a substituted or unsubstituted $C_1$-$C_{20}$ aliphatic or aromatic moiety wherein $R_1$ and $R_2$ are different from each other, wherein n and m are each integers, and $n\geq 1$ and $m\geq 1$, and Y is H; a carboxylic acid group, or a salt or ester; thereof; a hydroxyl group; a sulfonic acid group, or a salt thereof; or an amine group; and
   b) the crosslinking agent comprises at least two functional groups that are capable of reacting with the hydroxyl groups of the derivative of hyaluronic acid.

In another aspect, the present disclosure provides crosslinked polymers comprising a reaction product of a derivative of a polyhydric polymer, such as a polysaccharide, e.g., hyaluronic acid, disclosed herein, and a crosslinking agent, wherein
   a) the derivative of hyaluronic acid comprises vinyl groups and has the structure $(CH_2=CH-SO_2CH_2CH_2O)_m$-HA-$(OCH_2CH_2SO_2CH_2CH_2-X-R_1-Y)_n$ wherein two or more hydroxyl groups of the hyaluronic acid are modified hydroxyl groups, HA is hyaluronic acid comprising hydroxyl groups, X is S or NH, $R^1$ is a substituted or unsubstituted $C_1$-$C_{20}$ aliphatic or aromatic moiety, $n\geq 1$ and $m\geq 1$, and Y is H; a carboxylic acid group, or a salt or ester; thereof; a hydroxyl group; a sulfonic acid group, or a salt thereof; or an amine group; and
   b) the crosslinking agent comprises at least two functional groups that are capable of reacting with the vinyl groups of the derivative of hyaluronic acid or
   c) the crosslinking agent comprises at least two functional groups that are capable of reacting with the hydroxyl groups of the derivative of hyaluronic acid or
   d) The crosslinking agent comprises functional groups that are capable of ionic crosslinking or
   e) the crosslinking agent comprises functional groups that are capable of thermal crosslinking or
   f) the crosslinking agent generates free radicals that are capable of free radical crosslinking In further aspects, a crosslinked polymer disclosed herein may be further characterized by wherein 0.25-50% of a sum of the hydroxyl groups and the modified hydroxyl groups are a modified hydroxyl group.

In another aspect, the present disclosure provides a process comprising:
   a) reacting hydroxyl groups attached to a polymer, such as hydroxyl groups on hyaluronic acid (HA) or other polyhydric polymer, with divinyl sulfone (DVS) to provide a first derivative of the polymer; and
   b) reacting the first derivative of the polymer with a nucleophile of a formula selected from X'—$R^1$—Y and X'—$R^2$—Y to provide a second derivative of the polymer;
   wherein $R^1$ is a substituted or unsubstituted $C_1$-$C_{20}$ aliphatic or aromatic moiety, $R_2$ is a substituted or unsubstituted $C_1$-$C_{20}$ aliphatic or aromatic moiety, X' is a nucleophilic group, comprising a thiol or amine, and Y is one or more of H, a carboxylic acid group or a salt or ester thereof, a hydroxyl group, a sulfonic acid group or a salt thereof, or an amine group. A polymer that has undergone one or more derivatization reactions includes, and is referred to herein as, a derivative of a polyhydric polymer, whether the polymer has been derivatized one or more times, e.g., one, two, three, four, etc. derivatizations of the initial polymer. A derivative of a polymer may also be referred to as a first derivative, a second derivative, a third derivative, etc., of a polymer.

In further aspects, the process may be further characterized by one or more of the following:
1) The process wherein 0.25-50% of the hydroxyl groups present on the initial (underivatized) polymer are converted to oxyethyl ethenyl sulfone groups of the formula —$OCH_2CH_2$—$SO_2CH=CH_2$.
2) The process wherein the polymer is hyaluronic acid and the first derivative of the polymer is an oxyethyl ethenyl sulfone derivative of the hyaluronic acid is HA-$(-OCH_2CH_2SO_2CH=CH_2)_n$(HA-DVS).
3) The process wherein the second derivative is HA-$(OCH_2CH_2SO_2CH_2CH_2-X-R_1)_n$ (HA-DVS-N).
4) The process wherein 0.25-50% of the hydroxyl groups present on the polymer are converted to —$OCH_2CH_2SO_2CH_2CH_2-X-R_1$ groups.
5) The process wherein X' is thiol or amine and X is —S— or —NH—.
6) The process wherein the second derivative is HA-$(-OCH_2CH_2SO_2CH_2CH_2-X-R^2-Y)_n$ (HA-DVS-NY).

7) The process of wherein 0.25-50% of the hydroxyl groups present on the polymer are converted to —OCH$_2$CH$_2$SO$_2$CH$_2$CH$_2$—X—R$^2$—Y groups as calculated by the sum of the hydroxyl groups and the modified hydroxyl groups.

8) The process wherein X is —S—.

9) The process wherein Y is hydroxyl.

10) The process wherein Y is carboxylic acid or a salt or ester thereof.

11) The process wherein Y is sulfonic acid of a salt of ester thereof.

12) The process further comprising reacting the second derivative of the polymer with a crosslinking agent to provide a third derivative of the polymer, where the third derivative is a crosslinked polymer.

In another aspect, the present disclosure provides a derivative of a polyhydric polymer, such as a derivative of hyaluronic acid, prepared by any of the processes identified herein. In another aspect, the present disclosure provides a crosslinked polymer prepared by any of the processes identified herein.

In another aspect, the present disclosure provides a composition comprising a derivative of a polymeric polyhydric alcohol, e.g., hyaluronic acid, wherein derivatives of a polymeric polyhydric alcohol may comprise the derivatives as disclosed above for polyhydric polymers. For example, HA-(OCH$_2$CH$_2$SO$_2$CH$_2$CH$_2$—X—R$_1$—Y)$_n$; (Y—R$_2$—X—CH$_2$CH$_2$SO$_2$CH$_2$CH$_2$O)$_m$—HA-(OCH$_2$CH$_2$SO$_2$CH$_2$CH$_2$—X—R$_1$—Y)$_n$; (CH$_2$=CH—SO$_2$CH$_2$CH$_2$O)$_m$—HA-(OCH$_2$CH$_2$SO$_2$CH$_2$CH$_2$—X—R$^1$—Y)$_n$; or (CH$_2$=CH—SO$_2$CH$_2$CH$_2$O)$_m$—HA, where HA is hyaluronic acid or other polyhydric polymer, X is S or NH, R$_1$ is a substituted or unsubstituted C$_1$-C$_{20}$ aliphatic or aromatic moiety, R$_2$ is a substituted or unsubstituted C$_1$-C$_{20}$ aliphatic or aromatic moiety, and where applicable, wherein R$_1$ and R$_2$ are different from each other, Y is one or more of H, a carboxylic acid group or a salt or ester thereof, a hydroxyl group, a sulfonic acid group or a salt thereof, or an amine group; wherein n and m are each integers, and n≥1 and m≥1 A composition may further comprise an excipient.

In another aspect, the present disclosure provides a composition comprising a crosslinked polymer, e.g., a crosslinked derivative of polymeric hyaluronic acid, as described herein. A composition may further comprise an excipient. Each of the compositions disclosed herein may optionally include one or more of a pharmaceutically acceptable synthetic polymer, thermosreversible polymer, biodegradable polymer, buffer, complexing agent, tonicity modulator, ionic strength modifier, solvent, anti-oxidant, preservative, viscosity modifier, pH modifier, surfactant, emulsifier, phospholipid, stabilizer and porogen. Also optionally, a composition as disclosed herein may further comprise a biologically active agent.

Derivatized polymers and compositions comprising one or more derivatized polymers disclosed herein exhibit shear thinning. Shear thinning is the non-Newtonioan behavior of fluids whose viscosity decreases under shear strain.

In additional aspects, the present disclosure provides method of using the polymers and compositions as disclosed herein. For example, the present disclosure provides the following aspects:

1) A wound healing device comprising a composition as described herein.

2) A method for wound healing comprising administering to a subject in need thereof an effective amount of a composition as described herein.

3) A bulking agent comprising a composition as described herein.

4) A dermal filler comprising a composition as described herein.

5) A method of filling a void in a subject in need thereof comprising administering to the subject a dermal filler as described herein.

6) A viscosupplement comprising a composition as described herein.

7) A method of relieving joint pain in a subject in need thereof, comprising administering to the subject a viscosupplement as described herein.

8) A method of preventing surgical adhesions in a subject in need thereof comprising administering the subject an effective amount of a composition as described herein.

9) A tissue sealant comprising a composition as described herein.

10) A method of sealing tissue in a subject in need thereof comprising administering to the subject an effective amount of a tissue sealant as described herein.

11) A method of treating bacterial vaginosis in a subject in need thereof comprising administering to the subject an effective amount of a composition as described herein.

12) A nasal treatment device comprising a composition as described herein.

13) A method of treating a nasal condition in a subject in need thereof comprising administering the subject an effective amount of a composition as described herein.

14) An eye drop comprising a composition as described herein.

15) A method of treating an ocular condition in a subject in need thereof comprising administering the subject an effective amount of a composition as described herein.

16) A punctal plug comprising a composition as described herein.

17) A method of treating mucocitis in a subject in need thereof comprising administering to the subject an effective amount of a composition as described herein.

18) An anti-bacterial formulation comprising a composition as described herein.

19) An ear treatment device comprising a composition as described herein.

20) A method of treating an ear condition comprising administering to a subject in need thereof an effective amount of a composition as described herein.

21) A method of drug delivery to a subject in need thereof comprising administering to the subject an effective amount of a composition as described herein that comprises the drug.

22) A biopsy plug comprising a composition as described herein.

23) A plug for female sterilization comprising a composition as described herein.

24) A method of female sterilization to a subject in need thereof comprising administering to the subject an effective amount of a composition as described herein.

25) A tissue scaffold comprising a composition as described herein.

26) The method of supporting tissue growth in a subject in need thereof comprising implanting in the subject a tissue scaffold as described herein.

27) A burr hole plug comprising a composition as described herein.

28) A nerve guide comprising a composition as described herein.

29) A vaginal lubricant comprising a composition as described herein.
30) A coating for a device comprising a composition as described herein.
31) A method for coating a device comprising applying a coating as described herein onto a surface of the device.
32) A method of administering an injectable formulation comprising a composition as described herein.
33) A method for additive manufacturing comprising a polymer as described herein, e.g., a derivative of hyaluronic acid as described herein, or prepared by a process as described herein, to provide a derivative of the polymer, e.g., hyaluronic acid, and depositing the derivative onto a substrate to provide an article formed by additive manufacturing.
34) A method for additive manufacturing by deposition of a with a polymer as described herein, e.g., a derivative of hyaluronic acid as described herein on the surface or within a polymeric substrate.
35) A method of coating or penetrating an article formed by additive manufacturing with a polymer as described herein, e.g., a derivative of hyaluronic acid as described herein.
36) An electrospun material or article comprising a composition as described herein.
37) A method for producing an electrospun material or article, comprising producing, with an electrospinning device, a material or an article comprising a derivative of hyaluronic acid described herein.
38) A method of coating or penetrating an article formed by electrospinning with a polymer as described herein, e.g., a derivative of hyaluronic acid as described herein.
39) A textile material or article comprising a composition as described herein.
40) A method for producing a textile material or article, comprising producing, with an electrospinning device, a material or an article comprising a derivative of hyaluronic acid described herein.
41) A method of coating or penetrating an article formed by electrospinning on a textile substrate with a polymer as described herein, e.g., a derivative of hyaluronic acid as described herein.

The above-mentioned additional features of the present disclosure and the manner of obtaining them will become apparent, and the disclosure will be best understood by reference to the following more detailed description. All references disclosed herein are hereby incorporated by reference in their entirety as if each was incorporated individually.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more aspects are set forth in the description below. The features illustrated or described in connection with one exemplary aspect may be combined with the features of other aspects. Thus, any of the various aspects described herein can be combined to provide further aspects. Aspects of the aspects can be modified, if necessary to employ concepts of the various patents, applications and publications as identified herein to provide yet further aspects. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various aspects. Non-limiting and non-exhaustive aspects are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more aspects are described hereinafter with reference to the accompanying drawings in which.

DETAILED DESCRIPTION OF THE DISCLOSURE

Figure 1:
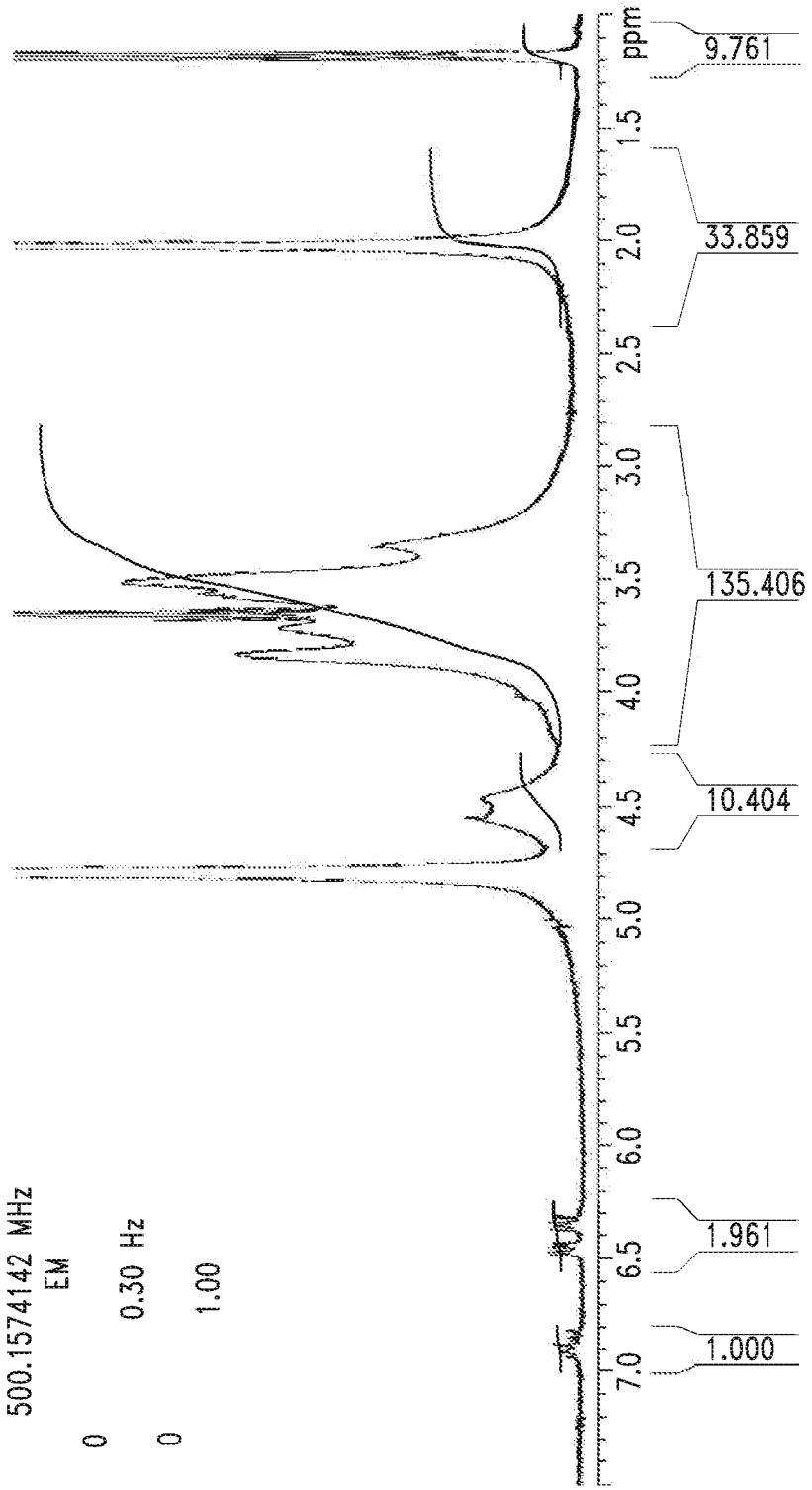
FIG. 1 shows a $^1$H NMR spectrum of a divinyl sulfone-modified hyaluronic acid according to the present disclosure.

The present disclosure may be understood more readily by reference to the following detailed description of preferred aspects of the disclosure and the Examples included herein.

In one aspect, the present disclosure provides functionalized polymers including crosslinking versions thereof. A functionalized polymer refers to an organic polymer comprising hydroxyl groups, and optionally also including a second functional group, such as a carboxylic acid, amine or sulfonic acid group.

The present disclosure provides a derivative of a polyhydric polymer, such as a polysaccharide, e.g., hyaluronic acid, in which one or more hydroxyl groups of the hyaluronic acid is a modified hydroxyl group, wherein the derivative of hyaluronic acid or other polyhydric polymer has the structure HA-(OCH$_2$CH$_2$SO$_2$CH$_2$CH$_2$—X—R$_1$—Y)$_n$ where HA is a polyhydric polymer such as hyaluronic acid, X is S or NH, R$_1$ is a substituted or unsubstituted C$_1$-C$_{20}$ aliphatic or aromatic moiety and n is the number of modified hydroxyl groups where n is an integer and n≥1, and Y is one or more of H, a carboxylic acid group or a salt or ester thereof, a hydroxyl group, a sulfonic acid group or a salt thereof, a phosphonic acid group or a salt thereof, or an amine group.

In another aspect, the present disclosure provides a derivative of a polyhydric polymer, such as a polysaccharide, e.g., hyaluronic acid, in which two or more hydroxyl groups of the hyaluronic acid are modified hydroxyl groups, wherein the derivative of hyaluronic acid or other polyhydric polymer has the structure (Y—R$_2$—X—CH$_2$CH$_2$SO$_2$CH$_2$CH$_2$O)$_m$—HA-(OCH$_2$CH$_2$SO$_2$CH$_2$CH$_2$—X—R$_1$—Y)$_n$ where HA is hyaluronic acid or other polyhydric polymer, X is S or NH, R$_1$ is a substituted or unsubstituted C$_1$-C$_{20}$ aliphatic or aromatic moiety, R$_2$ is a substituted or unsubstituted C$_1$-C$_{20}$ aliphatic or aromatic moiety wherein R$_1$ and R$_2$ are different from each other, wherein n and m are each integers, and n≥1 and m≥1, and Y is H; a carboxylic acid group, or a salt or ester; thereof; a hydroxyl group; a sulfonic acid group or a salt thereof; a phosphonic acid group or a salt thereof; or an amine group.

In another aspect, the present disclosure provides a derivative of polyhydric polymer, such as a polysaccharide, e.g., hyaluronic acid, in which two or more hydroxyl groups of the hyaluronic acid are modified hydroxyl groups, wherein the derivative of hyaluronic acid has the structure (CH$_2$=CH—SO$_2$CH$_2$CH$_2$O)m-HA-(OCH$_2$CH$_2$SO$_2$CH$_2$CH$_2$—X—R$_1$—Y)$_n$ where HA is hyaluronic acid or other polyhydric polymer, X is S or NH, R$_1$ is a substituted or unsubstituted C$_1$-C$_{20}$ aliphatic or aromatic moiety, each of n and m is an integer, and n≥1 and m≥1, and Y is H; a carboxylic acid group, or a salt or ester; thereof; a hydroxyl group; a sulfonic acid group, or a salt thereof; a phosphonic acid group or a salt thereof; or an amine group.

In further aspects, the present disclosure provides derivatives of polyhydric polymers such as described above, which are further characterized by the derivative wherein 0.25-50% of a sum of the hydroxyl groups and the modified hydroxyl groups are a modified hydroxyl group.

In another aspect, the present disclosure comprises crosslinked polymers comprising a reaction product of a derivative of a polyhydric polymer disclosed herein, such as a polysaccharide, e.g., hyaluronic acid, and optionally, may comprise a crosslinking agent, wherein as used herein, a crosslinking agent may comprise known crosslinking agents, such as crosslinking compounds, for example, OH crosslinking agents or vinyl crosslinking agents, FeCl$_3$, or compounds and/or energy sources, including but not limited to, UV and related photoinitiator compounds.

In one aspect the present disclosure utilizes a polysaccharide with one or more available hydroxyl groups and reacts one or more of those hydroxyl groups under specific conditions as disclosed herein with divinyl sulfone such that only one of the vinyl groups of the divinyl sulfone reacts with the hydroxyl group via an addition reaction to form an ether bond between the polysaccharide and the residue of the divinyl sulfone. The degree of reaction can range from about 0.5% to about 50% of the available hydroxyl groups. At higher substitution, i.e., around 50%, some degree of crosslinking will typically occur. Thus, the present disclosure provides vinyl sulfone substituted polysaccharide polymers with minimal to no crosslinking, or polysaccharide polymers that have a level of vinyl sulfone substitution crosslinking due to double reaction of the divinyl sulfone (i.e., reaction of both ethenyl groups of the DVS with hydroxyl groups).

The residual vinyl group of the vinyl sulfone can be then reacted with a compound that has a reactive thiol group. This reaction occurs via a Michael addition between the residual vinyl group of the divinyl sulfone and the free thiol group such that a thioether bond is formed. There are numerous variations of the degree of substitution, the thiol derivative used, the sequence of the reactions and the replication of reactions that provide a large variety of derivatives of polymeric polyhydric alcohols and compositions contemplated and disclosed herein. Derivatives of polymeric polyhydric alcohols can be crosslinked in many different ways, and compositions comprising such crosslinked derivatives of polymeric polyhydric alcohols are contemplated and disclosed herein. The derivatives of polymeric polyhydric alcohols and compositions thereof have numerous medical and non-medical applications. Methods of use or treatment disclosed herein may comprise derivatives of polymeric polyhydric alcohols and compositions thereof. Derivatives of polymeric polyhydric alcohols may also be referred to herein as polyhydric polymer derivatives.

The derivatives of polymeric polyhydric alcohols and compositions thereof of the present disclosure are prepared as described herein. Typically, a polymer having hydroxyl groups is combined with divinyl sulfone (DVS) under suitable reaction conditions. Those reaction conditions include a suitable pH of the solution, where the reaction typically occurs under basic conditions, e.g., a pH of 11-14, or 12-13, e.g., about 12.3. The reaction conditions include a suitable solvent, where water or DMSO are suitable solvents, e.g., the reaction may be conducted in water. The description of reaction conditions may further include stirring the reacting mixture, e.g., stirring with a stirring rate of >200 rpm (rotations per minute), such as 250-800 rpm. Furthermore, the description of reaction conditions may include specification of the relative amounts of DVS and polymer (e.g., polysaccharide) that are combined, where these relative amounts may be expressed in terms of moles of DVS to moles of repeat unit in the polymer. For instance, the method for preparing the functionalized polymer may be described in terms of the ratio of DVS:polymer repeat unit, where this ratio may be at least 0.5:1, e.g., up to about 5:1, or up to about 7.5:1, or up to about 10:1, or up to about 15:1, or up to about 20:1

An exemplary functionalized polymer is a polysaccharide, where an exemplary polysaccharide is hyaluronic acid (HA). HA is a polysaccharide illustrated by the structure shown below.

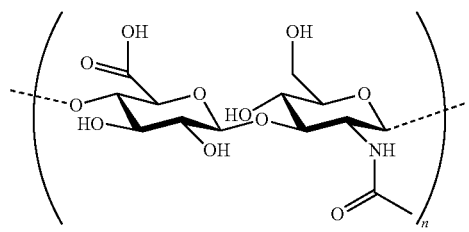

HA contains two different functional groups, namely hydroxyl groups and carboxylic acid groups. HA also contains ether and acetamide groups, however these are essentially chemically inert. In commercially available preparations of HA, some or all of the carboxylic acids may be present as the corresponding salt, e.g., as the sodium, potassium or ammonium salt. In the present disclosure, and unless the context indicates otherwise, HA refers inclusively to polymers of the structure shown above as well as the corresponding carboxylate salts of those polymers. Another exemplary polysaccharide polymer is dextran. Other exemplary polysaccharide polymers useful in the present disclosure include, but are not limited to, sodium alginate, calcium alginate, dextran, carboxymethyl cellulose, hydroxypropyl cellulose, hydroxypropyl methylcellulose, methyl cellulose, hyaluronic acid, hyaluronic acid derivatives, dextran, heparin, chitosan, xantham gum, Xylan, guar gum, pullulan or locust bean gum. The term "polyhydric polymer" includes, but is not limited to, such polymeric polysaccharides. The term "polyhydric polymer" includes, but is not limited to polymers that have two or more hydroxyl groups, and may also be referred to herein as polymeric polyhydric alcohols In one aspect, the present disclosure provides a process wherein a polymeric polysaccharide that has an available hydroxyl group, i.e., a hydroxyl group that is capable of undergoing a reaction with divinyl sulfone, is reacted with DVS under basic conditions. If the conditions are selected appropriately, the reaction can be controlled such that one of the vinyl groups of the divinyl sulfone will react with a free hydroxyl group of the polysaccharide such that the polysaccharide does not crosslink to such an extent that it forms a hydrogel. This results in the polysaccharide being functionalized with the divinyl sulfone such that one of the vinyl groups undergoes reaction with a hydroxyl group of the polysaccharide and the other vinyl group remains functional. The vinyl group of the divinyl sulfone reacts with the hydroxyl group by an addition reaction that results in an ether linkage.

The reaction may be performed under basic conditions with a pH of greater than 11. Optionally, the pH is in the range of 12.0 to 13.5. Optionally, the pH is in the range is in the 12.0 to 12.5 range. Optionally, the pH range is in the 12.2 to 12.7 range.

To ensure that the predominant reaction is a single reaction of one of the vinyl groups of the divinyl sulfone, and not a crosslinking reaction in which predominantly both the vinyl groups react with hydroxyl groups of the polysaccharide to form a crosslinked gel, the molar ratio of the divinyl sulfone to that of the polysaccharide repeat units is greater than 1. In one aspect, the molar ratio of the divinyl sulfone to that of the polysaccharide repeat units is greater than 5. In one aspect, the molar ratio of the divinyl sulfone to that of the polysaccharide repeat units is greater than 7. In one aspect, the molar ratio of the divinyl sulfone to that of the polysaccharide repeat units is greater than 10. In one aspect, the molar ratio of the divinyl sulfone to that of the polysaccharide repeat units is greater than 15. In an aspect, the molar ratio of the divinyl sulfone to that of the polysaccharide repeat units is from about 1 to about 20, or from about 1 to about 15, or from about 1 to about 10, or from about 1 to about 5, or from about 5 to about 20, or from about 5 to about 15, or from about 5 to about 10, of from about 10 to about 20, or from about 10 to 15, or is about 1, 2, 3, 4, 5, 6, 7, 8, 9, 10, 11, 12, 13, 14, 15, 16, 17, 18, 19 or 20.

To provide intimate contact between the reactants, the reaction mixture may be stirred. Methods and devices for adequate mixing are known to those of skill in the art. For example, in order to ensure that there is adequate stirring of the reaction solution during the reaction, the rotational speed of the mixing impellor should be controlled. In one aspect, the revolutions per minute (rpm) of the mixing impellor should be in the range of 200 to 400 rpm. In another aspect, the revolutions per minute (rpm) of the mixing impellor should be in the range of 400 to 600 rpm. In another aspect, the revolutions per minute (rpm) of the mixing impellor should be in the range of 600 to 800 rpm.

The amount of substitution accomplished may be controlled, in part, by the duration of exposure of the polysaccharide to the divinyl sulfone at a pH of greater than 11 (reaction time). In one aspect, the reaction time can range from ≥10 seconds through to 60 minutes. In one aspect, the reaction time can be in the range of 2 minutes to 35 minutes. In another aspect, the reaction time can be in the range of 4 minutes to 30 minutes, or from 20 minutes to 60 minutes, from ≥15 minutes to 20 minutes, from 5 minutes to 10 minutes, from ≥10 seconds to 30 seconds, from 30 second to 1.5 minutes, and ranges thereinbetween The solvent that can be used for the reaction can be water, water with an ionic modifier, for example NaCl, a combination of water and a water-miscible solvent. Water miscible solvents can include but are not limited to methanol, ethanol, isopropanol, dimethyl formamide (DMF), acetone, 1,4-dioxane, pyridine, dimethyl sulfoxide (DMSO), tetrahydrofuran (THF) and acetonitrile.

The temperature of the reaction mixture can also be used to influence the amount of substitution of the polysaccharide by the divinyl sulfone. In one aspect, the reaction mixture can be maintained at a temperature that is lower than 25° C. so as to reduce the rate of the reaction. This can enable lower substitution levels for the same duration as compared to room temperature or it can allow for a longer reaction time that that at room temperature to yield a similar amount of substitution. In one aspect, the temperature can be in the 15° C. to 20° C. range. In another aspect, the reaction mixture can be in the 10° C. to 15° C. range. In yet another aspect, the temperature can be in the 2° C. to 10° C. range. In another aspect, the temperature can be increase above 25° C. so as to provide shorter reaction times as compared to 25° C. to get similar amounts of substitution or to get greater substitution as compared to 25° C. for an equivalent amount of reaction time. In one aspect, the reaction mixture can be in the 28° C. to 35° C. range. In another aspect, the reaction mixture can be in the 36° C. to 50° C. range. In another aspect, the reaction mixture can be in the 51° C. to 75° C. range.

The amount of substitution, as measured by the molar ratio of the attached vinyl group from the divinyl sulfone to the polysaccharide repeat unit, can be greater than 5%. In one aspect, for polysaccharides with at least one hydroxyl group, the amount of substitution is in the range of 5% to 35%. In another aspect, for polysaccharides with at least one hydroxyl group, the amount of substitution is in the range of 36% to 70% range. In another aspect, for polysaccharides with at least one hydroxyl group, the amount of substitution is in the range of 71% to 100% range. In another aspect, for polysaccharides with at least two hydroxyl groups, the amount of substitution is in the range of 101% to 200% range.

In one aspect, polysaccharide polymers that comprise at least one hydroxyl group that is available for reaction with divinyl sulfone under conditions where the pH is greater than 11 are suitable for use in this disclosure. Such polysaccharides include, but are not limited to hyaluronic acid and its sodium or potassium salts, hyaluronic acid derivatives, dextran and dextran derivatives, dextran sulfate, heparin, chitosan and derivatives thereof, xylan, guar gum, locust bean gum, chondroitin 6-sulfate, chondroitin 4-sulfate, heparan sulfate, keratin sulfate, dermatan sulfate and chitin. In an aspect, the polysaccharide polymer is hyaluronic acid or sodium hyaluronate. In another aspect, the polysaccharide is dextran. As used herein, polysaccharide means polymeric polysaccharide molecules.

The molecular weight of the polysaccharide can be selected. Molecular weights from ≥10,000 to 5,000,000 may be used. In one aspect, the polysaccharide has a molecular weight of over 10,000. In another aspect, the polysaccharide has a molecular weight in the range of 10,000 to 50,000. In another aspect, the polysaccharide has a molecular weight in the range of 50,000 to 200,000. In another aspect, the polysaccharide has a molecular weight in the range of 200,000 to 600,000. In an aspect, the polysaccharide has a molecular weight in the range of 600,000 to 1,000,000. In an aspect, the polysaccharide has a molecular weight in the range of 1,000,000 to 2,500,000. In yet another aspect, the polysaccharide has a molecular weight in the range of 2,500,000 to 5,000,000. The molecular weight can be measured by known methods, including, but not limited to, gel permeation chromatography or intrinsic viscosity.

After the functionalized polymer has been reacted with DVS to create a first derivative of the polymer, this first derivative is then reacted with a nucleophile, e.g., a thiol derivative, of a formula selected from X—$R_1$ and X—$R^2$—Y to provide a second derivative of the polymer. In these formulae, $R^1$ is substituted or unsubstituted $C_1$-$C_{20}$ aliphatic or aromatic, $R_2$ is substituted or unsubstituted $C_1$-$C_{20}$ aliphatic or aromatic, X is a nucleophilic group, and Y is selected from carboxylic acid, sulfonic acid and hydroxyl. The nucleophile contains a thiol group as X in a thiol derivative. In general, the thiol derivative can be a single compound or a mixture of thiol compounds. Examples are alkyl thiols, which may be, e.g., linear, branched, or cyclic, such as methanethiol, ethanethiol, etc. Alternatively, the thiol may be an aryl thiol, a charged thiol, a polymeric thiol, peptides with thiol groups, proteins with thiol groups, heterocycles with thiol groups, drugs, e.g., active pharmaceutical ingredients, that contain thiol groups, growth factors with thiol groups, and biologically active agents with thiol groups.

For example, thiol compounds that can be used in the present disclosure are compounds that contain at least one free thiol group that is capable of reaction with a vinyl sulfone group via a Michael addition reaction.

The thiol compound may be identified by the formula $R_1SH$ or $R_2SH$, where $R_1$ and $R_2$ may be an aliphatic or aromatic moiety, either of which may have one or more substituents, e.g., be a substituted aliphatic moiety or a substituted aromatic moiety. An aliphatic moiety refers to an alkyl or cycloalkyl moiety, either having 1-20 carbon atoms.

"Alkyl" refers to a straight or branched hydrocarbon chain radical consisting solely of carbon and hydrogen atoms, containing no unsaturation, having from one to the specified number of carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. In one aspect the alkyl group has 1 carbon. In one aspect the alkyl group has 2 carbons. In one aspect the alkyl group has 3 carbons. In one aspect the alkyl group has 4 carbons. In one aspect the alkyl group has 4 carbons. In one aspect the alkyl group has 5 carbons. In one aspect the alkyl group has 6 carbons. Two or more of these aspects may be combined to describe derivatives of the disclosure.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically herein, a cycloalkyl group may be optionally substituted by one or more substituents independently selected at each occurrence.

An aromatic moiety refers to a carbocyclic aromatic moiety, a.k.a., an aryl moiety, or a heteroaromatic moiety, a.k.a., a heteroaryl moiety, either having 1-20 carbon atoms, the heteroaromatic moiety having at least one heteroatom selected from sulfur, oxygen and nitrogen.

"Aryl" refers to a hydrocarbon ring system radical comprising hydrogen, 6 to 18 carbon atoms and at least one aromatic ring. In one aspect the aryl ring system has 6 to 12 carbon atoms. In one aspect the aryl ring system has 6 to 10 carbon atoms. For purposes of this disclosure, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group may be optionally substituted by one or more substituents independently selected at each occurrence.

"Heteroaryl" refers to "aryl" as defined herein, wherein the aromatic ring includes one or more heteroatoms, preferably selected from N, O and S. Thus, a heteroaryl radical refers to an aromatic ring system radical wherein the ring atoms are selected from carbon, nitrogen, oxygen and sulfur, and include at least one of nitrogen, oxygen and sulfur. For purposes of this disclosure, the heteroaryl radical may be a monocyclic, bicyclic, tricyclic or tetracyclic ring system, which may include fused or bridged ring systems. Optionally, the heteroaryl radical is a 5-, 6- or 7-membered heteroaryl group. When there are multiple O and S atoms in the heteroaryl ring system, the O atoms and/or S atoms are preferably not linked directly to one another. Exemplary heteroaryl groups include 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole. The heteroaryl group may be a 6-membered ring, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or fused rings including a 6-membered ring such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquin-oline, acridine, phenothiazine, phenoxazine, benzopyridazine, benzopyrimi-dine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, and benzothiadiazo-thiophene. Unless stated otherwise specifically in the specification, the ring atoms of a heteroaryl group may be optionally substituted by one or more substituents independently selected at each ring atom.

A substituted $C_1$-$C_{20}$ aliphatic or aromatic moiety refers to a $C_1$-$C_{20}$ aliphatic or aromatic moiety having one or more substituents, where a "substituent" refers to monovalent group that may be attached to a mentioned moiety. For example, a "substituted phenyl" refers to a phenyl ring having 1, 2, 3 or 4 substituents attached to the phenyl ring. Substituents may be selected from halogen, $C_1$-$C_6$alkyl, $C_1$-$C_6$haloalkyl, $C_1$-$C_6$hydroxyalkyl, —OH, —O($C_1$-$C_6$alkyl), —O($C_1$-$C_6$haloalkyl), —O($C_1$-$C_6$hydroxyalkyl), —S($C_1$-$C_6$alkyl), —S($C_1$-$C_6$haloalkyl), —S($C_1$-$C_6$hydroxyalkyl), cyano, amino (—$NH_2$), formyl (—CHO), carboxylic acid (—COOH), carboxylate ester (—COOR where R is a $C_1$-$C_{10}$ alkyl group).

These thiol compounds include alkyl thiols which may be linear, branched or cyclic, aryl thiols, charged thiol compounds, polymers that contain a free thiol, peptides that contain a free thiol, heterocycles that contain a free thiol, drugs or biologically active compounds with a free thiol, growth factors with a free thiol, antibodies or antibody fragments with a free thiol and proteins with a free thiol. Examples of such thiol compounds include, and are not limited to thiophenol, 2-phenylethanethiol, triphenylmethanethiol, 4-methylbenzenethiol, 4-aminothiophenol, 2-aminothiophenol, 4-methoxy-α-toluenethiol, 4-nitrothiophenol, 4-tert-butylbenzenethiol, 2-mercapto-2-phenylacetic acid, 4-mercaptobenzoic acid, 2-mercaptobenzoic acid (thiosalicylic acid), 3-mercapto-1-propanol, 1-mercapto-2-propanol, 4-mercapto-1-butanol, 3-mercapto-1-hexanol, 6-mercapto-1-hexanol, 8-mercapto-1-octanol, 9-mercapto-1-nonanol, 11-mercapto-1-undecanol, 4-mercapto-4-methylpentan-2-ol, ethanethiol, 1-propanethiol, 2-propanethiol, 1-butanetiol, 1-Pentanethiol, 1-hexanethiol, 2-ethylhexanethiol, 1-heptanethiol, 1-octanethiol, 1-nonanethiol, 1-decanethiol, 1-undecanethiol, 1-dodecanethiol, 1-tetradecanethiol, 1-hexadecanethiol, cis-9-octadecene-1-thiol, 1-octadecanethiol, 2-methyl-1-butanethiol, 3-methyl-1-butanethiol, cycloalkyl, cyclohexanethiol, cyclopentanethiol, sodium 3-mercapto-1-propanesulfonate, sodium mercaptopyruvate, 6-mercaptohexanoic acid, 8-mercaptooctanoic acid, 11-mercaptoundecanoic acid, 16-mercaptohexadecanoic acid, sodium 2-mercaptoethanesulfonate, 3-mercaptopropionic acid, 2-amino-4-mercaptobutyric acid (DL-homocysteine), L-cysteine, 11-mercaptoundecylphosphoric acid, 2-mercapto-1-methylimidazole, 1-benzyl-2-mercaptoimidazole, 2-mercapto-6-methylpyridine, 3-mercapto-2-butanone, 3-mercapto-3-methyl-1-butyl-1-formate, 3-mercapto-3-methylbutan-1-ol, 7-mercapto-4-methylcoumarin, 2-mercapto-4-methyl-5-thiazoleacetic acid, 2-mercapto-5-nitrobenzimidazole, 2-mercapto-5-benzimidazolesulfonic acid sodium salt dihydrate, 3-mercapto-N-nonylpropionamide, 2-mercapto-4-methylpyrimidine hydrochloride, 2-mercapto-2-phenylacetic acid, 2-mercapto-3-(trifluoromethyl)pyridine, 2-mercapto-N-m-tolylacetamide, and 4-mercapto-4-methylpentan-2-ol are exemplary thiol compounds.

Polymers with free thiols include but are not limited to Thiol-PEG3-phosphonic acid, poly(L-lactide), thiol terminated 5000, poly(L-lactide), thiol terminated 2500, PEG-SH 3000, PEG-SH 5000, thiol-functionalized hyaluronic acid, thiol-functionalized chitosan, thiol functionalized alginate, thiol functionalized dextran, thiol functionalized chondroitin sulfate and thiol functionalized carboxymethyl cellulose.

Examples of thiol functionalized hyaluronic acid include but are not limited to a thiol group linked to hyaluronic acid through a hydrazide compound as described in U.S. Pat. No. 7,981,871, through carbodiimide groups as described in U.S. Pat. No. 6,884,788, as well as those described in U.S. Pat. No. 8,124,757.

Examples of thiol functionalized chitosan include but are not limited to chitosan-cysteine conjugates, chitosan-thioglycolic acid conjugates and chitosan-4-thio-butylamidine conjugates.

Non-degradable thiol functionalized polymers include but are not limited to polycarbophil-cysteamine conjugates, polycarbophil-cysteine conjugates, and poly(acrylic acid)-homocysteine conjugates.

Thiolated peptides or peptides that contain at least of free thiol, include but are not limited to a cysteine terminated peptide containing residues 73-92 of the knuckle epitope of BMP-2 (N→C: SEQ ID NO: 1: KIPKASSVPTELSAIST-LYLSGGC), thiolated gelatin (see, e.g., U.S. Pat. Nos. 7,928,069 and 7,981,871), cysteine terminated cell adhesion epitopes such as Arg-Gly-Asp (RGD), Arg-Gly-Asp-Ser (SEQ ID NO: 2: RGDS) and Ile-Lys-Val-Ala-Val (SEQ ID NO: 3: IKVAV), cysteine terminated TAT peptide (SEQ ID NO: 4: GRKKRRQRRRPQ), laminin peptide sequence Cys-Ser-Arg-Ala-Arg-Lys-Gln-Ala-Ala-Ser-Ile-Lys-Val-Ala-Val-Ser-Ala-Asp-Arg (SEQ ID NO: 5: CSRARKQAASIK-VAVSADR; lam-IKVAV), and cysteine terminated Elastin-like polypeptides such as those of the sequence (SEQ ID NO: 6: V P G X G)n where X=any amino acid except proline.

Thiol containing drugs include but are not limited to Captopril, Thiorphan, Tiopronin and Penicillamine.

Suitable proteins that contain a cysteine group include but are not limited to an IL-3 variant (see, e.g., U.S. Pat. No. 5,166,322), an IL-2 variant (see, e.g., U.S. Pat. No. 5,206,344), protease nexin-1 variants (see, e.g., U.S. Pat. No. 5,766,897), Cysteine variants of granulocyte-macrophage colony-stimulating factor (see, e.g., U.S. Pat. No. 7,148,333; and Bioconjugate Chem., 2005, 16 (5), pp 1291-1298; DOI: 10.1021/bc050172r), cysteine modified maize ribosome-inactivating protein (maize RIP) [see, e.g., Toxins 2016, 8, 298; doi:10.3390/toxins8100298], cysteine analog of erythropoietin [see, e.g., Int J Nanomedicine. 2011; 6: 1217-1227; doi: 10.2147/IJN.S19081], reduced antibody fragments [see, e.g., Protein Eng Des Sel (2007) 20 (5): 227-234.DOI: https://doi.org/10.1093/protein/gzm015], and cysteine analogues of Bone Morphogenetic Protein-2 (see, e.g., Bioconjugate Chem., 2010, 21 (10), pp 1762-1772; DOI: 10.1021/bc9005706.

Suitable growth factors that comprise a free thiol group include but are not limited to Cysteine Analogs of Human Basic Fibroblast Growth Factor (hbFGF) [see, e.g., Tropical Journal of Pharmaceutical Research October 2014; 13 (10): 1601-1607; http://dx.doi.org/10.4314/tjpr.v13i10.5; and Protein Expr. Purif. 2006 July; 48(1):24-7https://doi.org/10.1016/j.pep.2006.02.002]).

In one aspect, the present disclosure provides a process comprising: reacting hydroxyl groups attached to a polymer, such as hydroxyl groups on hyaluronic acid (HA), with divinyl sulfone (DVS) to provide a first derivative of the polymer; and reacting the first derivative of the polymer with a nucleophile of a formula selected from X—$R^1$ and X—$R^2$—Y to provide a second derivative of the polymer. The first derivative will have a number of ethenyl (vinyl) groups attached to sulfone groups that are, in turn attached through an oxyethylene group to the polymer. Some or all of these vinyl groups are reacted with a nucleophilic compound, e.g., a thiol derivative as described above. The extent to which these vinyl groups undergo reaction may be specified according to the present disclosure. In one aspect, all or nearly all, e.g., 100%, or 99-100%, or 98-100%, or 97-100%, or 96-100%, or 95-100% are substituted with the thiol derivative. In another aspect, partial substitution is achieved with the thiol derivative, e.g., 1-95% of the free available vinyl sulfone groups are derivatized.

For example, in one aspect the number of vinyl sulfone residues, that are attached to the polysaccharide, and that can be reacted with a free thiol-containing compound can be altered. The percentage of the residual vinyl sulfone groups reacted with a free thiol-containing compound can vary from ≥1% to 100%. NMR, such as $^1$H-NMR, can be used to determine the percent substitution. When 100% substitution of the vinyl sulfone groups occurs, essentially all of the available vinyl sulfone residues attached to the polysaccharide have reacted with the free thiol-containing compound to form a thioether linkage. If less than 100% of the available vinyl sulfone groups react with the free thiol-containing compound, the polysaccharide will comprise both vinyl sulfone groups as well as compounds attached via a thioether linkage. The fraction of the repeat units of the polysaccharide that are substituted through a thioether linkage can be determined by NMR, usually $^1$H-NMR. The percent substitution, often calculated on a molar basis, can range from ≥1% to 100%, preferably greater than 10% and more preferably greater than 25%.

In one aspect, the Michael addition reaction of a free-thiol compound with the vinyl sulfone residue on the polysaccharide can occur using a single free-thiol containing compound. In another aspect, the addition reaction can occur using more than 1 free thiol-containing compound in which the free thiol-containing compounds are different from each other.

Figure 2:
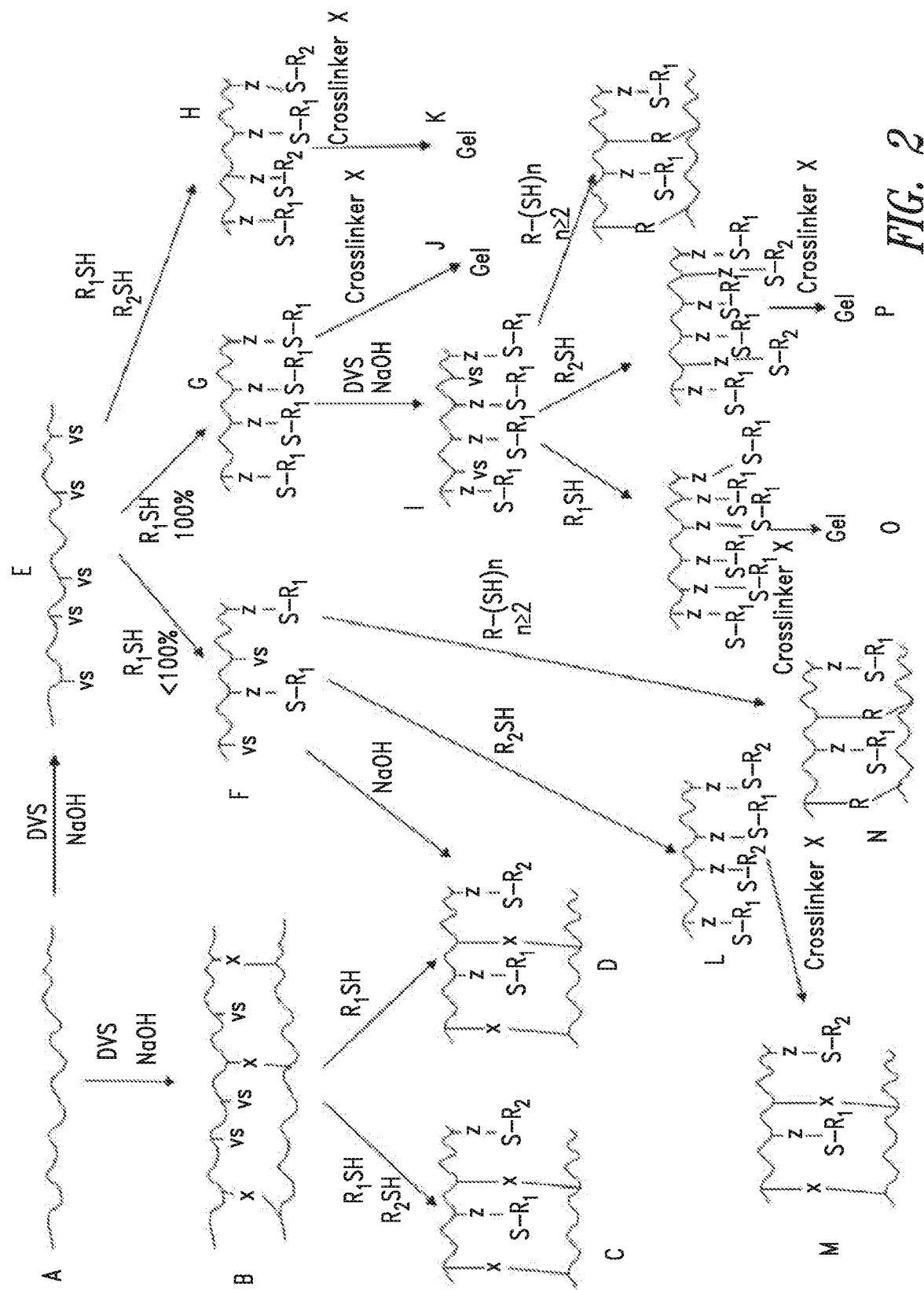
FIG. 2 shows exemplary reactions of the present disclosure.

FIG. 2 illustrates options for performing polymer derivatization reactions according to the present disclosure. In FIG. 2, "A" identifies a hydroxyl-substituted polymer such as hyaluronic acid or polyvinylalcohol. The polymer A may be characterized in terms of molecular weight. In one aspect, the intrinsic viscosity of polymer A is used as an indicator of the polymer's molecular weight. Optionally, the intrinsic viscosity of polymer A is in the range of 0.3 to 3 m$^3$/Kg. In another aspect, chromatography is used to characterize the molecular weight of polymer A. Optionally, the weight average molecular weight of polymer A is approximately 75,000 Da to 3,000,000 Da.

In FIG. 2, "B" identifies the product of reacting polymer A with divinyl sulfone (DVS) under basic conditions (NaOH in an aqueous solvent). Polymer B is a compound of the present disclosure. Polymer B is shown as two polymers. As joined together through X linkages, where X represents a diethyl sulfone group of the formula —CH$_2$—CH$_2$—SO$_2$—CH$_2$—CH$_2$— which is linked at each of its ends to an oxygen atom that was formerly part of a hydroxyl group from polymer A. The X groups are created by reaction of two hydroxyl groups reacting with two vinyl groups of divinyl sulfone. The X groups are shown linking together two different A polymers, however an X group may also link together two hydroxyl groups of a single A polymer to provide a polymer B according to the present disclosure.

In FIG. 2, "B" contains three X linkages between two A polymers in addition to three VS groups. A VS group is the result of a divinyl sulfone substitution reaction with a hydroxyl group of an A polymer. In order to create a VS group, one and only one of the two vinyl groups of a divinyl sulfone molecule reacts with one and only one hydroxyl group of a polymer A. In one aspect of the present disclosure, hydroxy-substituted polymers ("A") are reacted with divinyl sulfone (DVS) to create linkages between two or more hydroxyl groups in a mixture of hydroxyl substituted polymer chains, and additionally to create vinyl sulfone substituents on one or more hydroxyl-substituted polymer chains (shown as polymer B in FIG. 2).

In one aspect, the polymer B still contains unreacted hydroxyl groups. For example, when a flask is charged with a desired amount of polymer A comprising a specified number of hydroxyl groups, the addition of DVS will consume at least 5%, or least 10%, or at least 20%, or at least 30%, or at least 40%, or at least 50%, or at least 60%, or at least 70%, or at least 80% of those initial hydroxyl groups in the formation of X and VS groups present in polymer B. The number of hydroxyl groups present after reaction of DVS may also, or alternatively be described in terms of the residual hydroxyl groups, so that at least 15%, or at least 20%, or at least 25%, or at least 30%, or at least 35%, or at least 40%, or at least 50%, or at least 60%, or at least 70%, or at least 80% of the initial hydroxyl groups are still present in polymer B. The number of hydroxyl groups present in polymer B may also be expressed as a range of the initial number of hydroxyl group present in polymer A, e.g., the conversion of polymer A to polymer B may consume 5-10% of the available hydroxyl groups, or in other aspects, 5-15%, or 5-20%, or 5-25%, or 5-30%, or 5-35%, or 10-15%, or 10-20%, or 10-25%, or 10-30%, or 10-35%, or 10-40% of the initially available hydroxyl groups.

In one aspect, the polymer B contains both X and VS substituents. In one aspect, the polymer B contains both X and VS substituents in a molar ratio of where the number of VS groups exceeds the number of X groups. However, in another aspect, the number of X groups exceeds the number of VS groups. In other aspects, the X groups provide at least 5%, 10%, 20%, 30%, 40%, 50%, 60%, 70%, 80%, or at least 90% of the total number of X and VS groups.

As shown in FIG. 2, polymer B may serve as a reactant to create either polymer C or polymer D, each of which is a polymer according to the present disclosure. To create polymer C, a mixture of nucleophilic compounds, represented as R$_1$SH and R$_2$SH in FIG. 2, is reacted with polymer B. To create polymer D, a single nucleophilic compound, represented as R$_1$SH in FIG. 2, is reacted with polymer B. The present disclosure provides polymer B, polymer C, polymer D as well as reactions to create polymer B from polymer A, reactions to create polymer C from polymer B, and reactions to create polymer D from polymer B. In one aspect, each of polymers A, B and C is a derivatized hyaluronic acid.

Polymer D contains X moieties which link together two polymer A chains. In addition, polymer D contains Z—S—R$_1$ moieties which are created by the reaction of the vinyl sulfone (VS) groups of polymer B with thiol compound R$_1$SH to provide —O—CH$_2$—CH$_2$—SO$_2$—CH$_2$—CH$_2$—S—R$_1$ moieties, which are abbreviated as Z—S—R1 moieties in FIG. 2. In one aspect, the present disclosure provides polymer D having a mixture of X groups and Z—S—R$_1$ groups. In one aspect, X groups provide at least 10%, or at least 20%, or at least 30%, or at least 40%, or at least 50%, or at least 60%, or at least 70%, or at least 80%, or at least 90% of the total of the X and Z—S—R$_1$ groups. In one aspect, Z—S—R$_1$ groups provide at least 10%, or at least 20%, or at least 30%, or at least 40%, or at least 50%, or at least 60%, or at least 70%, or at least 80%, or at least 90% of the total of the X and Z—S—R$_1$ groups.

In one aspect, the present disclosure provides polymer E having a structure as set forth in FIG. 2. In one aspect, the present disclosure provides polymer F having a structure as identified in FIG. 2. In another aspect, the present disclosure provides polymer G having a structure as identified in FIG. 2. In yet another aspect, the present disclosure provides polymer H having a structure as identified in FIG. 2.

As shown in FIG. 2, polymer A may be reacted with divinyl sulfone under basic conditions to provide polymer E. As shown in FIG. 2, polymer E may be formed from polymer A by reaction of the hydroxyl groups of polymer A with divinyl sulfone (DVS) to convert them to vinyl sulfone (VS) groups. In polymer E, there are few, if any, X groups which link together two hydroxyl groups of polymer A. In various aspects, the VS groups constitute at least 80%, or at least 85%, or at least 90%, or at least, 95%, or at least 96%, or at least 97%, or at least 98%, or at least 99%, or at least 99.5%, or at least 99.9% of the total of X and VS groups present in polymer E.

Polymer E may be reacted with $R_1SH$, optionally in combination with one or more additional nucleophilic compounds, e.g., $R_2SH$, to provide polymers of structure F, G or H, as shown in FIG. 2. Polymer F has a mixture of residual VS groups and Z—S—R1 groups formed by reaction of VS groups with $R_1SH$. The charge of $R_1SH$ is less than 100% of the total number of VS groups present on polymer E, calculated on a molar basis. Based on this stoichiometry, not all of the VS groups will react with $R_1SH$ molecules, and accordingly polymer F has a mixture of VS and Z—S—$R_1$ groups. In one aspect, VS groups provide at least 10%, or at least 20%, or at least 30%, or at least 40%, or at least 50%, or at least 60%, or at least 70%, or at least 80%, or at least 90% of the total of the VS and Z—S—R1 groups. In one aspect, Z—S—$R_1$ groups provide at least 10%, or at least 20%, or at least 30%, or at least 40%, or at least 50%, or at least 60%, or at least 70%, or at least 80%, or at least 90% of the total of the VS and Z—S—$R_1$ groups.

Polymer G has a majority of Z—S—$R_1$ groups, and little or no X and VS groups. In various aspects, the Z—S—$R_1$ groups constitute at least 80%, or at least 85%, or at least 90%, or at least, 95%, or at least 96%, or at least 97%, or at least 98%, or at least 99%, or at least 99.5%, or at least 99.9% of the total of X, VS and Z—S—$R_1$ groups present in polymer G. Polymer G may be formed by reaction of polymer E and an equimolar or molar excess of $R_1SH$ molecules, based on the moles of available VS groups.

Polymer H has a majority of Z—S—$R_1$ and Z—S—$R_2$ groups, and little or no X and VS groups. In various aspects, the total of the Z—S—$R_1$ and Z—S—$R_2$ groups constitute at least 80%, or at least 85%, or at least 90%, or at least, 95%, or at least 96%, or at least 97%, or at least 98%, or at least 99%, or at least 99.5%, or at least 99.9% of the total of X, VS, Z—S—$R_1$ and Z—S—$R_2$ groups present in polymer H. Polymer H may be formed by reaction of polymer E and a mixture of nucleophilic compounds, e.g., a mixture of $R_1SH$ and $R_2SH$, such as shown in FIG. 2.

In one aspect, the present disclosure provides polymer I having a structure as set forth in FIG. 2. In one aspect, the present disclosure provides polymer J which is a gel prepared as shown in FIG. 2. In another aspect, the present disclosure provides polymer K which is a gel prepared as shown in FIG. 2.

Polymer I has a mixture of Z—S—$R_1$ and VS substituents. In one aspect, the present disclosure provides polymer I having a mixture of VS groups and Z—S—$R_1$ groups. In one aspect, VS groups provide at least 10%, or at least 20%, or at least 30%, or at least 40%, or at least 50%, or at least 60%, or at least 70%, or at least 80%, or at least 90% of the total of the VS and Z—S—$R_1$ groups. In one aspect, Z—S—$R_1$ groups provide at least 10%, or at least 20%, or at least 30%, or at least 40%, or at least 50%, or at least 60%, or at least 70%, or at least 80%, or at least 90% of the total of the VS and Z—S—$R_1$ groups. Polymer I may be formed by reacting polymer G with divinylsulfone under basic conditions. This reaction converts hydroxyl groups present on polymer G (not shown in FIG. 2) to vinyl sulfone (VS) groups.

Polymers J and K are gels which may be prepared as shown in FIG. 2. Polymer J may be formed by crosslinking polymer G. Polymer K may be formed by crosslinking polymer H.

In one aspect, the present disclosure provides polymer L having a structure as set forth in FIG. 2. In another aspect, the present disclosure provides polymer M having a structure as identified in FIG. 2. In yet another aspect, the present disclosure provides polymer N having a structure as identified in FIG. 2.

Polymer L as shown in FIG. 2 contains a mixture of Z—S—$R_1$ and Z—S—$R_2$ substituents. Polymer L may additionally contain hydroxyl substituents (not shown). In various aspects, the total of the Z—S—$R_1$ and Z—S—$R_2$ groups constitute at least 80%, or at least 85%, or at least 90%, or at least, 95%, or at least 96%, or at least 97%, or at least 98%, or at least 99%, or at least 99.5%, or at least 99.9% of the total of X, VS, Z—S—$R_1$ and Z—S—$R_2$ groups present in polymer L. Polymer L may be formed by reaction of polymer F, which contains Z—S—$R_1$ and VS substituents, with $R_2SH$, to thereby convert the VS substituents to Z—S—$R_2$ substituents.

Polymer M as shown in FIG. 2 contains a mixture of X, Z—S—$R_1$ and Z—S—$R_2$ groups. Polymer M may additionally contain hydroxyl substituents (not shown). Polymer M may be formed by adding a crosslinker, such as divinylsulfone, to Polymer L that contains residual hydroxyl groups. The crosslinker creates X groups between hydroxyl groups present on polymer L.

Polymer N as shown in FIG. 2 contains a mixture of Z—S—$R_1$ and —R— groups, where an R group forms a linkage between different polymer A chains. The R groups may be introduced by reacting a precursor polymer, such as polymer F or other polymer containing VS groups, with a polyfunctional nucleophile, such as $R(SH)n$ where n is greater than or equal to 2. In $R(SH)n$, R represents an aliphatic or aromatic group that is optionally substituted.

In one aspect, the present disclosure provides polymer O which is a gel that may be formed as shown in FIG. 2. In another aspect, the present disclosure provides polymer P which is a gel that may be formed as shown in FIG. 2.

Polymer O may be formed from Polymer I by a two-step reaction. In a first step, polymer I is reacted with a nucleophilic compound, such as $R_1SH$, to convert VS groups present on polymer I, into the corresponding Z—S—$R_1$ groups. In a second step, a crosslinker X is added to this intermediate polymer to provide a polymeric gel O.

Polymer P may be formed from Polymer I by a two-step reaction. In a first step, polymer I is reacted with a nucleophilic compound, such as $R_2SH$, to convert VS groups present on polymer I, into the corresponding Z—S—$R_2$ groups. In a second step, a crosslinker X is added to this intermediate polymer to provide a polymeric gel P.

Polymer I may also serve as a precursor to a crosslinked polymer having —R— groups as the linkage between polymer chains. The R groups may be introduced by reacting a polymer I, or another polymer containing VS groups, with a polyfunctional nucleophile, such as R(SH)n where n is greater than or equal to 2. In R(SH)n, R represents an aliphatic or aromatic group that is optionally substituted.

Figure 3:
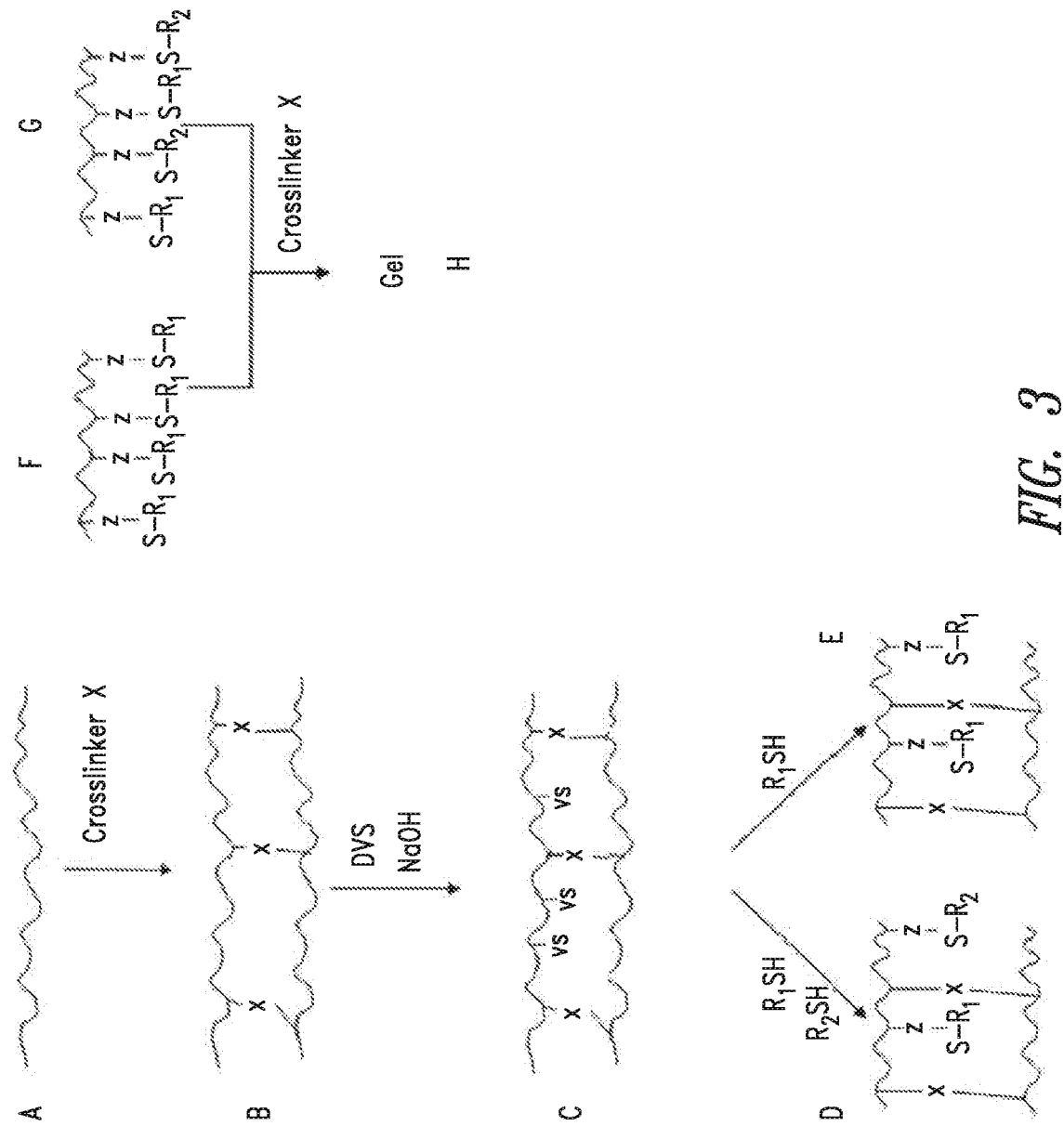
FIG. 3 shows exemplary reactions of the present disclosure.

FIG. 3 illustrates options for performing polymer derivatization reactions according to the present disclosure. In FIG. 3, "A" identifies a hydroxyl-substituted polymer such as hyaluronic acid or polyvinylalcohol, which is likewise shown as polymer A in FIG. 2. However, in contrast to FIG. 2, the reaction schemes of FIG. 3 begin by performing a crosslinking reaction on polymer A, and achieving little or no conversion of hydroxyl groups on polymer A into an alternative monofunctional reactive group.

As shown in FIG. 3, polymer A may be reacted with a crosslinking agent, to provide a crosslinked version of polymer A, which is denoted as polymer B in FIG. 3. Suitable crosslinking reactions for hydroxyl-containing polymers are described elsewhere herein.

In one aspect, the present disclosure provides polymer C having a structure as set forth in FIG. 3. In another aspect, the present disclosure provides polymer D having a structure as identified in FIG. 3. In yet another aspect, the present disclosure provides polymer E having a structure as identified in FIG. 3.

Polymer C may be formed by reacting polymer B with divinyl sulfone (DVS) under basic conditions. Under these reaction conditions, hydroxyl groups present on polymer B (not shown) react with DVS to convert hydroxyl groups to VS groups. In one aspect, VS groups provide at least 10%, or at least 20%, or at least 30%, or at least 40%, or at least 50%, or at least 60%, or at least 70%, or at least 80%, or at least 90% of the total of the VS and X groups present in polymer C. In one aspect, X groups provide at least 10%, or at least 20%, or at least 30%, or at least 40%, or at least 50%, or at least 60%, or at least 70%, or at least 80%, or at least 90% of the total of the VS and X groups present in polymer C.

Polymer D in FIG. 3 is a crosslinked polymer having both Z—S—$R_1$ and Z—S—$R_2$ substituents. Polymer D may be formed by reacting polymer C with a mixture of nucleophilic compounds, such as $R_1$SH and $R_2$SH as shown in FIG. 3. In one aspect, the total of the Z—S—$R_1$ and Z—S—$R_2$ groups provide at least 10%, or at least 20%, or at least 30%, or at least 40%, or at least 50%, or at least 60%, or at least 70%, or at least 80%, or at least 90% of the total of the Z—S—$R_1$, Z—S—$R_2$ and X groups present in polymer D. In one aspect, X groups provide at least 10%, or at least 20%, or at least 30%, or at least 40%, or at least 50%, or at least 60%, or at least 70%, or at least 80%, or at least 90% of the total of the Z—S—$R_1$, Z—S—$R_2$ and X groups present in polymer D.

Polymer E in FIG. 3 is a crosslinked polymer having Z—S—$R_1$ substituents (but not having any and Z—S—$R_2$ substituents). Polymer E may be formed by reacting polymer C of FIG. 3 with a nucleophilic compound, such as $R_1$SH as shown in FIG. 3. In one aspect, the Z—S—$R_1$ groups provide at least 10%, or at least 20%, or at least 30%, or at least 40%, or at least 50%, or at least 60%, or at least 70%, or at least 80%, or at least 90% of the total of the Z—S—$R_1$ and X groups present in polymer E. In one aspect, X groups provide at least 10%, or at least 20%, or at least 30%, or at least 40%, or at least 50%, or at least 60%, or at least 70%, or at least 80%, or at least 90% of the total of the Z—S—$R_1$ and X groups present in polymer E.

As also shown in FIG. 3, the present disclosure provides polymers of structure F and of structure G, as well as crosslinked gels thereof. Polymer F of FIG. 3 contains Z—S—R1 substituents, while polymer G contains a mixture of Z—S—R1 and Z—S—R2 substituents. Neither of polymers F or G are crosslinked polymers. However, each of polymers F and G may be treated with a crosslinking agent, or exposing to crosslinking conditions, to provide the corresponding crosslinked polymer which will have the form of a gel (identified as polymer H in FIG. 3).

Though not wishing to be bound by any particular theory, it is believed that there may be none to a low level of crosslinking occurring when vinyl groups are present in in a solution of derivatized polyhydric polymer molecules. This "accidental" crosslinking may be present but is not measurable and the solution does not exhibit characteristics of cross-linking, and would be referred to herein as a solution or composition comprising non-cross-linked derivatives of polymeric polyhydric alcohols.

Thus, in one aspect, the present disclosure provides vinyl sulfone functionalization (i.e., derivatization) of a polysaccharide ("a first derivative") followed by reaction of the vinyl sulfone substituent with one or more free thiol-containing compounds ("a second derivative") which is in turn followed by a second functionalization (i.e., derivatization) reaction with divinyl sulfone to produce a polysaccharide that is functionalized with compounds through a thioether linkage as well as with vinyl sulfone functional groups ("a third derivative"). In another aspect, the above compounds can be further reacted with free thiol-containing compounds ("a fourth derivative"). The molar ratio of the free thiol-compound used for the reaction can be altered such that 1% to 100% of the second added vinyl sulfone functional groups are reacted. The free thiol-containing compound that is used in the second Michael addition reaction (derivatization reaction) can be the same or it can be different from that used in the first Michael addition reaction. For the second Michael addition reaction, a single free thiol-containing compound can be used or a mixture of 2 or more different free-thiol containing compounds can be used. In another aspect, at least one additional round of vinyl sulfone/free thiol-containing compound reactions cycles can be performed using the same free-thiol containing compound or one or more different free-thiol containing compounds In one aspect, a process of the present disclosure further comprises crosslinking a second derivative of the polymer, e.g., crosslinking by reacting the second derivative of the polymer with a crosslinking agent. Upon crosslinking, the second derivative is converted to a third derivative of the polymer, where the third derivative is a crosslinked polymer.

For example, in one aspect, a polysaccharide derivatized with one or more free-thiol containing compounds and also comprises residual available vinyl sulfone functional groups can undergo crosslinking by subjecting a solution of the derivatized polyhydric polymer to basic conditions that are sufficient to allow the residual available vinyl sulfone group to react with a hydroxyl group of the polysaccharide. In one aspect, the reaction pH is greater than 12 for example, in the 12.5 to 13.0 pH range. The amount of residual vinyl sulfone functional groups, often measured as percent substitution as measured by $^1$H-NMR, reaction time and reaction temperature can be selected to achieve the desired degree of crosslinking.

In another aspect, a polysaccharide derivatized with one or more free-thiol containing compounds and also comprises residual available vinyl sulfone functional groups can be mixed with a polysaccharide derivatized with one or more free-thiol containing compounds and also comprises residual available vinyl sulfone functional groups wherein the free-thiol containing compounds can be the same or different or a combination thereof. The resultant mixture can undergo crosslinking by subjecting a solution of the derivatized polyhydric polymer to basic conditions that are sufficient to allow the residual available vinyl sulfone group to react with a hydroxyl group of the polysaccharide. In one aspect, the reaction pH is greater than 12, for example, in the 12.2 to 13 pH range. The amount of residual vinyl sulfone functional groups, often measured as percent substitution as measured by $^1$H-NMR, reaction time and reaction temperature can be selected to achieve the desired degree of crosslinking.

In another aspect, a non-derivatized polysaccharide can be added to the crosslinking reaction mixtures described above and the resultant mixture can undergo crosslinking by subjecting the solution of derivatized polymeric polyhydric alcohol and the non-derivatized polysaccharide to basic conditions that are sufficient to allow the residual available vinyl sulfone groups of the derivatized polymeric polyhydric alcohol to react with a hydroxyl group of the polysaccharide. In one aspect, the reaction pH is greater than 12, for example, in the 12.2 to 13 pH range. The amount of residual vinyl sulfone functional groups, often measured as percent substitution as measured by $^1$H-NMR, reaction time and reaction temperature can be selected to achieve the desired degree of crosslinking.

Crosslinking may be achieved by using an external crosslinking agent. In one aspect, a crosslinking agent is added to the second derivative of the polymer. Exemplary crosslinking agents that could be used include: carbodiimides, bisepoxides, divinyl sulfone derivatives, and combinations thereof. Another suitable crosslinking agent is a multiple thioether derivative. In one aspect, at least 2 (could be 2, 3, 4, etc.) different thioether derivatives are combined with a crosslinking agent and conditions are adjusted such that the derivatives of polyhydric polymers become either fully crosslinked or partially crosslinked. In this case, exemplary crosslinking agents include, without limitation, carbodiimides, bisepoxides, divinyl sulfone derivatives and combination thereof.

For example, in one aspect, a polysaccharide derivatized with one or more free-thiol containing compounds can be crosslinked by adding a crosslinking agent and adjusting the pH of the reaction mixture such that the derivatized polysaccharide forms a crosslinked derivatized polysaccharide or composition. Crosslinking agents that can be used include but are not limited to biscarbodiimides, bisepoxides, divinyl sulfone derivatives, di-isocyanates, dihalide chlorides, disuccinimidyl derivatives and combinations thereof.

Biscarbodiimide compounds can include but are not limited to para-phenylenebis-(ethyl)-carbodiimide, 1,6-hexa methylene bis(ethylcarbodiimide), 1,8-octa methylene bis (ethylcarbodiimide), 1,10 decamethylene bis(ethylcarbodiimide), 1,12 dodecamethylene bis(ethylcarbodiimide), PEG-bis(propyl(ethylcarbodiimide)), 2,2'-dithioethyl bis (ethylcarbodiimde), 1,1'-dithio-p-phenylene bis(ethylcarbodiimide); para-phenylene-bis(ethylcarbodiimide), and 1,1'-dithio-m-phenylene bis(ethylcarbodiimide).

When utilizing a biscarbodiimide crosslinker, the biscarbodiimide is mixed with a buffered aqueous solution of the derivatized carboxylic acid containing polysaccharide. The target pH of the buffered solution can be between pH 5 and pH 6.5.

Bisepoxide compounds can include but are not limited to 1,4-butanediol diglycidyl ether (BDDE), 1,2,7,8-diepoxyoctane (DEO), poly(ethylene glycol) diepoxide. When utilizing a bisepoxide crosslinker, the bisepoxide is mixed with an aqueous solution of the derivatized polysaccharide and the pH is raised to a pH >9. The reaction can be carried out at 40° C. for greater than 4 hours to produce a crosslinked derivatized polyhydric polymer.

Divinyl sulfone crosslinking agents can include but are not limited to divinyl sulfone and poly(ethylene glycol) bisvinyl sulfone.

When utilizing a divinyl sulfone crosslinker, the reaction pH in an aqueous solution can be raised to a pH greater than 12 to effect crosslinking. The degree of crosslinking can be altered by changing the amount of crosslinking agent added, reaction time, the reaction pH and reaction temperature.

In another aspect, a mixture of at least 2 different thioether derivatized polysaccharides can be mixed together, a crosslinking agent can be added and the reactions conditions adjusted such that the derivatized polyhydric polymers are crosslinked. The relative ratios of the different derivatized polysaccharides can be altered such that crosslinked derivatized polyhydric polymers with different properties are obtained. These properties include but are not limited to equilibrium swelling, swelling rate, drug release characteristics, elastic modulus, storage modulus, loss modulus, degradation, tensile strength, tissue adhesiveness and lubricity. As used herein "derivatized polyhydric polymers" may also include compositions comprising one or more derivatized polyhydric polymers.

In another aspect, at least 2 different crosslinking agents can be used to crosslink the derivatized polysaccharide. In one aspect, two different crosslinking agents from the same group could be used to crosslink the derivatized polyhydric polymers. For example, divinyl sulfone and poly(ethylene glycol) bisvinyl sulfone or 1,4-butanediol diglycidyl ether (BDDE) and poly(ethylene glycol) diepoxide could be used.

In another aspect, two different crosslinking agents from different groups could be used. For example, divinyl sulfone and 1,4-butanediol diglycidyl ether (BDDE) may be used to crosslink the derivatized polysaccharides. In another aspect, the crosslinker can be added sequentially such that initial crosslinking occurs in the presence of the first crosslinked and then the second crosslinker is added such that secondary crosslinking occurs. The reaction conditions may be changed after the first crosslinking reaction and prior to the second crosslinking reaction. Reaction conditions such as temperature, pH, buffer, ionic strength and solvent composition can be altered.

In one aspect, crosslinked derivatized polyhydric polymers can be prepared though ionic crosslinking. This can be accomplished by mixing a derivatized polyhydric polymer of this disclosure that has a negative charge with a compound that has two or more positive charges. In one aspect, a solution of the derivatized polyhydric polymer of this disclosure that has a negative charge can be prepared and then mixed with a solution of a compound that has two or more positive charges. Inorganic compounds that can be used include but are not limited to ferric chloride, aluminum chloride, chromium sulfate, and aluminum sulfate. Positively charged polymers that can be used include polymers that comprise more than two lysines, arginine or histadine amino acids, chitosan and chitosan derivatives, deacetylated hyaluronic acid, polyethyleneimine (PEI), poly(N,N-dimethylaminoethylmethacrylate), poly(4-vinylpyridine), polyethyleneglycol-polylysine block copolymers (PEG-PLL), dextran grafted polylysine copolymers, or combinations thereof.

In one aspect, the positively charged or the negatively charged polymer can first be applied. This can then be followed by application of the oppositely charged polymer such that at the interface of the two layers, ionic interactions occur such that the polymers are crosslinked together. In another aspect, the process can be repeated at least one more time.

A second derivative of the polymer (e.g., HA-(OCH$_2$CH$_2$SO$_2$CH$_2$CH$_2$—X—R$_1$—Y)$_n$) may be cross-linked via internal and external crosslinking. For example, in one aspect, a polysaccharide derivatized with one or more free-thiol containing compound and also comprising residual available vinyl sulfone functional groups can be crosslinked in the presence of an external crosslinking agent. In one aspect, the reaction conditions can be adjusted such that the residual available vinyl sulfone groups and the added external crosslinked react simultaneously. For example, divinyl sulfone can be added as the external crosslinker and then the pH can be increased to a pH >12 which will result is crosslinking.

As another example, the crosslinking via the residual available vinyl sulfone functional groups can take place first which is then followed by the addition of the external crosslinker. The reaction conditions, for example pH, can be changed to effect the crosslinking reaction of the external added crosslinker. For example, the pH of the derivatized polysaccharide that contains the residual available vinyl sulfone functional groups can be raised to a pH >12. Once the reaction has been reached the desired level, the pH can be changed to between pH 5 and pH 6.5 with a buffer and then biscarbodiimide crosslinker, for example para-phenylenebis-(ethyl)-carbodiimide, can be added to the reaction mixture and allowed to react until the desired level of crosslinking is obtained. In another aspect, the biscarbodiimide crosslinking can take place first by adjusting the pH of the derivatized polysaccharide to between 5 and 6.5, adding the biscarbodiimide, allowing the crosslinking to proceed to the desired level, then raising the pH to pH >12 to allow the residual vinyl sulfone functional groups to crosslink.

In one aspect, a polysaccharide derivatized with one or more free-thiol containing compound and also comprises residual available vinyl sulfone functional groups can be crosslinked in the presence of an external crosslinking agent that has at least two free thiol functional groups. These free thiol groups may be positioned upon a central molecule, "C". The central molecule may be a linear or cyclic alkane, a polyethylene glycol (PEG) oligomer or polymer, or any other such suitable central molecule. In the case of PEG-based crosslinking agents, the PEG may be linear, branched (having two polymer arms), or multi-armed (e.g., having 3, 4, 5, 6, 7, 8 or more polymer arms). Thus, in such instances, the central molecule will typically a linear PEG, a branched PEG having 2 arms, or a multi-armed PEG having PEG arms emanating from a central core.

Illustrative cores for such multi-armed polymers include erythritol, pentaerythritol, trimethylolpropane, glycerol, glycerol dimer (3,3'-oxydipropane-1,2-diol), glycerol oligomers, sorbitol, hexaglycerol, and the like.

Illustrative thiol crosslinking agents include PEG-dithiol (HS-PEG-SH), 3-arm PEG-tri-thiol (glycerine core), 4-arm PEG-tetrathiol (pentaerythritol core), or 8-arm PEG-octathiol (hexaglycerine core). The foregoing multi-armed PEG reagents may also have fewer than all arms functionalized with thiol. Additional suitable thiol reagents having PEG as the central molecule are available from Laysan Bio (Arab, Ala.), as well as aromatic dithiols such as those available from NanoScience. Other suitable thiol crosslinking agents include dimercaptosuccinic acid, 2,3-dimercapto-1-propanesulfonic acid, Trimethylolpropane tris(3-mercaptopropionate), dithiol functionalized pluronics F127, dithiol functionalized F68, dihydrolipoic acid, peptides containing at least 2 cysteine amino acids, thiol functionalized dextran, and thiol-functionalized hyaluronic acid.

The polymers of the present disclosure, e.g., the first, second and third derivatives of a polymer such a polysaccharide, may be processed into numerous forms. For the non-crosslinked derivatized polyhydric polymers, exemplary compositions of the derivatized polyhydric polymers include, but are not limited to, a solution, a suspension, an emulsion, a film, a gel, a coating on a surface of an article, an electrospun matrix, a microparticle, a fiber, a lyophilized solid, a rod, a disc, a gel, a powder or in a particulate form. A particulate form can be prepared by milling (e.g., jet milling, roller milling, cryomilling, mechanical milling) fragmentation, spray drying, precipitation or grinding. For the crosslinked derivatized polyhydric polymers, compositions of the derivatized polyhydric polymer can be as a suspension, a film, an electrospun matrix, a fiber, a lyophilized solid, a rod, a disc, a gel, a powder or in a particulate form. The particulate form can be prepared by milling (jet milling, roller milling, cryomilling, mechanical milling) fragmentation, spray drying, precipitation or grinding.

A solution of the derivatized polyhydric polymer can be prepared by dissolving the derivatized polyhydric polymer in an appropriate solvent or a combination of solvents. For example, water or a combination of water and water-miscible solvent can be used. Water-miscible solvents can include but are not limited to methanol, ethanol, isopropanol, dimethyl formamide (DMF) acetone, 1,4-dioxane, pyridine, dimethyl sulfoxide (DMSO), tetrahydrofuran (THF) and acetonitrile. The prepared solutions can be sterilized by filtering through a 0.2 μm sterile filter. In one aspect, a solution can be prepared using one derivatized polysaccharide. The concentration of the prepared solutions can range from, e.g., 0.01% (w/v) to about 50% (w/v). In one aspect, the concentration is in the 0.1% (w/v) to 10% (w/v) range.

A film of non-crosslinked derivatized polyhydric polymers of this disclosure can be prepared by preparing a solution of the derivatized polyhydric polymer. This solution can be then placed in a mold or drawn out on a surface using a gardner knife. The surface used can be glass, metal foil, stainless steel, Teflon, nylon, polyethylene, polypropylene or a release liner. The solvent can then be removed to form the film. The rate of solvent removal can be altered by using at least one of the following parameters: temperature, air or inert gas flow and pressure. To increase the rate of solvent evaporation, the temperature could be increased, the air or inert gas flow rate could be increased or the pressure could be decreased. A combination of these process could also be used. To slow the rate of solvent evaporation, the temperature could be decreased, the air or inert gas flow rate could be reduced or the pressure could be increased. A combination of these process could also be used. A film can comprise one of the derivatized polyhydric polymers of this disclosure. The films can also comprise two or more different derivatized polyhydric polymers of this disclosure. A composite film can be prepared by preparing a first film and then casting a second film on top of the first film. A composite film can be prepared by casting additional layers sequentially on top of the previous layer. The layers of the composite film can comprise the same derivatized polyhydric polymer if the disclosure, different derivatized polyhydric polymers of this disclosure or a combination thereof.

Lyophilized forms of the non-crosslinked derivatized polyhydric polymers of this disclosure can be prepared by making a solution of the derivatized polyhydric polymer, freezing the solution and then placing the frozen derivatized polyhydric polymer solution under a vacuum such that the solvent is sublimed off to leave the derivatized polyhydric polymer composition in the solid form. A lyophilized form of the derivatized polyhydric polymer composition of this disclosure can comprise one of the derivatized polyhydric polymers of this disclosure. In another aspect, the lyophilized form of the derivatized polyhydric polymers and/or compositions of this disclosure can comprise two or more different derivatized polyhydric polymers of this disclosure. In another aspect, a lyophilized composition of one or more derivatized polyhydric polymers can comprise one or more derivatized polyhydric polymers in addition to an additive such as chitosan or chitosan derivatives (e.g. chitosan HCL, chitosan acetate, or chitosan lactate). The form of the lyophilized derivatized polyhydric polymer compositions may be dependent on the form of the container into which the solution was poured. In another aspect, the form of the lyophilized derivatized polyhydric polymer may be dependent on the form of the contained into which the solution was poured and frozen. The form can be a rectangle, square, disk, triangle, trapezoid, rod or any other form in which a mold can be made.

A derivatized polyhydric polymer compositions of this disclosure can be in the form of a powder or particulate. The powder or particulate may be obtained directly via precipitation. A powder or particulate form can also be obtained through a milling, grinding, spray drying or fragmentation process. Compositions, including but not limited to, films, precipitated derivatized polyhydric polymers, dried derivatized polyhydric polymers and/or compositions, lyophilized derivatized polyhydric polymers and/or compositions, or derivatized polyhydric polymers and/or compositions, dried in a form can be further process via a milling process (jet milling, roller milling, cryomilling, mechanical milling), a grinding or a fragmentation process. A combination of these processes can be used. Derivatized polyhydric polymer composition with particle size in the range of 100 nm to 5 mm can be prepared. Specific size ranges of the powdered or particulate derivatized polyhydric polymer compositions of this disclosure can be prepared by separating the derivatized polyhydric polymer composition particles according to size using sieves. The distribution of particle sizes can be broad with a standard deviation of the average size of greater than 40%. The distribution of particle sizes can be narrow with a standard deviation of the average size of less than 30%. The final powdered or particulate form of the derivatized polyhydric polymer compositions of this disclosure can comprise a single distribution of average particle sizes or it can comprise two or more distributions of particles prepared by mixing particles of different average particle size.

A derivatized polyhydric polymer compositions of this disclosure can be formed into a solid form by preparing a solution of a derivatized polyhydric polymer in a solvent that can be removed, pouring this solution into a mold of a specific shape and then removing the solvent such that a solid form of derivatized polyhydric polymer composition is obtained. The molds used can be of various shapes and can include but are not limited to cubes, rectangles, rods, semi-circular rode and tubes. The solid derivatized polyhydric polymer composition of this disclosure can then be removed from the mold.

A derivatized polyhydric polymer composition of the disclosure can be processed into an electrospun matrix. In this process, a solution of the derivatized polyhydric polymer of the disclosure is prepared. The solvent used can be an organic solvent, water or a combination thereof. For example, for hyaluronic acid based derivatized polyhydric polymers, water/ethanol or water/dimethylformamide (DMF) solvent mixtures can be used. Solutions with a concentration of 0.5 to 5% (w/v) can be prepared. The solution that is to be electrospun can be placed in a syringe with a needle. The syringe is then placed in a syringe pump. The needle can have a blunt end and an inner diameter in the range of 0.25 to 1 mm. The needle and collection plate are attached to a high voltage supply. A voltage is then applied to the system. The applied voltage can be in the 10 kV to 45 kV. The syringe pump can extrude the solution. The flow rate of the syringe pump can be in the range of 10 uL/min to 1000 uL/min. The collector plate can be static, rotating or moving in a specific linear direction to give the fibers some directional orientation. The shape of the collector plate can be varied with the collector plate having but not limited to the following shapes: a flat surface, a textured surface, a curved surface, a square rod, a rectangular rod, a round mandrel, an oval mandrel, a semi-circular mandrel or a combination of these shapes. The temperature of the solution can be controlled as well as the collection plate and the surrounding environment. The distance of the needle tip to the collector plate can be altered. The distance of the needle tip to the collector plate can be in the 2-20 cm range. The collection plate can also be submerged in or sprayed with a solvent that assists in the precipitation of the newly spun fibers. For example, an ethanol bath may be used during the electrospinning of hyaluronic acid derivatized polyhydric polymers and/or compositions of this disclosure.

A derivatized polyhydric polymer of the disclosure can be incorporated through a solution coating or submersion of an electrospun matrix produced in the following manner. In this process, single or multiple polymer solutions are prepared. The polymers used can be biodegradable polymers then include but are not limited to polyester, polyanhydride, polyorthoester, polycarbonate, poly-ester-co-carbonate), polyhydroxybutyrates or combinations thereof. Biodegradable polymers can include polylactice-co-glycolide copolymers, polydioxanone, polylactide-trimethylene carbonate copolymers as well as copolymers that comprise repeat units derived from at least one of the following monomers: l-lactide, dl-lactide, glycolide, trimethylene carbonate, epsilon-caprolactone, p-dioxanone and a morpholinedione.

The solvents used can be an organic solvent, water or a combination thereof. For example, HFIP, DMSO, NMP, Chloroform, acetic acid, ethanol, dimethylformamide (DMF) solvents or mixtures of solvents can be used. Solutions with a concentration of 0.5 to 25% (w/v) can be prepared. The solution that is to be electrospun can be placed in a syringe with a needle. The syringe is then placed in a syringe pump. The needle can have a blunt end and an inner diameter in the range of 0.25 to 2.5 mm. The needle and collection plate are attached to a high voltage supply. A voltage is then applied to the system. The applied voltage can be in the 10 kV to 45 kV. The syringe pump can extrude the solution. The flow rate of the syringe pump can be in the range of 0.0001 uL/min to 423 mL/min. The collector plate can be static, rotating or moving in a specific linear direction to give the fibers some directional orientation. The shape of the collector plate can be varied with the collector plate having but not limited to the following shapes: a flat surface, a textured surface, a curved surface, a square rod, a rectangular rod, a round mandrel, an oval mandrel, a semi-circular mandrel or a combination of these shapes. The distance of the needle tip to the collector plate can be altered. The distance of the needle tip to the collector plate can be in the 2-50 cm range. The collection plate can also be submerged in or sprayed with a solvent that assists in the precipitation of the newly spun fibers. For example, an ethanol bath may be used during the electrospinning of hyaluronic acid based derivatized polyhydric polymers of this disclosure.

The derivatized polyhydric polymers and/or compositions of this disclosure can be processed into the form of a fiber. A solution of a derivatized polyhydric polymer of the disclosure is prepared. This solution is then extruded through an orifice to produce a solvent containing fiber. This fiber can be extruded into one or more solvent baths that assists in the formation of the fiber. The fiber is then dried to produce a solid fiber. The fibers can be prepared as a monofilament or a multifilament fiber. In one aspect, this fiber can then be further processed through an annealing step. U.S. Pat. Nos. 9,228,027, 5,520,916, 5,824,335, 8,389,498, US20130309494, US20150119783 describe exemplary methods to produce fibers from a polysaccharide. These are incorporated by reference as means to produce fibers from derivatized polyhydric polymers and/or compositions of this disclosure.

A fiber may be further processed by knitting or weaving, resulting in a knitted or woven composition. The knitted or woven composition can be in the form of a mesh. The mesh can comprise a single derivatized polyhydric polymer and/or composition of this disclosure. In another aspect, the mesh can comprise 2 or more different derivatized polyhydric polymers and/or compositions, of this disclosure. In another aspect, the fiber can be further processed into a braid. The braid can comprise a single derivatized polyhydric polymer and/or composition of this disclosure. In another aspect, the braid can comprise 2 or more different derivatized polyhydric polymers and/or compositions of this disclosure. For meshes or braids that use different derivatized polyhydric polymers and/or compositions of this disclosure, the derivatized polyhydric polymers and/or compositions used can result in the mesh or braid having properties that change as a function of time. This includes degradation rates, water absorption, elongation, elastic modulus, tensile strength, physical shape, lubricity, cell adhesion, or a combination of these properties.

The knitted, woven or braided derivatized polyhydric polymers and/or compositions can be manufactured in the presence of a degradable or non-degradable non-polysaccharide based material. These materials include polyethylene, polypropylene, polyethylene terephthalate (PET), polytetrafluorethylene (PTFE), nylon, polyurethane, polyester, polyanhydride, polyorthoester, polycarbonate, poly-ester-co-carbonate), polyhydroxybutyrates or combinations thereof.

Crosslinked polymers of the present disclosure may take various physical forms, including particle, film, lyophilized sponge, powder, particulate (e.g., milled, fragmented, precipitated and ground particulates), and may be formed in-situ, e.g., spray or liquid.

A film of crosslinked derivatized polyhydric polymers and/or compositions of this disclosure can be prepared by preparing a solution of the derivatized polyhydric polymer and/or compositions to be crosslinked. The derivatized polyhydric polymer can be crosslinked by known methods and/or those described herein. Prior to the final crosslinking process, the crosslinker is added, if required, and the solution pH can be adjusted to initiate the crosslinking process. This solution can be then placed in a mold or drawn out on a surface, for example, using a Gardner knife. The surface used can be glass, metal foil, stainless steel, Teflon, nylon, polyethylene or a release liner. The solution is then allowed to crosslink to form a gel. Heat can be applied to increase the rate of crosslinking. The solvent can then be removed to form the film.

A film of crosslinked derivatized polyhydric polymers of this disclosure can be prepared by preparing a solution of the derivatized polyhydric polymer to be crosslinked. The derivatized polyhydric polymer can be crosslinked by one of the methods described above. This solution can be then placed in a mold or drawn out on a surface using a Gardner knife. The surface used can be glass, metal foil, stainless steel, Teflon, nylon, polyethylene, polypropylene, polystyrene, or a release liner. The crosslinking agent may be added prior to or following drying of the derivatized polyhydric polymer to form a crosslinked film or gel. The rate of residual solvent removal can be altered by using at least one of the following parameters: temperature, air or inert gas flow and pressure. To increase the rate of solvent evaporation, the temperature could be increased, the air or inert gas flow rate could be increased or the pressure could be decreased. A combination of these process could also be used. To slow the rate of solvent evaporation, the temperature could be decreased, the air or inert gas flow rate could be reduced or the pressure could be increased. A combination of these process could also be used. A film can comprise one of the derivatized polyhydric polymers of this disclosure.

The films can also comprise two or more different derivatized polyhydric polymers of this disclosure. A composite film can be prepared by preparing a first film and then casting a second film on top of the first film. A composite film can be prepared by casting additional layers sequentially on top of the previous layer. The layers of the composite film can comprise the same derivatized polyhydric polymer if the disclosure, different derivatized polyhydric polymers of this disclosure or a combination thereof. The films can comprise both crosslinked and non-crosslinked derivatized polyhydric polymers of this disclosure.

Lyophilized forms of the crosslinked derivatized polyhydric polymers of this disclosure can be prepared by making a solution of the derivatized polyhydric polymer, crosslinking the derivatized polyhydric polymer, freezing the crosslinked derivatized polyhydric polymer composition and then placing the frozen derivatized polyhydric polymer composition under a vacuum such that the solvent is sublimed off to leave the resulting derivatized polyhydric polymer composition in the solid form. A lyophilized form of the derivatized polyhydric polymer of this disclosure can comprise one of the derivatized polyhydric polymers of this disclosure. In another aspect, the lyophilized form of the derivatized polyhydric polymer of this disclosure can comprise two or more different derivatized polyhydric polymers of this disclosure. The form of the lyophilized derivatized polyhydric polymer composition is dependent on the form of the container into which the solution was poured and frozen. The form can be a rectangle, square, disk, triangle, trapezoid, rod or any other form in which a mold can be made. The lyophilized derivatized polyhydric polymer compositions of this disclosure can comprise both crosslinked and non-crosslinked derivatized polyhydric polymers of this disclosure. In another aspect, the lyophilized derivatized polyhydric polymer composition, crosslinked or non-crosslinked, can be rehydrated in the presence of other materials disclosed herein. In another aspect, a second lyophilization step may be performed on a rehydrated derivatized polyhydric polymer composition.

In another aspect, the solution used to rehydrate the first lyophilized derivatized polyhydric polymer, can be crosslinked. In another aspect, the derivatized polyhydric polymer composition produced from the second crosslinking step can be lyophilized to produce a dry porous derivatized polyhydric polymer composition.

In another aspect, the derivatized polyhydric polymer solution may be directly combined with a biologically active agent prior to lyophilization. In another aspect, the lyophilized polyhydric polymer compositions may be combined with a biologically active agent through a rehydration process, which follows the first lyophilization, which may or may not be followed by further drying.

Crosslinked derivatized polyhydric polymer compositions of this disclosure can be in the form of a powder or particulate. A powder or particulate form can also be obtained through a milling, grinding, spray drying or fragmentation process. Films, precipitated derivatized polyhydric polymers and/or compositions, dried derivatized polyhydric polymers and/or compositions, lyophilized derivatized polyhydric polymer and/or compositions or derivatized polyhydric polymers and/or compositions in dried in a form can be further process via a milling process (jet milling, roller milling, cryomilling, mechanical milling), a grinding or a fragmentation process. A combination of these processes can be used. Derivatized polyhydric polymer compositions with particle size in the range of 100 nm to 5 mm can be prepared. Specific size ranges of the powdered or particulate derivatized polyhydric polymer compositions of this disclosure can be prepared by separating the derivatized polyhydric polymer compositions according to size using sieves. The distribution of particle sizes can be broad with a standard deviation of the average size of greater than 40%. The distribution of particle sizes can be narrow with a standard deviation of the average size of less than 30%. The final powdered or particulate form of the derivatized polyhydric polymers and/or compositions of this disclosure can comprise a single distribution of average particle sizes or it can comprise two or more distributions of particles prepared by mixing particles of different average particle size.

The crosslinked derivatized polyhydric polymers compositions of this disclosure can be formed into a solid form by preparing a solution of the derivatized polyhydric polymer in a solvent that can be removed, pouring this solution into a mold of a specific shape, crosslinking the derivatized polyhydric polymer in the mold, and then removing the solvent such that a solid form of the crosslinked derivatized polyhydric polymer composition is obtained. The molds used can be of various shapes and can include but are not limited to cubes, rectangles, rods, semi-circular rode and tubes. The solid derivatized polyhydric polymer composition of this disclosure can then be removed from the mold.

In one aspect, the derivatized polyhydric polymers of this disclosure can be used to prepare an in-situ gel forming composition. A derivatized polyhydric polymer of this disclosure that contains available vinyl sulfone groups can be reacted with a compound that contains at least two available free thiol groups or a compound that contains at least 2 available amine groups, preferably primary or secondary amines. Illustrative thiol containing compounds include PEG-dithiol (HS-PEG-SH), 3-arm PEG-tri-thiol (glycerine core), 4-arm PEG-tetrathiol (pentaerythritol core), or 8-arm PEG-octa-thiol (hexaglycerine core). The foregoing multi-armed PEG reagents may also have fewer than all arms functionalized with thiol. Additional suitable thiol reagents having PEG as the central molecule are available from Laysan Bio (Arab, Ala.), as well as aromatic dithiols such as those available from NanoScience. Other suitable thiol crosslinking agents include dimercaptosuccinic acid, 2,3-dimercapto-1-propanesulfonic acid, dihydrolipoic acid, peptides containing at least 2 cysteine amino acids, a thiol functionalized polysaccharide, thiol functionalized dextran, and thiol-functionalized hyaluronic acid. In one aspect, the derivatized polyhydric polymers of this invention can be prepared as a solution. This solution can be mixed with either a solution of the thiol containing compound or the solid form of the thiol containing compound to produce the gel composition.

The derivatized polyhydric polymers of the present disclosure, e.g., the first, second and third derivatives of a starting polymer, may be in combination with one or more other derivatized polyhydric polymers or other components, such as pharmaceutically acceptable excipients, or other known or common components of compositions. Thus, the present disclosure provides compositions comprising derivatized polyhydric polymers of the present disclosure.

The derivatized polyhydric polymers and compositions thereof of this disclosure can be used to treat living organisms. These living organisms include humans, animals, birds, fish, insects and plants. The derivatized polyhydric polymers and compositions thereof used in the indications described below can comprise, non-crosslinked derivatized polyhydric polymers, crosslinked derivatized polyhydric polymers or a combination thereof. In another aspect, the derivatized polyhydric polymer compositions used can comprise only one of the derivatized polyhydric polymers of this disclosure. In another aspect, the derivatized polyhydric polymer compositions used can comprise two or more of the derivatized polyhydric polymers of this disclosure. The derivatized polyhydric polymers and compositions thereof can further comprise one or more excipients. The derivatized polyhydric polymers and compositions thereof can further comprise one or more biologically active agents. The derivatized polyhydric polymers and compositions thereof that are used in the indications described below can be in a sterile form. Sterilization can be attained through sterile filtration, aseptic manufacture, gamma radiation, e-beam radiation, ethylene oxide, dry heat, autoclaving, or a combination thereof.

For instance, the derivatized polyhydric polymer compositions of this disclosure can also comprise an excipient. The excipient may be a pharmaceutically acceptable excipient. Excipients that can be used include but are not limited to natural polymers, synthetic polymers, thermosreversible polymers, biodegradable polymers, buffers, complexing agents, tonicity modulators, ionic strength modifiers, solvents, anti-oxidants, preservatives, viscosity modifiers, pH modifiers, surfactants, emulsifiers, phospholipids, stabilizers and porogens.

Excipient polymers that can be used include but are not limited to sodium alginate, calcium alginate, dextran, carboxymethyl cellulose, hydroxypropyl cellulose, hydroxypropyl methyl cellulose, methyl cellulose, hyaluronic acid, hyaluronic acid derivatives, dextran, heparin, chitosan, chitosan acetate, chitosan lactate, chitin, xantham gum, Xylan, guar gum, pullulan, locust bean gum, starch, gelatin, collagen, derivatized collagen, and acacia (gum Arabic).

Excipient degradable polymers that can be used include but are not limited to polyesters, polyether esters, polyorthoesters, poly ester carbonates, polycarbonates, polyanhydrides, polyhydroyalkonate (e.g. Polyhydroxybutyrate, polyhydroxyvalerates), polyurethanes, poly ester urethanes. The polymers can be in the form of linear, branched, or star shaped. The polymers can be initiated from compounds that us a single point of initiation, two points of initiation, 3 points of initiation, four points of initiation, 6 points of initiation or 8 points of initiation. Polymers can include but are not limited to polymers that are comprise repeat units derived from at least one of the following monomers: l-lactide, dl-lactide, glycolide, trimethylene carbonate, epsilon-caprolactone, p-dioxanone and a morpholinedione Excipient synthetic polymers that can be used include but are not limited to polyacrylic acid and salts thereof, polyvinylpyrollidone, Pluronics 127, pluronics F68, polyethylene glycol, polyethylene oxide, polyvinyl alcohol.

Complexing agents can include but are not limited to _α-cyclodextrin, _β-cyclodextrin (2-Hydroxypropyl)-Beta-Cyclodextrin, Sulfobutylether Beta Cyclodextrin Sodium, Ethylenediaminetetraacetic acid (EDTA)

Phospholipids that can be used include but are not limited to hydrogenated soy phosphatidylcholine, distearoylphosphatidylglycerol, L-α-dimyristoylphosphatidylcholine, L-α-dimyristoylphosphatidylglycerol Surfactants that can be used include ionic and non-ionic surfactants. Ionic surfactants can include cationic, anionic and zwitterionic surfactants. Non-ionic surfactants can include but are not limited to (Cremophor EL, Cremophor RH 40, Cremophor RH 60, d-_-tocopherol polyethylene glycol 1000 succinate, Brij, Myrj, polysorbate 20, polysorbate 80, polysorbate 40, polysorbate 60, polysorbate 65, polysorbate 85, Solutol HS 15, sorbitan monooleate (Span 80), Sorbitan monopalmitate (Span 40), sorbitan monostearate (Span 60), sorbitan trioleate (Span 8) poloxamer 407, Labrafil M-1944CS, Labrafil M-2125CS, Labrasol, Gellucire 44/14, nonoxynol-9, Softigen 767, octyl beta-D-glycopyranoside (OGP), hexyl beta-D-glucopyranoside (HGP), Octyl beta-D-1-thioglucopyranoside (TGP), Decyl-beta-D-glucopyranoside (DGP), Dodecyl-beta-D-glucopyranoside (DdGP), N-octyl beta-D-Maltoside (ODM), decyl beta-D-maltopyranoside (DMP), cyclohexyl-ethanoyl-maltoside, n-decyl- and n-dodecyl-sucrose, and mono- and di-fatty acid esters of PEG 300, 400, or 1750. Anionic surfactants can include but are not limited to sodium lauryl sulfate, fatty acid salts, sodium laureth sulfate, dioctyl sodium sulfosuccinate. Cationic surfactants can include but are not limited to Phosphatidylcholine (Lecithin), cetrimide, cetrimonium bromide, benethonium chloride, dimethyldioctadecyl ammonium chloride, tetradecyl trimethyl ammonium bromide, cetylpyridinium chloride, esterquat, and benzalkonium chloride. Zwiterionic surfactants can include but are not limited to Cocamidopropyl betaine, (3-[(3-Cholamidopropyl)dimethylammonio]-1-propanesulfonate) and cocamidopropyl hydroxysultaine, phosphatidylserine, phosphatidylethanolamine, phosphatidylcholine, and sphingomyelins.

Solvents that can be used include water-soluble organic solvents. Water-soluble organic solvents include but are not limited to polyethylene glycol 200, polyethylene glycol 300, polyethylene glycol 400, ethanol, propylene glycol, glycerin, N-methyl-2-pyrrolidone, dimethylacetamide, and dimethylsulfoxide.

Tonicity modifiers that can be used include but are not limited to dextrose, sucrose, mannitol, glycerin, sodium chloride, and potassium chloride.

pH modifiers that can be used include but are not limited to citric acid and its salts, salts of phosphoric acid, tartatic acid, lactic acid, glycolic acid, sodium hydroxide, phosphoric acid, sulfuric acid, oxalic acid and hydrochloric acid.

Anti-oxidants that can be used include but are not limited to ascorbic acid, butylated hydroxyanisole, Butylhydroxytoluene, Vitamin A, vitamin E, α-tocopherol, thioglycerol, cysteine, acetylcysteine, cystine, dithioerythreitol, dithiothreitol, glutathione, Sodium bisulfite, Sodium metabisulfite, thiourea, uric acid, melatonin, propyl gallate, tertiary butylhydroquinone and combinations thereof.

Emulsifiers that can be used include but are not limited to Glyceryl Monostearate, Isopropyl Palmitate, Polyethylene Glycol 400 Monostearate, as well as the compounds listed as surfactants and combinations thereof.

Preservatives that can be used include but are not limited to benzoic acid, sorbic acid, boric acid, methylparaben, ethylparaben, propylparaben, butylparaben, sodium benzoate, sodium propionate, phenyl ethyl alcohol, chlorobutanol, benzyl alcohol, potassium sorbate, phenol, chlorocresol, o-phenyl phenol, thiomersal, nitromersol, phenylmercuric nitrate, phenylmercuric acetate, benzalkonium and combinations thereof.

The excipients can include at least one solvent. The solvents used can include but are not limited to water, ethanol, dimethylsulfoxide, ethyl lactate, ethyl acetate, benzyl alcohol, benzyl benzoate, triacetin, N-methylpyrrolidone, 2-pyrrolidone, propylene carbonate, polyethylene glycol (PEG200), polyethylene glycol (PEG400), glycofurol and combinations thereof.

Buffers that can be used include aqueous solutions prepared using one or more of the following: potassium hydrogen phthalate, sodium hydrogen phthalate, potassium or sodium dihydrogen phosphate, dipotassium or disodium hydrogen phosphate, phosphoric acid, boric acid, sodium acetate, acetic acid, ammonium chloride, ammonium acetate, (4-(2-hydroxyethyl)-1-piperazineethanesulfonic acid), citric acid and sodium citrate.

In another aspect, the derivatized polyhydric polymer compositions of this disclosure can further comprise an inorganic compound. The inorganic compounds that can be used include but are not limited to barium sulfate, calcium hydroxylapatite or hydroxyapatite, tricalcium phosphate (TCP) [including the various forms, for example α-TCP, β-TCP, and Biphasic Tricalcium Phosphate (BCP)], calcium phosphate and calcium sulphate.

In one aspect, the derivatized polyhydric polymers of this disclosure can be prepared as a composition that comprises one or more excipients. In another aspect, the derivatized polyhydric polymers of this disclosure can be suspended in a composition that comprises one or more excipients. In another aspect, the derivatized polyhydric polymers of this disclosure can be rehydrated in a composition that comprises one or more excipients. In another aspect, the derivatized polyhydric polymers of this disclosure can be prepared as separate compositions that can comprise one or more excipients with the separate solutions being mixed prior to use. In another aspect, the derivatized polyhydric polymers of this disclosure can be prepared in the presence of one or more excipients and then converted to a solid form by one or more of the methods described in this disclosure.

Compositions of the present disclosure may comprise a biologically active agent in addition to a derivatized polyhydric polymer as described herein and optionally other components. Exemplary biologically active agents include, without limitation, small molecule drugs, peptides, proteins, growth factors, hormones, antibodies, agonists, antagonists, anti-bacterial and/or anti-fungal agents.

Biologically active agents that can be incorporated into formulations with the compositions described include: antiandrogens, antibacterial, antioestrogens, androgens and anabolic agents, antibiotics, antimigraine drugs, antihistamines, antianxiety drugs, antidiuretics, antihistamines, antirheumatoid agents, antigens, analgesics, antidepressants, antiinflammatories, anesthetics, aminoglycosides antibodies, antiviral, adrenergic stimulants, anticonvulsants, antiangina agents, antiarrhyrthmics, antimalarials, anti-mitotic, anthelmintics, anoretic agents, antitussives, antipruritics, antipyretics, anti-alzheimer's agents, anti-Parkinson's agents, antiemetics and antinauseants, antihypertensives, anticoagulants, antifungals, antimicrobials, allergens, antidiarrheals, antihyperuricaemia agents, adrenergic stimulants, antiparasitic agents, antiproliferative agents, antipsychotic drugs, antithyroid agents, beta-adrenergic blocking agents, bronchodilators; bronchospasm relaxants, blood clotting factors, blood coagulation factors, cytotoxic agents, cytostatic agents, chemotherapeutics, clot inhibitors, clot dissolving agents, cells, CNS stimulants, Corticosteroids, calcium channel blockers, cofactors, ceramides, cardiotonic glycosides, cytokines (e.g., lymphokines, monokines, chemokines); colony stimulating factors (e.g., GCSF, GM-CSF, MCSF); dermatological agents, decongestants, diuretics, expectorants, endectocide agents, growth factors, hemostatic agents, hypoglycemic agents, hormones and hormone analogs, hypercalcemia, Hypnotics, interleukins (IL-2, IL-3, IL-4, IL-6); interferons (.beta.-IFN, .alpha.-IFN and .gamma.-IFN); immunosuppressants, muscle relaxants, microorganisms, non-steroidal anti-inflammatory agents, nucleic acids, nutritional agents, neuromuscular blocking agents, neuroleptics, Neurotoxins, nutraceuticals, oligonucleotides, oestrogens, obstetric drugs, ovulation inducers, opioids, progestogens, pituitary hormones, Pituitary inhibitors proteins, peptides, polysaccharides, protease inhibitors, prostaglandins, quinolones, reductase inhibitors, sulfa drugs, sclerosant, sedatives, sodium channel blockers, steroids, steroidal anti-inflammatory agents, smoking cessation agents, toxins, thrombolytic agents, thyroid hormones, tumor necrosis factor; vesicles, vitamins, viruses, vasodilators, vaccines Additional representative examples of biologically active agents that may be suitable for use in the compositions of the present disclosure include, but are not limited to: Antidiarrheals such as diphenoxylate, loperamide and hyoscyamine; Antihypertensives such as hydralazine, minoxidil, captopril, enalapril, clonidine, prazosin, debrisoquine, diazoxide, guanethidine, methyldopa, reserpine, trimethaphan; Calcium channel blockers such as diltiazem, felodipine, amlodipine, nitrendipine, nifedipine and verapamil; Antiarrhythmics such as amiodarone, flecainide, disopyramide, procainamide, mexiletene and quinidine, Antiangina agents such as glyceryl trinitrate, erythrityl tetranitrate, pentaerythritol tetranitrate, mannitol hexanitrate, perhexilene, isosorbide dinitrate and nicorandil; Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate; Cardiotonic glycosides such as digoxin and other cardiac glycosides and theophylline derivatives; Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine; Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol; Antiproliferative agents such as paclitaxel, estradiol, actinomycin D, sirolimus, tacrolimus, everolimus, 5-fluorouracil and dexamethasone; Antimigraine preparations such as ergotanmine, dihydroergotamine, methysergide, pizotifen and sumatriptan; Anticoagulants and thrombolytic agents such as warfarin, dicoumarol, low molecular weight heparins such as enoxaparin, streptokinase and its active derivatives; Hemostatic agents such as aprotinin, tranexamic acid and protamine; Analgesics and antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine, dihydrocodeine; acetylsalicylic acid (aspirin), paracetamol, synthetic alpha2-adrenoreceptor agonist, dexmedetomidine hydrochloride, flunixin meglumine, meperidine, phenylbutazone and phenazone; Immunosuppressants, antiproliferatives and cytostatic agents such as rapamycin (sirolimus) and its analogs (everolimus and tacrolimus); Neurotoxins such as capsaicin, botulinum toxin (botox); Hypnotics and sedatives such as the barbiturates amylobarbitone, butobarbitone and pentobarbitone and other hypnotics and sedatives such as chloral hydrate, chlormethiazole, hydroxyzine and meprobamate; Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam; Neuroleptic and antipsychotic drugs such as the phenothiazines, chlorpromazine, fluphenazine, pericyazine, perphenazine, promazine, thiopropazate, thioridazine, trifluoperazine; and butyrophenone, droperidol and haloperidol; and other antipsychotic drugs such as pimozide, thiothixene and lithium; Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline; CNS stimulants such as caffeine and 3-(2-aminobutyl) indole; Antipruritics can include compounds such as synthetic Janus Kinase (JAK) inhibitors, NK-1 receptor antagonists, antibodies that neutralize interleukin-31 (IL-31). These can include oclacitinib maleate, Serlopitant, and Lokivetmab, Anti-alzheimer's agents such as tacrine; Anti-Parkinson's agents such as amantadine, benserazide, carbidopa, levodopa, benztropine, biperiden, benzhexol, procyclidine and dopamine-2 agonists such as S (−)-2-(N-propyl-N-2-thienylethylamino)-5-hydroxytetralin (N-0923), Anticonvulsants such as phenytoin, valproic acid, primidone, phenobarbitone, methylphenobarbitone and carbamazepine, ethosuximide, methsuximide, phensuximide, sulthiame and clonazepam, Antiemetics and antinauseants such as the phenothiazines prochloperazine, thiethylperazine, a neurokinin (NK1) receptor antagonist, maropitant citrateand 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and brompride; Non-steroidal anti-inflammatory agents including their racemic mixtures or individual enantiomers where applicable, preferably which can be formulated in combination with dermal and/or mucosal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, 6-chloro-α-methyl-9H-carbazole-2-acetic acid (carprofen), flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate; Antirheumatoid agents such as penicillamine, aurothioglucose, sodium aurothiomalate, methotrexate and auranofin; Muscle relaxants such as baclofen, diazepam, cyclobenzaprine hydrochloride, dantrolene, methocarbamol, orphenadrine and quinine; Agents used in gout and hyperuricaemia such as allopurinol, colchicine, probenecid and sulphinpyrazone; Oestrogens such as estradiol, oestriol, estrone, ethinylestradiol, mestranol, stilbestrol, dienestrol, epiestriol, estropipate and zeranol; Progesterone and other progestagens such as allylestrenol, dydrgesterone, lynestrenol, norgestrel, norethyndrel, norethisterone, norethisterone acetate, gestodene, levonorgestrel, medroxyprogesterone and megestrol; Antiandrogens such as cyproterone acetate and danazol; Antioestrogens such as tamoxifen and epitiostanol and the aromatase inhibitors, exemestane and 4-hydroxy-androstenedione and its derivatives; Androgens and anabolic agents such as testosterone, methyltestosterone, clostebol acetate, drostanolone, furazabol, nandrolone oxandrolone, stanozolol, trenbolone acetate, dihydro-testosterone, 17-(.alpha.-methyl-19-noriestosterone and fluoxymesterone; 5-alpha reductase inhibitors such as finasteride, turosteride, LY-191704 and MK-306; Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide; Glycosylated proteins, proteoglycans, glycosaminoglycans such as chondroitin sulfate; chitin, acetyl-glucosamine, hyaluronic acid; Complex carbohydrates such as glucans; Further examples of steroidal anti-inflammatory agents such as cortodoxone, fludroracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone, aincinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol; Pituitary hormones and their active derivatives or analogs such as corticotrophin, thyrotropin, follicle stimulating hormone (FSH), a Gonadotropin-releasing hormone (GnRH) analog, u deslorelin acetate, cetrorelix acetate, Gonadorelin acetate, clomiphene, Human chorionic gonadotropin (HCG), luteinizing hormone (LH) and gonadotrophin releasing hormone (GnRH); Hypoglycemic agents such as insulin, chlorpropamide, glibenclamide, gliclazide, glipizide, tolazamide, tolbutamide and metformin; Thyroid hormones such as calcitonin, thyroxine and liothyronine and antithyroid agents such as carbimazole and propylthiouracil; Other miscellaneous hormone agents such as octreotide; Pituitary inhibitors such as bromocriptine; Ovulation inducers such as clomiphene; Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potassium sparing diuretics, spironolactone, amiloride and triamterene; Antidiuretics such as desmopressin, lypressin and vasopressin including their active derivatives or analogs; Obstetric drugs including agents acting on the uterus such as ergometrine, oxytocin and gemeprost; Prostaglandins such as alprostadil (PGE1), prostacyclin (PGI2), dinoprost (prostaglandin F2-alpha) and misoprostol; Antimicrobials including the cephalosporins such as cephalexin, cefoxytin and cephalothin; Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin; Tetracyclines such as minocycline, chlortetracycline, tetracycline, demeclocycline, doxycycline, methacycline and oxytetracycline and other tetracycline-type antibiotics; Amnioglycoides such as amikacin, amikin sulfate, gentamicin, kanamycin, neomycin, netilmicin and tobramycin; Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione; Quinolones such as nalidixic acid, cinoxacin, ciprofloxacin, enoxacin and norfloxacin; Sulphonamides such as phthalysulphthiazole, sulfadoxine, sulphadiazine, sulphamethizole and sulphamethoxazole; Sulphones such as dapsone; Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, tinidazole, secnidazole, ornidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds, silver sulfadiazine, silver, nanoparticulate silver, silver nitrate, silver zeolites, silver cations, AgPO3 Ag3PO4, Ag4P2O7, Exsalt® SD7 (Exciton Technologies) Exsalt® T7 (Exciton Technologies); Lincomycin Hydrochloride, tricyclic tetrahydroquinoline antibacterial agents, 8-pyrazinyl-S-spiropyrimidinetrione-oxazinoquinoline derivatives, 3-spiropyrimidinetrione-quinoline derivatives, thiadiazolspiropyrimidinetrione-quinoline derivatives, (2R,4S,4aS)-10-fluoro-2,4-dimethyl-8-(4-methyloxazol-2-yl)-2,4,4a,6-tetra-hydro-1H,1'H-spiro[[1,4]oxazino[4,3-a]quinoline-5,5'-pyrimidine]-2',4',6'(−3'H)-trione, (2R,4S,4aS)-9,10-difluoro-2,4-dimethyl-8-(3-methylisoxazol-5-yl)-2,4,4a,6-tetrahydro-1H,1'H-spiro[[1,4]oxazino[4,3-a]quinoline-5,5'-pyrimidine]-2',-4',6'(3'H)-trione, (2R,4S,4aS)-10-fluoro-2, 4-dimethyl-8-(oxazol-2-yl)-2,4,4a,6-tetra hydro-1H-,1'H-spiro[[1,4]oxazino[4,3-a]quinoline-5,5'-pyrimidine]-2',4',6' (3'H)-tri-one, (2R,4S,4aS)-9,10-difluoro-2,4-dimethyl-8-(2-methyloxazol-5-yl)-2,4,4a,6-tetrahydro-1H,1'H-spiro[[1,4] oxazino[4,3-a]quinoline-5,5'-pyrimidine]-2',4'-,6'(3'H)-trione, (2R,4S,4aS)-9,10-difluoro-2,4-dimethyl-8-(oxazol-4-yl)-2,4,4a,6-tetrahydr-o-1H,1'H-spiro[[1,4]oxazino[4,3-a] quinoline-5,5'-pyrimidine]-2',4',6T(TH)-trione, (2R,4S, 4aS)-9-fluoro-2,4-dimethyl-8-(4-methyloxazol-2-yl)-2,4,4a, 6-tetrah-ydro-1H,1'H-spiro[[1,4]oxazino[4,3-a]quinoline-5, 5'-pyrimidine]-2',4',6'(3-'H)-trione, (2R,4S,4aS)-9,10-difluoro-8-(4-(4-fluorophenyl)oxazol-5-yl)-2,4-dimethyl-2,4, 4a,6-tetrahydro-1H,1'H-spiro[[1,4]oxazino[4,3-a]quinoline-5,5'-pyrimid-ine]-2',4',6'(3'H)-trione, (2S,4R,4a R)-2,4-dimethyl-8-(oxazol-5-yl)-2,4,4a,6-tetra hydro-1H, VH-spiro-[[1,4]oxazino[4,3-a]quinoline-5,5'-pyrimidine]-2',4',6'(3'H)-trione, (2S,4R,4aR)-8-(4-ethyloxazol-2-yl)-9, 10-difluoro-2,4-dimethyl-2,4,4a,6-te-trahydro-1H,1'H-spiro [[1,4]oxazino[4,3-a]quinoline-5,5'-pyrimidine]-2',4',-6' (3'H)-trione, (2R,4S,4aS)-9,10-difluoro-2,4-dimethyl-8-(oxazol-2-yl)-2,4,4a,6-tetrahydr-o-1H,1'H-spiro[[1,4] oxazino[4,3-a]quinoline-5,5'-pyrimidine]-2',4',6'(3'H)-trione, benzoyl peroxide; Antituberculosis drugs such as ethambutol, isoniazid, pyrazinamide, rifampicin and clofazimine; Antimalarials such as primaquine, pyrimethamine, chloroquine, hydroxychloroquine, quinine, mefloquine and halofantrine; compounds such as Azithromycin, Aztreonam, Cefaclor, Cefadroxil, Cefazolin, Cefdinir, Cefepime Hydrochloride, (cefoperazone sodium, Ceftaroline fosamil, avibactam, Ceftazidime sodium, Ceftibuten, ceftiofur, Tazobactam, cefovecin sodium [(6R,7R)-7-[[(2Z)-(2-amino-4-thiazolyl)(methoxyimino)acetyl]amino]-8-oxo-3-[(2S)-tetrahydro-2-furanyl]-5-thia-1-azabicyclo[4.2.0]oct-2-ene-2-carboxylic acid, monosodium salt] Cefuroxime Axetil, Cefuroxime, Cephalexin, Chloramphenicol Sodium, Ciprofloxacin HCl, Clarithromycin, Clindamycin hydrochloride, Clindamycin Palmitate hydrochloride, Clindamycin phosphate, Dalbavancin Hydrochloride, Daptomycin, Demeclocycline hydrochloride, Dicloxacillin, Doripenem, Doxycycline, Doxycycline calcium, Doxycycline hyclate, Doxycycline monohydrate, Ertapenem sodium, Erythromycin, Erythromycin Ethylsuccinate, Erythromycin lactobionate, Erythromycin stearate, Erythromycin, Fosfomycin tromethamine, Gemifloxacin mesylate, Gentamicin Sulfate, Imipenem, Kanamycin, Levofloxacin, Lincomycin hydrochloride, Linezolid, Meropenem, Methenamine Hippurate, Metronidazole, Metronidazole, Micafungin sodium, Minocycline Hydrochloride, Minocycline, Moxifloxacin hydrochloride, Nafcillin, Nalidixic acid, Neomycin Sulfate, Nitrofurantoin, Norfloxacin, Ofloxacin, Oritavancin diphosphate, Oxacillin, Penicillin G, Penicillin G benzathine, Penicillin G Sodium, Penicillin V Potassium, Piperacillin Sodium, Polymyxin B Sulfate, Quinupristin, dalfopristin, Spectinomycin hydrochloride, Streptomycin, Sulfamethoxazole, Tedizolid Phosphate, Telavancin, Telithromycin, Tetracycline Hydrochloride, Ticarcillin disodium, Tigecycline, Tobramycin Sulfate, Tobramycin, Trimethoprim hydrochloride, tulathromycin, Vancomycin hydrochloride.

Antiviral agents may be included in the compositions of the present disclosure, where exemplary antiviral agents include acyclovir and acyclovir prodrugs, famcyclovir, zidovudine, didanosine, stavudine, lamivudine, zalcitabine, saquinavir, indinavir, ritonavir, n-docosanol, tromantadine and idoxuridine. Other suitable biologically active agents include Anthelmintics such as mebendazole, thiabendazole, niclosamide, praziquantel, pyrantel embonate and diethylcarbamazine; Cytotoxic agents such as plicamycin, cyclophosphamide, dacarbazine, fluorouracil and its prodrugs (described, for example, in International Journal of Pharmaceutics, 111, 223-233 (1994)), methotrexate, procarbazine, 6-mercaptopurine and mucophenolic acid; Anorectic and weight reducing agents including dexfenfluramine, fenfluramine, diethylpropion, mazindol and phentermine; Agents used in hypercalcaemia such as calcitriol, dihydrotachysterol and their active derivatives or analogs; Antitussives such as ethylmorphine, dextromethorphan and pholcodine; Antiparasitic and Endectocide agents such as moxidectin, Ivermectin, Niclosamide, Praziquantel, Pyrantel, Pyrvinium, Albendazole, Flubendazole, Mebendazole, Thiabendazole Compositions of the present disclosure may include: an expectorant such as carbolcysteine, bromihexine, emetine, quanifesin, ipecacuanha and saponins; Decongestants such as phenylephrine, phenylpropanolamine and pseudoephedrine; Bronchospasm relaxants such as ephedrine, fenoterol, orciprenaline, rimiterol, salbutamol, sodium cromoglycate, cromoglycic acid and its prodrugs (described, for example, in International Journal of Pharmaceutics 7, 63-75 (1980)), terbutaline, ipratropium bromide, salmeterol and theophylline and theophylline derivatives; Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine; Local anaesthetics such as benzocaine, bupivacaine, amethocaine, lignocaine, lidocaine, cocaine, cinchocaine, dibucaine, mepivacaine, prilocaine, etidocaine, veratridine (specific c-fiber blocker) and procaine; Stratum corneum lipids, such as ceramides, cholesterol and free fatty acids, for improved skin barrier repair [Man, et al. J. Invest. Dermatol., 106(5), 1096, (1996)]; Neuromuscular blocking agents such as suxamethonium, alcuronium, pancuronium, atracurium, gallamine, tubocurarine and vecuronium; sclerocing agents or sclerosants may be a surfactant or it may be selected from the group consisting of ethanol, dimethyl sulfoxide, sucrose, sodium chloride, dextrose, glycerin, minocycline, tetracycline, doxycycline, polidocanol, sodium tetradecyl sulfate, sodium morrhuate, and sotradecol. an angiogenesis inhibitor; a 5-lipoxygenase inhibitor or antagonist; a chemokine receptor antagonist; a cell cycle inhibitor; a taxane; an anti-microtubule agent; paclitaxel; an analogue or derivative of paclitaxel; a vinca alkaloid; camptothecin or an analogue or derivative thereof; a podophyllotoxin, wherein the podophyllotoxin may be an etoposide or an analogue or derivative thereof; an anthracycline, wherein the anthracycline may be doxorubicin or an analogue or derivative thereof or the anthracycline may be mitoxantrone or an analogue or derivative thereof; a platinum compound; a nitrosourea; a nitroimidazole; a folic acid antagonist; a cytidine analogue; a pyrimidine analogue; a fluoropyrimidine analogue; a purine analogue; a nitrogen mustard or an analogue or derivative thereof; a hydroxyurea; a mytomicin or an analogue or derivative thereof; an alkyl sulfonate; a benzamide or an analogue or derivative thereof; a nicotinamide or an analogue or derivative thereof; a halogenated sugar or an analogue or derivative thereof; a DNA alkylating agent; an anti-microtubule agent; a topoisomerase inhibitor; a DNA cleaving agent; an antimetabolite; a nucleotide interconversion inhibitor; a hydroorotate dehydrogenase inhibitor; a DNA intercalation agent; an RNA synthesis inhibitor; a pyrimidine synthesis inhibitor; a cyclin dependent protein kinase inhibitor; an epidermal growth factor kinase inhibitor; an elastase inhibitor; a factor Xa inhibitor; a farnesyl-transferase inhibitor; a fibrinogen antagonist; a guanylate cyclase stimulant; a heat shock protein 90 antagonist; which may be a geldanamycin or an analogue or derivative thereof; a guanylate cyclase stimulant; a HMGCoA reductase inhibitor, which may be simvastatin or an analogue or derivative thereof; an IKK2 inhibitor; an IL-1 antagonist; an ICE antagonist; an IRAK antagonist; an IL-4 agonist; an immunomodulatory agent; sirolimus or an analogue or derivative thereof; everolimus or an analogue or derivative thereof; tacrolimus or an analogue or derivative thereof; biolmus or an analogue or derivative thereof; tresperimus or an analogue or derivative thereof; auranofin or an analogue or derivative thereof; 27-0-demethylrapamycin or an analogue or derivative thereof; gusperimus or an analogue or derivative thereof; pimecrolimus or an analogue or derivative thereof; ABT-578 or an analogue or derivative thereof; an inosine monophosphate dehydrogenase (IMPDH) inhibitor, which may be mycophenolic acid or an analogue or derivative thereof or 1-.alpha.-25 dihydroxy vitamin D.sub.3 or an analogue or derivative thereof; a leukotriene inhibitor; an MCP-1 antagonist; an MMP inhibitor; an NF kappa B inhibitor, which may be Bay 11-7082; an NO antagonist; a p38 MAP kinase inhibitor, which may be SB 202190; a phosphodiesterase inhibitor; a TGF-.beta. inhibitor; a thromboxane A2 antagonist; a TNF-alpha-antagonist; a TACE inhibitor; a tyrosine kinase inhibitor; vitronectin inhibitor; a fibroblast growth factor inhibitor; a protein kinase inhibitor; a PDGF receptor kinase inhibitor; an endothelial growth factor receptor kinase inhibitor; a retinoic acid receptor antagonist; a platelet derived growth factor receptor kinase inhibitor; a fibrinogen antagonist; an antimycotic agent; sulconizole; a bisphosphonate; a phospholipase A1 inhibitor; a histamine H1/H2/H3 receptor antagonist; a macrolide antibiotic; a GPIIb/IIIa receptor antagonist; an endothelin receptor antagonist; a peroxisome proliferator-activated receptor agonist; an estrogen receptor agent; a somastostatin analogue; a neurokinin 1 antagonist; a neurokinin 3 antagonist; a VLA-4 antagonist; an osteoclast inhibitor; a DNA topoisomerase ATP hydrolyzing inhibitor; an angiotensin I converting enzyme inhibitor; an angiotensin II antagonist; an enkephalinase inhibitor; a peroxisome proliferator-activated receptor gamma agonist insulin sensitizer; a protein kinase C inhibitor; a ROCK (rho-associated kinase) inhibitor; a CXCR3 inhibitor; Itk inhibitor; a cytosolic phospholipase A.sub.2-.alpha. inhibitor; a PPAR agonist; an immunosuppressant; an Erb inhibitor; an apoptosis agonist; a lipocortin agonist; a VCAM-1 antagonist; a collagen antagonist; an .alpha.-2 integrin antagonist; a TNF-.alpha. inhibitor; a nitric oxide inhibitor; and a cathepsin inhibitor. anti-fibrin and fibrinolytic agents, including plasmin, streptokinase, single chain urokinase, urokinase, t-PA (tissue type plasminogen activator), aminocaproic acid; anti-platelet agents including, aspirin, prostacyclins (and analogues); glycoprotein IIb/IIIa agents including monoclonal antibodies, peptides (e.g. ReoPro, Cilastagel, eptifibatide, tirofiban, ticlopidine, Vapiprost, dipyridamole, forskolin, angiopeptin, argatroban), thromboxane inhibitors; anti-thrombin and anticoagulant agents, including dextan, heparin, LMW heparin (Enoxaparin, Dalteparin), hirudin, recombinant hirudin, anti-thrombin, synthetic antithrombins, thrombin inhibitors, Warfarin (and other coumarins); anti-mitotic, antiproliferative and cytostatic agents, including vincristine, vinblastine, paclitaxel, methotrexate, cisplatin, fluorouracil, rapamycin, azathioprine, cyclophosphamide, mycophenolic acid, corticosteroids, colchicine, nitroprusside; antiangiogenic and angiostatic agents, including paclitaxel, angiostatin and endostatin; genetic materials, DNA, DNA sequences, polynucleotides, and oligonucleotides; ACE inhibitors (e.g. Cilazapril, Lisinopril, Captopril); growth factor (e.g. VEGF, FGF) antagonists; antioxidants and vitamins (e.g. Probucol, Tocopherol); calcium channel blockers (e.g. nifedipine); fish oil (omega 3-fatty acid); phosphodiesterase inhibitors (e.g. dipyridamole); nitric acid donor (e.g. Molsidomine); somatostatin analogues (e.g. angiopeptin); immunosuppresives and anti-inflammatory agents (e.g. prednisolone, glucocorticoid and dexamethasone); antimicrobials (e.g. rifamycin) and radionuclides, including alpha, beta and gamma emitting isotopes (e.g. Re-188, Re-186, 1-125, Y-90); COX-2 inhibitors such as Celecoxib and Vioxx; kinase inhibitors, such as epidermal growth factor kinase inhibitor, tyrosine kinase inhibitors, MAP kinase inhibitors protein transferase inhibitors, Resten-NG, smoking cessation agents such as nicotine, bupropion and ibogaine; Insecticides and other pesticides which are suitable for local application; Dermatological agents, such as vitamins A, C, B1, B2, B6, B 12, B 12.alpha., and E, vitamin E acetate and vitamin E sorbate; Allergens for desensitisation such as house, dust or mite allergens; Nutritional agents and neutraceuticals, such as vitamins, essential amino acids and fats; Macromolecular pharmacologically active agents such as proteins, enzymes, peptides, polysaccharides (such as cellulose, amylose, dextran, chitin), nucleic acids, cells, tissues, and the like; Bone mending biochemicals such as calcium carbonate, calcium phosphate, tricalcium phosphate, hydroxyapetite or bone morphogenic protein (BMP); Angiogenic growth factors such as Vascular Endothelial Growth Factor (VEGF) and epidermal growth factor (EFG), cytokines interleukins, fibroblasts and cytotaxic chemicals; and Keratolytics such as the alpha-hydroxy acids, glycolic acid and salicylic acid; and DNA, RNA or other oligonucleotides. Vaccines that contain Hendra virus (HeV) G glycoprotein and/or Nipah virus G glycoprotein, Lutenising Hormone Releasing Hormone (LHRH) peptide, LHRH-diphtheria toxoid conjugate, porcine circovirus type 2 (PCV2) antigen, a porcine reproductive and respiratory syndrome virus antigen, *Mycoplasma* hyopneumoniae protein antigen. Proteins or protein fragments, for example ORFI Torque teno virus protein, or other TTV proteins or fragments, antigens against *Aeromonas salmonicida*, antigens against *Vibrio anguillarum*, and antigens against *V. salmonicida*. Growth factors include but are not limited to Vascular Endothelial Growth Factor (VEGF) and epidermal growth factor (EFG), Growth Differentiation Factors (GDFs), Fibroblast Growth Factors (FGF-1 through FGF-23), Osteoprotegerin, Cartilage Derived Morphogenic Proteins (CDMPs, which can be a foundation for soft or hard tissue), Lim Mineralization Proteins (LMPs)Interleukins (IL-1 through IL-13), Insulin-like Growth Factor-1, Connective Tissue Growth Factor (CTGF), platelet derived growth factor (PDGF), nerve growth factors, neutrophins Brain-derived neurotrophic factor (BDNF), Nerve growth factor (NGF), Neurotrophin-3 (NT-3), Neurotrophin-4 (NT-4)], Transforming growth factors (TGF-$\alpha$, TGF-$\beta$), Tumor necrosis factor (TNF). Growth factor Agonists or antagonists as well as antibodies against these growth factors. Biologically active agents that can be used to treat macular degeneration include but are not limited to bevacizumab and ranibizumab In one aspect, compositions of the present disclosure are formulated for, and are useful for, wound healing. Compositions may be formulated for suitable administration, e.g., nasal or topical administration. Compositions may include one or more suitable biologically active agents for wound healing. The wounds treated can include but are not limited to diabetic ulcers, burns, pressure wounds, abrasions, incisions, corneal abrasion, incisions following ocular surgery, blisters, damaged tissue following sinus surgery, abdominal surgery, tendon repair or joint repair.

For example, in one aspect, derivatized polyhydric polymer compositions of the disclosure can be in the form of dry particles. In another aspect, the derivatized polyhydric polymer compositions of the disclosure can be in the form of a lyophilized derivatized polyhydric polymer compositions.

In another aspect, the derivatized polyhydric polymer compositions of the disclosure can be on the form of a non-woven derivatized polyhydric polymer compositions. In one aspect, the non-woven derivatized polyhydric polymer compositions can be produced by an electrospinning process. In another aspect, the derivatized polyhydric polymer of the disclosure can be in the form of a film. Compositions can be packaged directly or indirectly in a foil pouch to minimize moisture absorption during storage.

Derivatized polyhydric polymer compositions of the disclosure can be applied directly to a wound site. The derivatized polyhydric polymer compositions can absorb exudate from the wound. Once sufficient exudate is absorbed, the dry derivatized polyhydric polymer compositions will turn into a gel. In another aspect, the derivatized polyhydric polymer compositions of the disclosure further comprise water or saline such that a gel is obtained. In one aspect, the gel can be applied directly to the wound.

In one aspect, the derivatized polyhydric polymer compositions of the disclosure, once applied to the wound, can be covered by a have a moisture retaining semi-permeable film. The film can further comprise an adhesive that will retain the film at the site of application. The moisture retaining semi-permeable adhesive film can be made from a polyurethane or a silicone material with an adhesive coating on at least the border or edges of the film. In one aspect, the adhesive can be an acrylic based adhesive. The semi-permeable film is permeable to oxygen and carbon dioxide, as well as water vapor but will prevent bacterial transmission.

In another aspect, the derivatized polyhydric polymers and compositions thereof of the disclosure can be applied to a semi-permeable film such that the product is premade and ready to use in that the derivatized polyhydric polymer compositions of the disclosure and the semipermeable film are a single unit. Compositions can be packaged directly or indirectly in a foil pouch. In one aspect, the derivatized polyhydric polymer of the disclosure comprises a hyaluronic acid that has been derivatized with sulfonate groups, where such a derivatized polyhydric polymer may be used, for example, in a composition intended for wound healing.

In another aspect, the derivatized polyhydric polymers and compositions of the disclosure can be used as bulking agents. These bulking agents can be used to treat stress urinary incontinence, fecal incontinence, Gastroesophageal Reflux Disease (GERD), prostate-rectum spacer for reduction in rectal damage as a result of radiation treatment for prostate cancer. In one aspect, the injected derivatized polyhydric polymer compositions can be in the form of derivatized polyhydric polymer that may or may not comprise crosslinks.

In one aspect, the derivatized polyhydric polymers and compositions of the disclosure can be used as a dermal filler to fill voids, defects and to treat moderate to severe wrinkles and folds. Derivatized polyhydric polymer compositions can be injected as a solution or suspension. In one aspect, at least one derivatized polyhydric polymer in a derivatized polyhydric polymer composition is crosslinked. In one aspect, the crosslinked derivatized polyhydric polymer of this disclosure used in the dermal filler composition has a hyaluronidase (or corresponding polysaccharide degrading enzyme for other polysaccharides) degradation rate that is the same as or less than that of polyhydric polymer (e.g., hyaluronic acid) that is not derivatized. The derivatized polyhydric polymers and compositions can be used to treat areas where dermal depressions, wrinkles or scars are found including, but not limited to nasolabial folds, forehead, furrow lines and vertical lip lines. In another aspect, the derivatized polyhydric polymers and compositions can be used for lip augmentation and breast augmentation.

In another aspect, the derivatized polyhydric polymers and compositions used as dermal fillers may comprise a drug (e.g., biologically active agent) to reduce pain associated with the procedure. As used herein, a biologically active agent includes compounds or molecules that may be referred to as a drug. Such compounds include benzocaine, bupivacaine, amethocaine, lignocaine, lidocaine, cocaine, cinchocaine, dibucaine, mepivacaine, prilocaine, etidocaine, veratridine (specific c-fiber blocker) and procaine. In another aspect, the derivatized polyhydric polymers and compositions used as dermal fillers may comprise a degradable water-insoluble polymer (e.g. polyester such as PLGA, PLLA etc.), a water insoluble non-degradable polymer (e.g. polymethylmethacrylate [PMMA]) or inorganic material (e.g. calcium hydroxyapatite). In another aspect, the derivatized polyhydric polymers and compositions used as dermal fillers are in the form of particles of a crosslinked hydrogel. In one aspect, median size (Dv50) of the particles are in the range of 100 μm to 800 μm. In another aspect, the median size (Dv50) of the particles are in the range of 200 μm to 600 μm. In one aspect, the crosslinked hydrogel particles are suspended in a saline solution. In another aspect, the hydrogel particles are suspended in a solution of hyaluronic acid or a hyaluronic acid derivative of this disclosure. In one aspect, the crosslinked hydrogel suspension is in a prefilled syringe in which the contents of the syringe are sterile. In another aspect, the hydrogel particle suspension is injectable through at least a 27 G needle.

In one aspect, the derivatized polyhydric polymers and compositions as disclosed herein are formulated for, and are useful for, viscosupplementation. The derivatized polyhydric polymers may or may not crosslinked, and the compositions may optionally contain a biologically active agent.

Viscosupplementation is the process of injecting a derivatized polyhydric polymer composition into the joint to relieve pain. In the preferred aspect, the polyhydric polymer is hyaluronic acid or a derivative thereof. Derivatized polyhydric polymer compositions can be injected into one or more joint spaces of the body. Suitable joints include, but are not limited to, knee, shoulder, ankle, elbow, hip, trapeziometacarpal joint, finger joint, wrist joints, temporomandibular joint, back and neck. In another aspect, the derivatized polyhydric polymers used can comprise crosslinked derivatized polyhydric polymers. The derivatized polyhydric polymer compositions can comprise one or more excipients or diluents. The derivatized polyhydric polymer compositions of the disclosure that can be used for osteoarthritis treatment can be injected through a needle of between 18 gauge and 21 gauge. Derivatized polyhydric polymer composition of the disclosure can comprise a biologically active agent. In one aspect, the biologically active agent can be, but is not limited to, a corticosteroid, a local anesthetic, an antibody, a peptide or an anti-inflammatory compound or molecule. The volume of the solution that comprises the derivatized polyhydric polymer composition of the disclosure can range from 0.5 ml to 10 mL with the preferred aspect being in the 2 mL to 6 mL for injection into the knee. In one aspect, crosslinked derivatized polyhydric polymer hydrogel particles are suspended in a saline solution. In another aspect, the derivatized polyhydric polymer particles are suspended in a solution of hyaluronic acid or a hyaluronic acid derivative on this disclosure. In one aspect, the crosslinked derivatized polyhydric polymer suspension is in a prefilled syringe in which the contents of the syringe are sterile.

In one aspect, the derivatized polyhydric polymers and compositions as disclosed herein are formulated for, and are useful for, adhesion prevention. The derivatized polyhydric polymers may or may not be crosslinked, and the compositions may optionally comprise a biologically active agent. Areas of the body where methods of treatment for adhesion prevention is wanted include spinal and abdominal areas, particularly after surgical procedures, as a coating on dura substitute, in nasal procedures or devices, in conjunction with ear, elbow, and tendon medical procedures. Exemplary biologically active agents include, but are not limited to, anti-inflammatory and pain medicines.

In one aspect, the derivatized polyhydric polymers of this disclosure may be used to reduce the incidence and severity of adhesions and scar tissue that may occur following injury or a surgical procedure. These adhesions can include abdominal adhesions, pelvic adhesions, heart adhesions, joint adhesions, tendon adhesions (e.g. flexor tendon, Achilles tendon, patella tendon), spinal adhesions, lumbar adhesions, nerve adhesions, dural adhesions, sinus adhesions. The derivatized polyhydric polymer compositions can further comprise one or more excipient. The derivatized polyhydric polymer compositions of the disclosure can further comprise a biologically active agent. In one aspect, the biologically active agent can be, but is not limited to, a corticosteroid, a local anesthetic, an antibody, a peptide or an anti-inflammatory. In one aspect, the derivatized polyhydric polymer of this disclosure is derived from hyaluronic acid or a hyaluronic acid derivative. In one aspect, the derivatized polyhydric polymer can be in the form of a crosslinked hydrogel. In another aspect, the derivatized polyhydric polymer of the disclosure can be in a crosslinked form that has been lyophilized to form a porous foam or it could be as a solid or perforated film.

In one aspect, the derivatized polyhydric polymers and compositions as disclosed herein are formulated for, and are useful for, tissue sealing. The derivatized polyhydric polymers may or may not be crosslinked, and the compositions may optionally comprise a biologically active agent.

In one aspect, the derivatized polyhydric polymer of the disclosure that contains residual vinyl sulfone groups can be reacted with a compound that has 2 or more free thiol functional groups such that a crosslinked derivatized polyhydric polymer is produced. In one aspect, the derivatized polyhydric polymer of the disclosure that contains free vinyl sulfone groups can be prepared as a solution. In one aspect, the solution can be prepared using saline. In one aspect, the derivatized polyhydric polymer of the disclosure that contains residual vinyl sulfone groups can be prepared as a first solution and the derivatized polyhydric polymer that has 2 or more free thiol functional groups can be prepared as a second solution. The pH of either the first or the second solution can be adjusted such that the pH of the solution is greater than pH 8. This can be accomplished by using a solution that has a pH of greater than 8 to dissolve either the derivatized polyhydric polymer of the disclosure that contains residual vinyl sulfone groups or the compound that has 2 or more free thiol functional groups, adding buffer components to either the derivatized polyhydric polymer of the disclosure that contains residual vinyl sulfone groups or to the compound that has 2 or more free thiol functional groups.

In one aspect, the first and second solution can be combined and applied to the tissue surface resulting in a mixture. In one aspect, the mixture can be applied through a needle or cannula. In another aspect, the mixture can be applied using a spray applicator. Examples of spray applicators include but are not limited to the Fibrijet SA-3674 and SA-3675 (Nordson Medical, 261 Cedar Hill Street, Marlborough, MA 01752, United States). In another aspect, the mixture can be applied using a gas assisted spray applicator. Examples of gas assisted spray applicators include but are not limited to the Fibrijet SA-3651 and SA-3652, (Nordson Medical, 261 Cedar Hill Street, Marlborough, MA 01752, United States).

In one aspect, the derivatized polyhydric polymer composition can be applied to the tissue in a liquid form and after 3 minutes the derivatized polyhydric polymer composition is in a gel form. The time required to convert from the liquid form to the gel form depends on the specific application. In one aspect the liquid to gel conversion can take less than 2 minutes. In another aspect the liquid to gel conversion can take less than 30 seconds. In another aspect, the liquid to gel conversion can take less than 15 seconds.

The derivatized polyhydric polymer composition for tissue sealing may further comprise an excipient. The derivatized polyhydric polymer composition can further comprise a biologically active agent.

In one aspect, the derivatized polyhydric polymer compositions of this disclosure are combined with a biologically active agent to treat bacterial vaginosis. The derivatized polyhydric polymer compositions of this disclosure can be formulated such that the derivatized polyhydric polymer compositions is tissue adhesive and adheres to the vaginal tissue for a period of greater than 2 hours. The derivatized polyhydric polymer compositions can further comprise one or more excipient. The derivatized polyhydric polymer compositions of the disclosure can further comprise a biologically active agent. In an aspect, the biologically active agent can be an antibacterial agent. In an aspect, the antibacterial can be, but is not limited to, clindamycin, tinidazole, metronidazole, secnidazole and ornidazole. Formulations comprising the derivatized polyhydric polymers of this disclosure, can be applied intravaginally.

In one aspect, the derivatized polyhydric polymers and compositions of the disclosure are selected to provide ocular application. For example, eye drops for dry eyes/lubricating eye drops for contact lenses.

In one aspect, derivatized polyhydric polymer compositions of this disclosure can be used as eye drops. The eye drops can be used to treat dry eyes, a disease of the eye, infected ocular tissue, inflamed ocular tissue, as a lubricant for the surface of the eye, as a lubricant for use with contact lenses and to assist in healing of the eye following trauma or a surgical procedure to the eye or surrounding tissue. Surgical procedures to the eye can include but are not limited to cataract surgery, intra-ocular lens replacement, fixing detached retinas, tumor removal, glaucoma surgery, refractive surgery, corneal surgery, vitreo-retinal surgery, eye muscle surgery, oculoplastic surgery, surgery involving the lacrimal punctum, canaliculus, and sac. An ocular formulation comprising derivatized polyhydric polymers of this disclosure can further comprise an excipient. The derivatized polyhydric polymers of this disclosure can be formulated into a solution or suspension which is then administered to the eye. An ocular formulation comprising derivatized polyhydric polymers of this disclosure can further comprise a biologically active agent. The biologically active agent can be present as part of the solution or it can be in the form of a suspension or emulsion. The derivatized polyhydric polymers of this disclosure can be formulated into a solution or suspension which is then administered to the eye.

In another aspect, derivatized polyhydric polymer compositions of this disclosure can be prepared to be used to lubricate and wet contact lenses. The contact lens can be immersed prior to use or could be stored in a solution that contains derivatized polyhydric polymers of this disclosure. The solution can comprise one or more excipients. The solution can further comprise boric acid or sodium borate. The solution can be formulated to be preservative free.

In one aspect, derivatized polyhydric polymers of this disclosure can be formed into a formulation that is inserted into the lacrimal punctum, the lacrimal canaliculus or the lacrimal sac. Derivatized polyhydric polymers of the disclosure can be in the form of a solution, swollen hydrogel or a dehydrated hydrogel. In one aspect, the derivatized polyhydric polymer compositions can further comprise an excipient. In another aspect, the derivatized polyhydric polymer is crosslinked. In another aspect, derivatized polyhydric polymer compositions further comprise a biologically active agent. In one aspect, the biologically active agent can be but is not limited to a corticosteroid (for example, dexamethasone, mometasone fuorate, triamcinolone acetonide, triamcinolone hexacetonide, triamcinolone acetate, betamethasone, fluoromethalone, hydrocortisone, medrysone or prednisolone), prostaglandins (for example, latanoprost, travoprost or bimatoprost), beta blockers (for example timolol or betaxolol), alpha-adrenergic agonists (for example apraclonidine or brimonidine), carbonic anhydrase inhibitors (for example dorzolamide or brinzolamide), mitotic or chlorinergic agents (for example pilocarpine)

In another aspect, a derivatized polyhydric polymer and/or compositions is crosslinked in the presence of a biologically active agent and then dried. In another aspect, a derivatized polyhydric polymer is crosslinked, dried, reswollen in the presence of a biologically active agent and then dried. In another aspect, the biological agent is incorporated into the uncrosslinked derivatized polyhydric polymer in solution. In another aspect, the derivatized polyhydric polymer is dried, reswollen in the presence of a biologically active agent and then dried. Any of the dried formulations can be of suitable dimensions such that it can be placed in the lacrimal punctum. Upon contact with lachrymal fluid and tears, the final dried formulation hydrates, and swells in such a manner as to be physically retained in the punctum. In another aspect, the dried formulation can be inserted into the canaliculus. Upon contact with lachrymal fluid and tears, the dried formulation hydrates, and swell in such a manner as to be physically retained in the canaliculus. The formulation could then release the contained biologically active agent over a period of 24 hours to 3 weeks. In one aspect, the biologically active agent is released in a sustained manner for a period of 7 days. In one aspect, the biologically active agent is released in a sustained manner for a period of 4 weeks. In an aspect, the dried formulation can be inserted intravitreally so that the biologically active agent is delivered into the vitreous of the eye. In an aspect, the dried formulation is inserted into the anterior chamber of the eye.

In an aspect, the derivatized polyhydric polymers and compositions of the disclosure are selected to provide a punctal plug. The punctal plug may comprise a biologically active agent, e.g., steroid or a pain relief drug.

In one aspect, the derivatized polyhydric polymer compositions of this disclosure can be used to treat mucositis. Examples of mucositis include oral and vaginal mucositis. During cancer treatments, the rapidly divided epithelial cells lining the gastro-intestinal tract (which goes from the mouth to the anus) break down leaving the mucosal tissue open to ulceration and infection. This leads to mucocitis. Oral mucositis can often occur following chemotherapy and radiation treatments. It can lead to pain and increased risk of infection. This can lead to nutritional problems due to these symptoms reducing the ability and desire to eat. Providing a coating that covers these lesions, can reduce the pain and potential for infection. The derivatized polyhydric polymers of this disclosure can be formulated such that the derivatized polyhydric polymer compositions is tissue adhesive and adheres to the mucosal tissue of the mouth tissue or the vagina for a period of greater than 2 hours. The derivatized polyhydric polymer compositions can further comprise one or more excipients. The derivatized polyhydric polymer compositions of the disclosure can further comprise a biologically active agent. In one aspect, the biologically active agent can be, but is not limited to, a local anesthetic, an anti-infective, an anti-inflammatory or a combination thereof. Local anesthetics can include but are not limited to benzocaine, bupivacaine, amethocaine, lignocaine, lidocaine, cocaine, cinchocaine, dibucaine, mepivacaine, prilocaine, etidocaine, veratridine (specific c-fiber blocker) and procaine. For oral mucositis, the derivatized polyhydric polymer compositions of the disclosure can be formulated such that it can be applied as an oral rinse or applied as a gel. For vaginal mucositis, the derivatized polyhydric polymer compositions of the disclosure can be formulated such that it can be applied intravaginally to the vaginal tissue surface.

In one aspect, derivatized polyhydric polymer compositions of this disclosure can be used to treat a surgical site during and following canalplasty, tympanoplasty, myringoplasty, stapedectomy mastoid procedures, or any other procedure related to the ear. Derivatized polyhydric polymer compositions can be used to modulate wound healing as well as to control bleeding. The derivatized polyhydric polymer compositions of this disclosure can be in the form of a lyophilized sponge, an electrospun matrix, a film, a gel or a combination of these forms. The derivatized polyhydric polymer compositions of the disclosure can comprise an excipient. In another aspect, the derivatized polyhydric polymer compositions of the disclosure can comprise a biologically active agent.

In another aspect, the derivatized polyhydric polymer compositions of the disclosure can be used to treat otitis media, acute otitis externa, balance disorders (for example Meniere' disease, tinnitus and sensorineural hearing loss. Derivatized polyhydric polymer compositions of this disclosure can be in the form of a solution, a suspension, a lyophilized sponge, an electrospun matrix, a film, a gel, a solid rod-like form, or a combination of these forms. Derivatized polyhydric polymer compositions of the disclosure can comprise an excipient. In another aspect, a derivatized polyhydric polymer compositions of the disclosure can comprise a biologically active agent. To treat infections of the ear, the derivatized polyhydric polymer can comprise an antibiotic, an antibacterial, an antiviral, an antifungal or a combination thereof. In one aspect, derivatized polyhydric polymer compositions comprising at least one biologically active agent include, but are not limited to, amoxicillin, clavulanate, cefuroxime axetil, ceftriaxone, Levofloxacin, a cephalosporin, a trimethoprim-sulfamethoxazole, a macrolide, ofloxacin, gentamicin sulfate, tobramycin sulfate and ciproflaxin, In another aspect, derivatized polyhydric polymer compositions can comprise a corticosteroid. Corticosteroids can include but are not limited to betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide, mometasone furoate. In another aspect, a combination of an antibiotic and a corticosteroid can be added to the derivatized polyhydric polymer compositions of the disclosure. In one aspect, the derivatized polyhydric polymer compositions of the disclosure can be applied to the area to be treated by being applied with a dropper, a syringe, through a needle or catheter or by physically placing a derivatized polyhydric polymer compositions.

In one aspect, the derivatized polyhydric polymer compositions of the disclosure can comprise a biologically active agent. The derivatized polyhydric polymers of this disclosure can be used as a matrix from which the biologically active agent can be delivered. In one aspect the release profile of the biologically active agent into a phosphate buffered saline solution if slower than that of the normal dissolution profile of the biologically active agent. In one aspect, the derivatized polyhydric polymer compositions of the disclosure can be in the form of a crosslinked gel.

In one aspect, the treatment using the drug delivery formulation can be a single injection or could be two or more injections that are separated by a period of time. The composition can be injected subcutaneously, intra-dermally or intra-muscularly. The derivatized polyhydric polymer compositions can be injected through a needle, trocar, catheter, tube, or cannula.

In another aspect, the contents of the prefilled syringe or vial are sterile. In another aspect, the contents of the prefilled syringe or vial are stable at 2-8° C. or 20-25° C. for at least 6 months, preferably 12 months and most preferably 24 months. In another aspect, the drug delivery formulation can be applied topically or by instillation.

In one aspect, the derivatized polyhydric polymers of this disclosure in a crosslinked form can be used as device to plug a defect following the removal of a piece of tissue or the needle track following a biopsy procedure. In another aspect, a crosslinked form of the derivatized polyhydric polymer compositions can be prepared and then dried. The dried derivatized polyhydric polymer compositions can be delivered into the needle track or the site that a piece of tissue was removed. The dried derivatized polyhydric polymer compositions can absorb moisture from the surrounding tissue to rehydrate and swell such that the swollen size is larger than the initial size of the derivatized polyhydric polymer compositions. The swollen derivatized polyhydric polymer composition is then retained at the site into which it is placed. In another aspect, the crosslinked dried derivatized polyhydric polymer composition can be used to seal a hole in the tissue where the crosslinked derivatized polyhydric polymer composition is placed in the hole and it swells to seal off the hole. An example of this could be to seal lung tissue following puncturing of the lung following a biopsy or surgical procedure. In another aspect, the crosslinked dried derivatized polyhydric polymer composition can comprise an element, such as a metal piece that is visible under x-ray or fluoroscopy examination. The metal piece can take on various forms such as but not limited to a flat piece, a rod, a coil, a loop, a hoop, hook, a number and a letter of the alphabet. In one aspect, the crosslinked dried derivatized polyhydric polymer composition can comprise a biologically active agent. In another aspect, the biologically active agent can have hemostatic properties. In one aspect, the crosslinked dried derivatized polyhydric polymer composition can comprise collagen, chitosan or thrombin.

In one aspect, the derivatized polyhydric polymers and compositions of the present disclosure are formulated for, and are useful for, a plug for female sterilization. Female sterilization can be accomplished by inserting a plug into the fallopian tube. This plug can provide a physical barrier to the passage of the ovum into the uterus as well as to the sperm reaching the ovum. The predominant procedure to effect female sterilization in a laparoscopic procedure in which the fallopian tubes are severed and then ligated. In other versions of the procedure, the fallopian tubes can be closed using clips or rings to clamp then closed. Cauterization has also been used to seal the fallopian tubes. These procedures are generally classed as major surgery, usually requires general anesthesia and the patient requires a recuperation period. Transvaginal sterilization procedures were an alternative to the laproscopic procedures as they were less invasive. Initial transvaginal procedures used chemical agents, such as sodium morrhuate, or quinacrine, methyl cyanoacrylate and silver nitrate, but the success rates and side effects have limited their use. Hysteroscopic tubal sterilization has emerged as a minimally invasive alternative to conventional tubal ligation. Hysteroscopic tubal sterilization can be performed in approximately 10 minutes in an office setting without the use of general or even local anesthesia.

Two hysteroscopic tubal sterilization products were commercialized, but both have been removed from the US market by the end of 2018. The Essure system consisted of a device insert that is loaded into a single-use delivery system. The device consisted of an inner coil of stainless steel and polyethylene terephthalate (PET) fibers and an outer coil of nickel-titanium (nitinol). The metal components hold the device in place while the PET fibers allow tissue ingrowth into the device which will lead to occlusion of the fallopian tube. This ingrowth process does take time and so the patient must use other forms of contraception for 3 months. At this stage a hysterosalpingogram is performed to confirm placement and tubal occlusion. The device is permanent and remains in the patient for the rest of the patient's life. This product received a black box warning over potential safety concerns, and was subsequently removed from the market in the US. The device had previously been removed from the market overseas.

Another sterilization method was developed by Hologic. The Adiana® sterilization method used radiofrequency energy to cause controlled thermal damage of the lining of the fallopian tube lumen. Following the thermal injury to the fallopian tube, a porous non-degradable silicone plug is placed in the thermally injured fallopian tube. Over a few weeks, tissue ingrowth into the porous plug results in occlusion of the fallopian tube. A hysterosalpingogram is performed at 3 months to confirm tubal occlusion. The silicone plug is a permanent implant. The Adiana® system has been withdrawn from the market.

The Essure system and the Adiana® system both leave a permanent device in the patient. This can potentially lead to longer term safety issues for the patient. Having a system that comprises a degradable plug component would be beneficial in that little to no derivatized polyhydric polymer and/or composition will remain permanently within the patient. The method and devices described herein provide a means to occlude the fallopian tube that will result in a reduction in the ability of a female to become pregnant. The method involves mechanically injuring the lining of the fallopian tube followed by the insertion of a degradable plug.

A method for mechanically injuring the fallopian tube is to insert a device that comprises a rough surface into the fallopian tube and then physically move the device in a rotational motion, a linear motion that follows the fallopian tube or a combination thereof. This motion can be repeated more than once. This physical movement is continued until the endothelial layer of the fallopian tube where the physical motion occurs is either partially removed or completely removed.

The device used to denude the endothelial layer of the fallopian tube can comprise a series of fiber radiating from a central core. In one aspect this device is similar in structure to a bottle brush, e.g., a rod with bristles (fibers) extending perpendicularly from the rod.

In one aspect, the fibers can be spaced evenly apart in a continuous manner. In one aspect, the fibers can be in rows with spaces between the rows. In one aspect, the fibers could be oriented in a spiral shape along the axis of the device. In one aspect, the fibers can be oriented in one or more linear rows that are aligned about parallel with the axis from which they emanate. In another aspect, the fibers are in one or more rows such that the rows are about perpendicular to the axis from which they emanate.

In one aspect, the fibers can be made from a non degradable polymer. The polymers that can be used to prepare the fibers include but are not limited to polyethylene, polypropylene, polyethylene terephthalate (PET), nylon, polyurethane, polyetheretherketone (PEEK), polyaryletherketone (PAEK), fluorocarbon polymers such as polytetrafluoroethylene, silk and combinations thereof.

In one aspect, the fibers can be made from a metal. The metals that can be used to prepare the fibers include but are not limited to stainless steel, titanium, nitinol, magnesium, alloys of Co—Cr—Mo, Cr—Ni—Cr—Mo, CP—Ti, Ti—Al—V, Ti—Al—Nb, Ti-13Nb-13Zr, Ti—Mo—Zr—Fe or combinations thereof.

In one aspect, the central core (rod) of the denuding device can comprise a core prepared from the twisting of 2 or more metal strands together such that the fibers are trapped between the twisted metal strands. The metals that can be used to prepare the central core include but are not limited to stainless steel, titanium, nitinol, magnesium, alloys of Co—Cr—Mo, Cr—Ni—Cr—Mo, CP—Ti, Ti—Al—V, Ti—Al—Nb, Ti-13Nb-13Zr, Ti—Mo—Zr—Fe or combinations thereof.

In one aspect, the terminal end of the central core (rod) that is first introduced into the fallopian tube can comprise an atraumatic tip that does not damage the tissue as the device is being guided into the desired location in the fallopian tube. This atraumatic tip can be a rounded end cap, a domed shaped end, a cone shaped end with a rounded tip. The surface of the atraumatic tip can have a smooth surface. The atraumatic tip can be made of a non-degradable polymer or a metal. The non-degradable polymers that can be used to manufacture the atraumatic tip include but are not limited to polyethylene, polypropylene, polyethylene terephthalate (PET), nylon, polyurethane, polyetheretherketone (PEEK), polyaryletherketone (PAEK), fluorocarbon polymers such as polytetrafluoroethylene, silk and combinations thereof. The metals that can be used to prepare the atraumatic tip include but are not limited to stainless steel, titanium, nitinol, magnesium, alloys of Co—Cr—Mo, Cr—Ni—Cr—Mo, CP—Ti, Ti—Al—V, Ti—Al—Nb, Ti-13Nb-13Zr, Ti—Mo—Zr—Fe or combinations thereof.

The atraumatic tip can be attached to the central core by a crimping process, a molding process, a process that uses an adhesive to bond the tip to the central core, or a thermal process.

The plug can comprise a hydrogel. In one aspect, the hydrogel is prepared using one or more crosslinked derivatized polyhydric polymer and/or compositions of this disclosure. A hydrogel comprising a polyhydric polymer composition in the form a rod that is larger than the size of the fallopian tube is prepared. The hydrogel rod is then dried. The hydrogel can be dried at normal atmospheric pressures or under reduced atmospheric pressure. In one aspect, the hydrogel can be lyophilized. Once delivered to the desired site, the hydrogel plug would absorb moisture from the fallopian tube and swell. The swelling of the hydrogel plug will enable the hydrogel plug to be retained at the site where it was placed.

In one aspect, the hydrogel further comprises a porogen to facilitate the formation of pores within the hydrogel. The porogen can comprise particulates. The particulates can comprise a degradable polymer. Degradable polymers that can be used as porogens include but are not limited to degradable polyesters, polyanhydrides, polyurethanes, polyether-esters, polycarbonates, polyether-carbonates, polyether-ester carbonates, polkyhydroxyalkanoates, polyamides and polymers that are synthesized from one or more monomers from the group of l-lactide, dl-lactide, glycolide, ε-caprolactone, trimethylene carbonate, morpholine-dione, p-dioxanone and 1,5-dioxapan-2-one.

In one aspect, the porogen can be leeched out of the hydrogel during the device manufacturing process. This can be accomplished by incubating the porogen containing hydrogen in a solvent in which the porogen will dissolve. The solvent is preferably a water miscible solvent. In another aspect, the porogen can remain in the device throughout the manufacturing process and will degrade and leech out once the hydrogel plug is inserted into the patient.

In one aspect the plug comprises a degradable polymer. Degradable polymers that can be used in the plug include but are not limited to degradable polyesters, polyanhydrides, polyurethanes, polyether-esters, polycarbonates, polyether-carbonates, polyether-ester carbonates, polkyhydroxyalkanoates, polyamides and polymers that are synthesized from one or more monomers from the group of l-lactide, dl-lactide, glycolide, ε-caprolactone, trimethylene carbonate, morpholine-dione, p-dioxanone and 1,5-dioxapan-2-one.

The plug can comprise a monofilament structure, a multifilament structure, or a braided structure. In one aspect, the plug can be prepared by taking particles or chopped fibers of the degradable polymer and compression mold them into a shape. Heat can be used to thermally fuse the particulates together such that a porous structure is obtained. In one aspect, the shape can be in the form of a rod. The porous rod can then be cut to a predetermined length.

In one aspect, the plug can be made from an electrospun degradable polymer. In one aspect, the plug is made from a thin film of electrospun derivatized polyhydric polymer and/or compositions. The plug can be cut directly from a sheet of the electrospun composition. In one aspect, the plug can be prepared by rolling an electrospun film into a roll. The electrospun plug or the rolled rod shaped structure can be coated with a second degradable polymer such that the rolled configuration is retained. In one aspect, the polymer used to prepare the rolled structure has a degradation time that is longer than the polymer used to coat the rolled structure. This can allow the plug to be more rigid which makes handling easier during manufacturing but upon delivery to the desired site, the faster degrading material will start degrading and facilitate tissue ingrowth while the first longer lasting polymer provides a scaffold for the ingrowing tissue.

In another aspect, the electrospun plug can be coated or dipped into a solution of a water-soluble polymer. The plug is then dried at ambient pressure or at reduced pressure. The plug may also be dried by lyophilization. The presence of the water soluble polymer can make the electrospun composition more rigid and thus easier to handle during manufacturing and delivery to the intended site. Once positioned at the intended site, the polymer will start to dissolve and leech out of the electrospun composition. The tissue from the mechanically damaged fallopian tube can then grow into the electrospun composition. The electrospun composition will degrade over time leaving an occluded fallopian tube. In one aspect, the water soluble polymer can be selected from the group of polyethylene oxide, polyethylene glycol, block copolymers of polyethylene glycol and polypropylene glycol (e.g. Pluronics F126 and Pluronics F68, Sigma-Aldrich Corp., St. Louis, MO, USA), dextran, hyaluronic acid, or a hyaluronic acid derivative of this disclosure.

The degradable polymer used to form the plug can further comprise a porogen. The porogen can comprises an inorganic salt, an organic small molecule or a polymer. The porogen is selected such that it is soluble in a solvent in which the biodegradable polymer used to prepare the plug has limited solubility.

Inorganic salts that can be used as porogens include but not limited to sodium salts, potassium salts, calcium salts, magnesium salts, aluminum salts, copper salts, barium salts, iron salts. Examples of these salts include but are not limited to sodium chloride, sodium bromide, sodium iodide, sodium sulfate, sodium phosphate, sodium hydrogen phosphate, or combinations thereof.

A porous plug can be prepared by 3D-printing the plug. A degradable polymer can be used to 3D print the plug. In one aspect, the degradable polymer that can be used in the plug include but are not limited to degradable polyesters, polyanhydrides, polyurethanes, polyether-esters, polycarbonates, polyether-carbonates, polyether-ester carbonates, polkyhydroxyalkanoates, polyamides and polymers that are synthesized from one or more monomers from the group of l-lactide, dl-lactide, glycolide, ε-caprolactone, trimethylene carbonate, morpholine-dione, p-dioxanone and 1,5-dioxapan-2-one.

The plug can comprise position retaining features. These features can include non-symmetrical shapes, barbs, ridges, pores, slits, slots, or a combination thereof. The barbs can be unidirectional in that they all point in the same direction or the barbs could point in two or more different directions. The barbs could be uniformly spaced on the plug or they could be present in only specific portions of the plug.

In one aspect, plug can be dipped into a solution of the derivatized polyhydric polymers of the disclosure. The solution can then be activated to allow the solution to crosslink such that the pores of the plug comprise the crosslinked derivatized polyhydric polymer. The crosslinking process can be activated by adjusting pH of the solution, addition of a crosslinking agent, elevation of temperature, addition of an initiator or a combination of one or more of these.

In one aspect, the derivatized polyhydric polymer compositions of the disclosure can be used as a scaffold to allow the ingrowth of tissue or bone. In one aspect, derivatized polyhydric polymers of this disclosure can be prepared as a crosslinked matrix that is then lyophilized. The lyophilized derivatized polyhydric polymer composition can then be rehydrated in the presence of cells such that the hydrated matrix acts as a scaffold that allows the growth of the cells on and into the scaffold. In another aspect, the derivatized polyhydric polymers of this disclosure that have residual vinyl sulfone groups, can be electrospun to form a porous matrix. The electospun fibers can then be crosslinked using heat, ultraviolet, e-beam or gamma radiation. In another aspect, the derivatized polyhydric polymer of the disclosure that contains residual vinyl sulfone groups can further comprise a photocrosslinker. A solution of this composition can be electrospun and then the electrospun matrix can be subjected to ultraviolet radiation such that the photocrosslinker results in crosslinking of the derivatized polyhydric polymer. The resultant matrix can be rehydrated in the presence of cells such that it acts as a scaffold for tissue growth. In another aspect, carboxylic acid containing derivatized polyhydric polymers of this disclosure can be electrospun into a matrix by mixing a solution of the derivatized polyhydric polymer of this disclosure with a solution of a multivalent cation just prior to electrospinning. In one aspect, a solution of a carboxylic acid containing composition of this disclosure could be placed in one syringe and a solution of a multivalent cation or a cationic polymer can be placed in another syringe. The syringes can be connected via a γ-connector and a needle can be connected to final arm of the γ-connector. They two solutions can then be pumped through the needle and this mixture can be electrospun onto a surface such that the derivatized polyhydric polymer of the disclosure is ionically crosslinked. Multivalent cations can include calcium magnesium, ferric ions, ferrous ions, aluminum and chromium.

Cationic polymers that can be used include but are not limited to chitosan and derivatives thereof, polyvinyl pyrolidone, peptides containing more than one lysine group and polyethyleneimine.

In another aspect, a solution of a derivatized polyhydric polymer compositions of this disclosure can be used to coat a degradable or non-degradable scaffold matrix. In one aspect, a derivatized polyhydric polymer of this disclosure that has been modified with alkyl or aryl groups can be used to coat a scaffold for tissue growth. The alkyl or aryl groups will interact with the scaffold through hydrophobic bond while the hydrophilic portion of the derivatized polyhydric polymer will allow for cell growth on the coated scaffold surface. In another aspect, the derivatized polyhydric polymers of this disclosure that have residual vinyl sulfone groups, can be coated onto the scaffold. The coated scaffold can be subjected to heat which will result in the derivatized polyhydric polymer transforming into a crosslinked derivatized polyhydric polymer.

In another aspect, the derivatized polyhydric polymers and/or compositions of the disclosure can comprise a sulfonate group. In another aspect, the derivatized polyhydric polymers and/or compositions of the disclosure can comprise both hydrophobic groups and sulfonate groups. The hydrophobic groups can be alkyl or aromatic based.

In another aspect, tissue scaffold support structure can be 3D printed or electrospun using a degradable polymer. The degradable polymer that can be used can include but not limited to degradable polyesters, polyanhydrides, polyurethanes, polyether-esters, polycarbonates, polyether-carbonates, polyether-ester carbonates, polkyhydroxyalkanoates, polyamides and polymers that are synthesized from one or more monomers from the group of l-lactide, dl-lactide, glycolide, ε-caprolactone, trimethylene carbonate, morpholine-dione, p-dioxanone and 1,5-dioxapan-2-one.

In another aspect for the electrospun scaffold support structure, a single or multiple polymer solutions can be prepared. The polymers used can be biodegradable polymers then include but are not limited to polyester, polyanhydride, polyorthoester, polycarbonate, poly-ester-co-carbonate), polyhydroxybutyrates or combinations thereof. Biodegradable polymers can include polylactice-co-glycolide copolymers, polydioxanone, polylactide-trimethylene carbonate copolymers as well as copolymers that comprise repeat units derived from at least one of the following monomers: l-lactide, dl-lactide, glycolide, trimethylene carbonate, epsilon-caprolactone, p-dioxanone and a morpholinedione The solvents used can be an organic solvent, water or a combination thereof. For example, HFIP, DMSO, NMP, Chloroform, acetic acid, ethanol, dimethylformamide (DMF) solvents or mixtures of solvents can be used. Solutions with a concentration of 0.5 to 25% (w/v) can be prepared. The solution that is to be electrospun can be placed in a syringe with a needle. The syringe is then placed in a syringe pump. The needle can have a blunt end and an inner diameter in the range of 0.25 to 2.5 mm. The needle and collection plate are attached to a high voltage supply. In some applications, more than one needle can be used to prepare a single sheet. The needles can be arranged such that the same polymer solution flows through all the needles, different solutions flow through different needles or a combination thereof. The needles can be arranged such that adjacent needles allow different polymer solutions to flow through them. This alternation pattern can be repeated. A voltage is then applied to the system. The applied voltage can be in the 10 kV to 45 kV. The syringe pump can extrude the solution. The flow rate of the syringe pump can be in the range of 0.0001 uL/min to 423 mL/min. The collector plate can be static, rotating or moving in a specific linear direction to give the fibers some directional orientation. The shape of the collector plate can be varied with the collector plate having but not limited to the following shapes: a flat surface, a textured surface, a curved surface, a square rod, a rectangular rod, a round mandrel, an oval mandrel, a semi-circular mandrel or a combination of these shapes. The distance of the needle tip to the collector plate can be altered. The distance of the needle tip to the collector plate can be in the 2-50 cm range. The collection plate can also be submerged in or sprayed with a solvent that assists in the precipitation of the newly spun fibers. For example, an ethanol bath may be used during the electrospinning of hyaluronic acid based derivatized polyhydric polymers of this disclosure. The derivatized polyhydric polymer of the disclosure can be incorporated through a solution coating or submersion of an electrospun matrix.

In one aspect the polymer composition used to 3D print or electrospin the scaffold can further comprise an inorganic filler or a combination of inorganic fillers. In one aspect the inorganic filler can be selected from the group calcium carbonate, calcium phosphate, tricalcium phosphate, hydroxyapatite, bioglass, or a combination thereof.

In one aspect, 3D-printed or electrospun scaffold can be coated with a solution of the derivatized polyhydric polymers of the disclosure. This derivatized polyhydric polymer can be coated onto the scaffold through a dip coating or spray coating process. In another aspect, the derivatized polyhydric polymer can be dispersed into the scaffold through compressive application. In another aspect, the derivatized polyhydric polymer can be dispersed into the scaffold through submersion in solution which may or may not include sonication to aid in dispersion. In another aspect, the coated scaffold can be dried. The drying process can include drying at elevated temperature, drying at reduced pressure or lyophilization. In another aspect, the solution of the derivatized polyhydric polymer compositions of the disclosure can further comprise a biologically active agent.

In another aspect, scaffold can be dipped into a solution of the derivatized polyhydric polymers of the disclosure. The solution can then be activated to allow the solution to crosslink such that the pores of the scaffold comprise the crosslinked derivatized polyhydric polymer. The crosslinking process can be activated by adjusting pH of the solution, addition of a crosslinked, elevation of temperature, addition of an initiator or a combination of one or more of these.

In another aspect, scaffold can be dipped into a solution of the derivatized polyhydric polymers of the disclosure and allowed to dry or be lyophilized. The derivatized polyhydric polymers within the substrate can then be dipped into a crosslinking solution to allow the solution to crosslink such that the pores of the scaffold comprise the crosslinked derivatized polyhydric polymer. The crosslinking process can be activated by adjusting pH of the solution, addition of a crosslinked, elevation of temperature, addition of an initiator or a combination of one or more of these.

In another aspect, scaffold can be dipped into a solution of the derivatized polyhydric polymers of the disclosure and a crosslinking agent. The rate of the crosslinking reaction can be controlled such that the scaffold can be coated with the derivatized polyhydric polymer and/or composition prior to complete crosslinking of the derivatized polyhydric polymer. In one aspect a biologically active agent can be incorporated into the derivatized polyhydric polymer and/or compositions before or immediately following the initiation of the crosslinking reaction. The scaffold can then be coated with this composition and once applied to the scaffold, the crosslinking reaction is completed such that the device comprises the crosslinked derivatized polyhydric polymer with the biologically active agent essentially encapsulated by the crosslinked derivatized polyhydric polymer composition.

In another aspect, the derivatized polyhydric polymers and/or compositions of this disclosure are used to prepare a scaffold or to coat the scaffold can comprise a biologically active agent. In one aspect, the biologically active agent can enhance cell growth. In one aspect, the biologically active agent can be one or more growth factors or peptides that enhance cell growth and cell adhesion. In another aspect, the derivatized polyhydric polymers and/or compositions of this disclosure used to prepare a scaffold or to coat the scaffold can further comprise an excipient. In one aspect, the derivatized polyhydric polymer compositions of the disclosure can comprise one or more extracellular matrix components. The extracellular matrix component can include but are not limited to heparan sulfate, chondroitin sulfate, keratin sulfate, hyaluronic acid, collagen, elastin, fibronectin, and laminin.

In one aspect, the cells that can be added to the scaffolds that contain the derivatized polyhydric polymer compositions of this disclosure include embryonic stem cells, mesenchymal stem cells, adipose-derived stem cell, endothelial stem cells, dental pulp stem cells, tumor cells, chondrocytes, osteoblasts, dermal fibroblasts, protomyofibroblasts, myofibroblasts, hepatocytes, smooth muscle cells, endothelial cells, epithelial cells, adipose tissue, adipose cells and cardiac cells In one aspect, the derivatized polyhydric polymers and compositions of the present disclosure comprise free vinyl sulfone functional groups and can be used to 3D print structures. The derivatized polyhydric polymers can be prepared as solutions with viscosities that allow them to be 3d printed. In one aspect, a solution of the derivatized polyhydric polymer with residual vinyl sulfone groups can be prepared. A second solution containing a derivatized polyhydric polymer with at least two free thiol groups can be prepared. In one aspect, the first and second solution can be mixed together. Just prior to printing, the pH of the mixture can be adjusted to a pH of greater than 8, preferably greater than 9, such that the mixture can be printed and then cure following printing. In one aspect, the pH can be adjusted by mixing the mixture with a buffer solution that has a pH of greater than 8. The mixing takes place just prior to the print head ensuring that the mixture does not gel up in the print head and thus clot the printer, In another aspect, the solution of the derivatized polyhydric polymer that comprises the residual vinyl sulfone functional groups can has its pH adjusted to a pH of greater than 8 by mixing it with a buffer solution. This solution can then be mixed with solution 2 just prior to the print head such that the mixture is printed and then allowed to complete gelation once printed.

The viscosity of the mixture can be used to control the retention of the printed structure until gelation is completed. In another aspect, a thermogelling material can be added to either the first, second or buffer solution. Thus, the mixture can be printed and then the temperature of the printed environment can be different from the solution prior to printing such that following the printing process the printed solution undergoes thermal gelation to preserve the initial printed structure while the crosslinking process is moving towards completion.

Thermogelling materials can include but are not limited to polyethylene-block-polypropylene co polymers such as Pluronics F127 or F68 (Sigma-Aldrich Corp., St. Louis, MO, USA) or polyester-polyethylene glycol block co polymers. The polyester-polyethylene glycol copolymers can include deblock and triblock copolymers. The polyester component are polymers that are synthesized from at least one of the monomers from the group of l-lactide, dl-lactide, glycolide, ε-caprolactone, morpholine-dione, p-dioxanone and 1,5-dioxapan-2-one. In another aspect, a thermogelling polymer that comprises trimethylene carbonate can be used.

Following the completion of the gelation process, the printed construct can be rinsed to neutralize the pH of the printed gel. In another aspect the printed structure can be dried such that the residual water content is less than 10%. In another aspect, the printed structure can be lyophilized.

The printed structure can be used as a tissue scaffold, for wound healing applications, for occlusion of a lumen, a biopsy site or a needle tract.

For procedures such as neuroendoscopy, intracranial decompression, and treatment of chronic subdural hematoma, holes are often drilled into the skull. These are often referred to as burr holes. In many instances, these burr holes are left untreated following the surgical procedure and the scalp is replaced directly over these holes. This can lead to scalp depressions at the burr hole. These scalp depressions can lack mechanical strength. In order to prevent this, a burr hole plug can be inserted into the burr hole such that it can facilitate and support bone regrowth. Autologous bone can be used to fill the burr holes but this requires harvesting of the bone. Synthetic materials can be used as burr hole plugs. A degradable burr hole plug that degrades while facilitating bone ingrowth will allow the healing of the burr hole without leaving residual material. A polycaprolactone (PCL) burr hole plug has been commercialized. The challenge with PCL is that it is slow degrading and the interface between the polymer and the in-growing tissue is usually not the best due to the hydrophobicity of the polymer.

The derivatized polyhydric polymers and compositions thereof of the disclosure can be made into a burr hole plug. A solution of a derivatized polyhydric polymer can be placed in the mold and then the derivatized polyhydric polymer composition can be lyophilized to produce a porous structure that can be inserted into the burr hole. In another aspect, the derivatized polyhydric polymer compositions of the disclosure can be electrospun and then cut to form a plug that can be inserted into the burr hole. In another aspect, a solution of the derivatized polyhydric polymer of the disclosure can be placed in a mold and the solution can be crosslinked. The crosslinked plug can be used directly. In another aspect, the crosslinked derivatized polyhydric polymer compositions can be lyophilized to yield a porous crosslinked structure that can be used as a burr hole plug.

In another aspect, a burr hole plug can be 3D printed or electrospun using a degradable polymer. The degradable polymer that can be used can include but not limited to degradable polyesters, polyanhydrides, polyurethanes, polyether-esters, polycarbonates, polyether-carbonates, polyether-ester carbonates, polkyhydroxyalkanoates, polyamides and polymers that are synthesized from one or more monomers from the group of l-lactide, dl-lactide, glycolide, ε-caprolactone, trimethylene carbonate, morpholine-dione, p-dioxanone and 1,5-dioxa pan-2-one.

In one aspect the polymer used to 3D print or electrospin the burr hole plug can further comprise an inorganic filler or a combination of inorganic fillers. In one aspect the inorganic filler can be selected from the group calcium carbonate, calcium phosphate, tricalcium phosphate and hydroxyapatite.

In one aspect, the 3d-printed or electrospun burr plug can further comprise an extracellular matrix material. In one aspect, the extracellular matrix material can be selected from the group collagen, hyaluronic acid, chondroitin sulfate, heparan sulfate, keratin sulfate, elastin, fibronectin and laminin.

In one aspect, 3D-printed or electrospun plug can be coated with a solution of the derivatized polyhydric polymers of the disclosure. This derivatized polyhydric polymer composition can be coated onto the plug through a dip coating or spray coating process. In another aspect, the coated plug can be dried. The drying process can include drying at elevated temperature, drying at reduced pressure or lyophilization.

In another aspect, polymeric degradable plug can be dipped into a solution of the derivatized polyhydric polymers of the disclosure. The solution can then be activated to allow the solution to crosslink such that the pores of the plug comprise the crosslinked derivatized polyhydric polymer composition. The crosslinking process can be activated by adjusting pH of the solution, addition of a crosslinker, elevation of temperature, addition of an initiator or a combination of one or more of these.

In another aspect, polymeric degradable plug can be dipped into a solution of the derivatized polyhydric polymers of the disclosure that contain residual vinyl sulfone groups. The coated device can be dried at elevated temperatures to remove the solvent and to allow crosslinking of the coating such that the pores of the plug comprise the crosslinked derivatized polyhydric polymer composition.

In one aspect, the crosslinked forms of the derivatized polyhydric polymers and/or compositions of this disclosure can be used to form nerve guides. Optionally, the nerve guides can be prepared by lyophilization. In one aspect, collagen, gelatin, chitosan heparan sulfate or a combination of these can be further added to the derivatized polyhydric polymers and/or compositions of the disclosure to form the nerve guides. In another aspect, Schwann cells can be incorporated into the derivatized polyhydric polymer compositions during the formation of the nerve guide.

In one aspect, the derivatized polyhydric polymers if this disclosure can be prepared as a solution that has a viscosity of greater than 50 cP. In one aspect, this solution can be applied to tissue to reduce the coefficient of friction with the tissue surface. In one aspect, the derivatized polyhydric polymer composition can be used as a vaginal lubricant. In another aspect, the solution can be applied to a device that is to be inserted into an opening, orifice or cavity such that the solution act to lubricate the passage of the device through the opening, orifice or cavity. In one aspect the device could be an endoscope.

In one aspect, the derivatized polyhydric polymer and compositions thereof of this disclosure can be used to coat a medical device. Medical devices that can be coated include but are not limited to a catheter, a needle, a biopsy needle, a tissue marker, a guide wire, and endoluminal sheath, a suture, a braid, a trocar, a hernia mesh, a surgical mesh, a contact lens, an intra-ocular lens, a stent (for example vascular stent, esophageal stent, biliary stent coronary stent, renal stent, peripheral vascular stent), a nasal splint, a vascular graft, a stent-graft, aneurysm coils, introducer sheaths, balloon catheters, vascular closure devices, inferior vena cava filter, and Hydrocephalic shunts.

In one aspect, the derivatized polyhydric polymer of the disclosure can be prepared as a solution which can then be applied by spray coating or dip coating. The solvent can then be removed to leave a coating of the derivatized polyhydric polymer composition of the disclosure on the device surface. In one aspect, the solution can be an aqueous solution. In another aspect, the solution can comprise an organic solvent. In another aspect, the solution can comprise water and a water-miscible organic solvent. In one aspect the derivatized polyhydric polymer of the disclosure can be functionalized with aliphatic or aromatic groups such that there is a hydrophobic interaction with these groups and the device surface. In one aspect, the derivatized polyhydric polymer of this disclosure that has residual vinyl sulfone groups can be coated onto a medical device by dip coating or spray coating. The coating is dried. The coating can be exposed to heat, gamma, e-beam or ultraviolet radiation to crosslink the derivatized polyhydric polymer. In another aspect, the coating can further comprise a biologically active agent. In another aspect, the coating when hydrated, increase the lubricity of the coated device. The increased lubricity of the coated device can be measure by a decrease of the water contact angle by at least 20°. In another aspect, the increased lubricity can be measured as a decrease in the friction coefficient by at least 20%. In another aspect, the device can be partially coated with some part of the device remaining uncoated. In another aspect, the device can be precoated with binding polymer coating that enhances the binding of the coating derivatized polyhydric polymer composition of this disclosure. In another aspect, the coating can further comprise heparin, to give the coating anti-thrombotic properties.

A process for making a derivative polymer of a polyhydric polymer, comprising:
a) reacting hydroxyl groups of a polyhydric polymer, with divinyl sulfone (DVS) to provide a first polyhydric derivative; and b) reacting the first polyhydric polymer derivative with a nucleophile of a formula X'—R$^1$—Y, or X'—R$^2$—Y or both to provide a second polyhydric polymer derivative; wherein R$^1$ and R$^2$ are different, and each is a substituted or unsubstituted C$_1$-C$_{20}$ aliphatic or aromatic moiety, X' comprises a nucleophilic group of SH or NH$_2$, and Y is the same or different, and Y is one or more of H, a carboxylic acid group or a salt or ester thereof, a hydroxyl group, a sulfonic acid group or a salt thereof, or an amine group. This process, wherein the polyhydric polymer is hyaluronic acid (HA). This process may further comprise step c) derivatizing the second polyhydric polymer derivative by repeating, one or more times, step a) or step a) and step b).

The following Examples are offered by way of illustration and not by way of limitation. In the Examples, DI stands for distilled water, PEG stands for polyethylene glycol and IV stands for intrinsic viscosity.

EXAMPLES

Example 1

DVS Modified HA (DVS2)

2.5 g sodium hyaluronate (900 KDa) was added to a glass 4 L reaction kettle. The lid, overhead stirrer and anchor impellor were attached to the reaction kettle. The solution was then stirred at about 200 rpm. 250 g deionized water was added to the kettle. The solution was stirred for about 18 hrs. 166.5 g of a 0.25 M NaOH solution was added to the dissolved sodium hyaluronate. The pH of the solution was measured after 2 min and was found to be 12.69. A freshly prepared solution of 10.6 g divinyl sulfone in 66 g of DI water was then rapidly added to the stirring solution. After 75 seconds, 50 g of a 1M HCl solution was added to the reaction mixture. 1 M NaOH was then added dropwise until the solution pH was between 5 and 7. 6 g NaCl was then added to the solution. Once the NaCl had dissolved, 1.25 L acetone was slowly added over a period of 20 minutes. The suspension was stirred for about 3 hours. 200 mL denatured ethanol was added and the solution was stirred for about 30 minutes. The precipitate was filtered under vacuum using a sintered glass funnel through a 0.22 μm PTFE filter membrane. Once all the solution had been filtered, the vacuum was disconnected and 100 mL ethanol was used to rinse the precipitate. The ethanol was then removed by vacuum filtration. This process was repeated an additional 3 times. The product was dried under vacuum at room temp in a vacuum oven.

Approx. 10-20 mg of the dried sample was added to a vial. D$_2$O was added to the sample to make the final concentration of the solution about 6 mg/mL. The sample was shaken on an orbital shaker until dissolved. Once dissolved, the sample was transferred into a NMR tube and the $^1$H-NMR spectrum of the sample was recorded on a NMR spectrometer. The spectrum was printed out with the specific peaks in the 6.3-6.5 ppm (2 peaks from the 2 CH$_2$=protons from the vinyl sulfone residue), the 6.8-7.0 ppm (CH peak of vinyl group) and 1.8-2.5 ppm (singlet from the 3 CH$_3$ protons from the N-acetyl group of the HA) regions being integrated. The percent modification is calculated on molar ratio of the vinyl CH protons (6.8-7 ppm) to the acetamide (1.8-2.5 ppm) protons. The percent substitution was found to be about 8.9%. The $^1$H-NMR spectrum of the sample is shown in FIG. 1.

Example 2

DVS Modified HA (DVS13)

3.5 g sodium hyaluronate (approx. 800 kDa; 1.4 m3/Kg IV) was added to a 4 L glass reaction kettle. The lid, overhead stirrer and anchor impellor were attached to the reaction kettle. 350 g deionized water was added to the kettle. The solution was then stirred at about 300 rpm. The solution was stirred for about 18 hrs. The stirring speed was then increased to 750 rpm and about 233 g of a 0.25 M NaOH solution was added to the dissolved sodium hyaluronate. The pH of the solution was measured after 2 min and was found to be 12.95. A freshly prepared solution of 15.5 g divinyl sulfone in 92.4 g of DI water was then rapidly added to the stirring solution. After 4.5 minutes, 63 g of a 1 M HCl solution was added to the reaction mixture. 1 M NaOH was then added dropwise until the solution pH was between 5 and 7. 8.4 g NaCl was then added to the solution. Once the NaCl had dissolved, 1.5 L acetone was slowly added over a period of 30 minutes. The suspension was stirred for about 3 hours. 300 mL denatured ethanol was added and the solution was stirred for about 30 minutes. The precipitate was filtered under vacuum using a sintered glass funnel through a 0.22 μm PTFE filter membrane. Once all the solution had been filtered, the vacuum was disconnected and 150 mL ethanol was used to rinse the precipitate. The ethanol was then removed by vacuum filtration. This process was repeated an additional 3 times. The product was dried under vacuum at room temp in a vacuum oven. The percent substitution, as determined by the procedure described in Example 1, was found to be about 25%.

Example 3

DVS Modified HA (DVS14)

The reaction as described in Example 2 was performed using a reaction time of 6 minutes. The percent substitution, as determined according to the procedure described in Example 1, was found to be about 31%.

Example 4

HA-DVS Reaction with 3-Mercaptopropionic Acid (HA-DVS2-MPA)

0.5 g vinyl sulfone derivatized HA (approx. 9%, as per Example 1) was added to 50 g DI water in a 250 mL round bottom flask. The solution was stirred overnight until the material had dissolved. The flask was then purged with nitrogen. 0.022 g 3-mercaptopropionic acid (MPA) was added to the solution. After the MPA had dissolved, the pH was adjusted to about 9 using 0.25 M NaOH. The solution was stirred for 4 hours after which the pH was adjusted to about 7 using 0.25 M HCl. 1.25 g NaCl was added to the reaction solution. The solution was stirred until the NaCl had dissolved. 150 mL cold acetone was slowly added to the solution. The reaction mixture was stirred for 1.5 hours. 25 mL ethanol was added and the resultant mixture was stirred for 15 minutes. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of MPA substitution was evidenced by peaks at 2.3-2.4 ppm (triplet) and 2.6-2.8 ppm (triplet). The MPA substitution, as calculated from the integrals at 2.3-2.4 ppm (MPA-$CH_2$) and 1.7-2 ppm (HA-acetamide), was 7.6%.

Example 5

HA-DVS Reaction with 1-Octanethiol (HA-DVS2-Oct)

0.5 g vinyl sulfone derivatized HA (approx. 9%, as per Example 1) was added to 50 g DI water in a 250 mL round bottom flask. The solution was stirred for about 4 hours at room temperature. About 15.8 g denatured ethanol was added and the mixture was stirred for about 18 hrs at which point the material had dissolved. The flask was then purged with nitrogen. 0.023 g 1-octanethiol in 7.9 g ethanol was then added to the solution of derivatized HA. The pH of the reaction mixture was adjusted to about 9 using 0.25 M NaOH. The solution was stirred for 4 hours after which the pH was adjusted to about 7 using 0.25 M HCl. 0.5 g NaCl was added to the reaction solution. The solution was stirred until the NaCl had dissolved. 150 mL cold acetone was slowly added to the solution. The reaction mixture was stirred for 1.5 hours. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of octanethiol substitution was evidenced by peaks at 0.8-0-9 ppm (—$CH_3$), 1.2-1.6 ppm (—$CH_2$—), 2.6-2.7 ppm (—$CH_2$—S—) and 2.9-3.0 ppm (—S—$CH_2$—). The octanethiol molar substitution, as calculated from the integrals at 2.6-2.7 ppm. (Oct-$CH_2$—S—) and 1.7-2 ppm (HA-acetamide), was 5.4%.

Example 6

HA-DVS Reaction with 1-Octanethiol (HA-DVS2-Oct-DMF)

0.5 g vinyl sulfone derivatized HA (approx. 9%, as per Example 1) was added to 50 g DI water in a 250 mL round bottom flask. The solution was stirred for about 4 hours at room temperature. About 18.88 g dimethylformamide (DMF) was added and the mixture was stirred for about 18 hrs at which point the material had dissolved. The flask was then purged with nitrogen. 0.029 g 1-octanethiol in 9.4 g DMF was then added to the derivatized HA solution. The pH of the reaction mixture was adjusted to about 9 using 0.25 M NaOH. The solution was stirred for 4 hours after which the pH was adjusted to about 7 using 0.25 M HCl. About 0.25 g NaCl was added to the reaction solution. The solution was stirred until the NaCl had dissolved. 150 mL cold acetone was slowly added to the solution. The reaction mixture was stirred for 1.5 hours. 25 mL ethanol was added and the resultant mixture was stirred for 15 minutes. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The octanethiol molar substitution, as calculated from the integrals at 2.4-2.5 ppm (Oct-$CH_2$—S—) and 1.7-2 ppm (HA-acetamide), was 5.5%.

Example 7

HA-DVS Reaction with 1-dodecanethiol (HA-DVS2-dod)

0.5 g vinyl sulfone derivatized HA (approx. 9%, as per Example 1) was added to 50 g DI water in a 250 mL round bottom flask. The solution was stirred for about 4 hours at room temperature. About 15.8 g denatured ethanol was added and the mixture was stirred for about 18 hrs at which point the material had dissolved. The flask was then purged with nitrogen. 0.04 g 1-dodecanethiol in 7.9 g ethanol was then added to the solution of derivatized HA. The pH of the reaction mixture was adjusted to about 9 using 0.25 M NaOH. The solution was stirred for 4 hours after which the pH was adjusted to about 7 using 0.25 M HCl. 0.25 g NaCl was added to the reaction solution. The solution was stirred until the NaCl had dissolved. 150 mL cold acetone was slowly added to the solution. The reaction mixture was stirred for 1.5 hours. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1H$-NMR spectrum was measured. The presence of octanethiol substitution was evidenced by peaks at 0.8-0-9 ppm ($CH_3$—), 1.2-1.6 ppm (—$CH_2$—), 2.6-2.7 ppm (—$CH_2$—S—) and 2.9-3.0 ppm (—S—$CH_2$—). The octanethiol molar substitution, as calculated from the integrals at 2.6-2.7 ppm (Oct-$CH_2$—S—) and 1.7-2 ppm (HA-acetamide), was 5.2%.

Example 8

DVS Modified HA—Reaction 2 (DVS3)

3.5 g sodium hyaluronate (approx. 900 kDa, 17 dL/g) was added to a glass 4 L reaction kettle. The lid, overhead stirrer and anchor impellor were attached to the reaction kettle. 350 g deionized water was added to the kettle. The solution was stirred at about 200 rpm for about 18 hrs. 233 g of a 0.25 M NaOH solution was added to the dissolved sodium hyaluronate. The pH of the solution was measured after 2 min and was found to be 12.6. A freshly prepared solution of 14.8 g divinyl sulfone in 92.4 g of DI water was then rapidly added to the stirring solution. After 1.25 minutes, 70 g of 1M HCl was added to the reaction mixture. Either 1 M NaOH or 1M HCl was then added dropwise as needed until the solution pH was between 5 and 7. About 6 g NaCl was then added to the solution. Once the NaCl had dissolved, 1.25 L acetone was slowly added over a period of 20 minutes. The suspension was stirred for about 3 hours. 200 mL ethanol was added and the solution was stirred for about 30 minutes. The precipitate was filtered under vacuum using a sintered glass funnel through a 0.22 µm PTFE filter membrane. 100 mL ethanol was used to rinse the precipitate. The ethanol was then removed by vacuum filtration. This process was repeated an additional 3 times. The product was dried under vacuum at room temp in a vacuum oven. The percent substitution, determined as described in Example 1, was found to be 8.6%.

Example 9

DVS Modified HA-(DVS5-800 kDa)

3.5 g sodium hyaluronate (1.4 m3/kg, approx. 800 kDa) was added to a glass 4 L reaction kettle. The lid, overhead stirrer and anchor impellor were attached to the reaction kettle. 350 g deionized water was added to the kettle. The solution was stirred at about 200 rpm for about 18 hrs. 233 g of a 0.25 M NaOH solution was added to the dissolved sodium hyaluronate. The pH of the solution was measured after 2 min and was found to be 12.85. A freshly prepared solution of 14.8 g divinyl sulfone in 92.4 g of DI water was then rapidly added to the stirring solution. After 75 seconds, 63 g of a 1M HCl solution was added to the reaction mixture. Either 1M NaOH or 1M HCl was then added dropwise as needed until the solution pH was between 5 and 7. 8.4 g NaCl was then added to the solution. Once the NaCl had dissolved, 1.5 L acetone was slowly added over a period of 30 minutes. The suspension was stirred for about 3 hours. 200 mL ethanol (Ethanol, Alcohol Reagent, Denatured anhydrous 94-96%) was added and the solution was stirred for about 30 minutes. The precipitate was filtered under vacuum using a sintered glass funnel through a 0.22 µm PTFE filter membrane. 150 mL ethanol was used to rinse the precipitate. The ethanol was then removed by vacuum filtration. This process was repeated an additional 3 times. The product was dried under vacuum at room temp in a vacuum oven. The percent substitution, determined as described in Example 1, was found to be about 8.9%.

Example 10

HA-DVS Reaction with 1-pentanethiol (HA-DVS5-pent2)

0.5 g vinyl sulfone derivatized HA (approx. 9%, as per Example 9) was added to 27.5 g DI water in a 250 mL round bottom flask. The solution was stirred for about 4 hours at room temperature. About 16 g denatured ethanol was added and the mixture was stirred for about 18 hrs at which point the material had dissolved. The flask was then purged with nitrogen. 0.042 g 1-pentanethiol in about 1.8 g ethanol was then added to the solution of derivatized HA. The pH of the reaction mixture was adjusted to about 9 using 0.25 M NaOH. The solution was stirred for 4 hours after which the pH was adjusted to about 7 using 0.25 M HCl. About 0.5 g NaCl was added to the reaction solution. The solution was stirred until the NaCl had dissolved. 150 mL cold acetone was slowly added to the solution. The reaction mixture was stirred for 1.5 hours. The precipitate was isolated using vacuum filtration. The precipitate was washed 4 times with 25 mL ethanol in such a manner that the filter funnel did not run dry. The precipitate was dried under vacuum at room temperature. A sample was dissolved in $D_2O$ and the $^1H$-NMR spectrum was measured. The presence of pentanethiol substitution was evidenced by peaks at 0.6-0.8 ppm ($CH_3$—), 1.2-1.6 ppm (—$CH_2$—), 2.4-2.6 ppm (—$CH_2$—S—) and 2.7-2.9 ppm (—S—$CH_2$—). The pentanethiol molar substitution, as calculated from the integrals at 2.3-2.7 ppm (pent-$CH_2$—S—) and 1.7-2 ppm (HA-acetamide), was 7.3%.

Example 11

HA-DVS Reaction with 1-decanethiol (HA-DVS5-dec)

0.5 g vinyl sulfone derivatized HA (approx. 9%, as per Example 9) was added to 20 DI water in a 250 mL round bottom flask. The solution was stirred for about 4 hours at room temperature. 19.7 g denatured ethanol was added and the mixture was stirred for about 18 hrs at which point the material had dissolved. The flask was then purged with nitrogen. 0.035 g 1-decanethiol in 4 g ethanol was then added to the derivatized HA solution. The pH of the reaction mixture was adjusted to about 9 using 0.25 M NaOH. The solution was stirred for 4 hours after which the pH was adjusted to about 7 using 0.25 M HCl. 0.25 g NaCl was added to the reaction solution. The solution was stirred until the NaCl had dissolved. 150 mL cold acetone was slowly added to the solution. The reaction mixture was stirred for 1.5 hours. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of decanethiol substitution was evidenced by peaks at 0.6-0.8 ppm ($CH_3$—), 1.1-1.6 ppm (—$CH_2$—), 2.4-2.6 ppm (—$CH_2$—S—) and 2.7-2.9 ppm (—S—$CH_2$—). The decanethiol molar substitution, as calculated from the integrals at 2.3-2.7 ppm (pent-$CH_2$—S—) and 1.7-2 ppm (HA-acetamide), was 6.5%.

Example 12

HA-DVS Reaction with 3-mercapto-1-propanesulfonate (HA-DVS5-SMPS)

0.5 g vinyl sulfone derivatized HA (approx. 9%, as per Example 9) was added to 50 g DI water in a 250 mL round bottom flask. The solution was stirred overnight until the material had dissolved. The flask was then purged with nitrogen. 0.036 g sodium-3-mercapto-1-propanesulfonate (SMPS) was added to the solution. After the SMPS had dissolved, the pH was adjusted to about 9 using 0.25 M NaOH. The solution was stirred for 4 hours after which the pH was adjusted to about 7 using 0.25 M HCl. 1.25 g NaCl was added to the reaction solution. The solution was stirred until the NaCl had dissolved. 150 mL cold acetone was slowly added to the solution. The reaction mixture was stirred for 1.5 hours. 25 mL ethanol was added and the resultant mixture was stirred for 15 minutes. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of SMPS substitution was evidenced by peaks at 2.0-2.1 ppm (—$CH_2$—), 2.5-2.7 ppm (—$CH_2$—S—) and 2.8-3.0 ppm (—S—$CH_2$—). The SPMS substitution, as calculated from the integrals at 2.5-2.7 ppm (SMPS-$CH_2$—S—) and 1.7-2 ppm (HA-acetamide), was 6.4%.

Example 13

HA-DVS Reaction with Cysteine (HA-DVS5-cys)

0.5 g vinyl sulfone derivatized HA (approx. 9%, as per Example 9) was added to 50 g DI water in a 250 mL round bottom flask. The solution was stirred overnight until the material had dissolved. The flask was then purged with nitrogen. 0.024 g L-cysteine was added to the solution. After the cysteine had dissolved, the pH was adjusted to about 9 using 0.25 M NaOH. The solution was stirred for 4 hours after which the pH was adjusted to about 7 using 0.25 M HCl. 1.25 g NaCl was added to the reaction solution. The solution was stirred until the NaCl had dissolved. 150 mL cold acetone was slowly added to the solution. The reaction mixture was stirred for 1.5 hours. 25 mL ethanol was added and the resultant mixture was stirred for 15 minutes. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of cysteine substitution was evidenced by peaks at 2.8-3.0 ppm (—S—$CH_2$—). The cysteine substitution, as calculated from the integrals at 2.8-3.0 ppm (—$CH_2$—S—) and 1.7-2 ppm (HA-acetamide), was 4.9%.

Example 14

DVS Modified HA-Reaction 5 (DVS10-800 kDa)

5 g sodium hyaluronate (1.4 m3/kg, approx. 800 kDa) was added to a glass 4 L reaction kettle. The lid, overhead stirrer and anchor impellor were attached to the reaction kettle. 500 g deionized water was added to the kettle. The solution was stirred for about at about 200 rpm for 18 hrs. 333 g of a 0.25 M NaOH solution was added to the dissolved sodium hyaluronate. The pH of the solution was measured after 2 min and was found to be 12.93. A freshly prepared solution of 11 g divinyl sulfone in 66 g of DI water was then rapidly added to the stirring solution. After 2.5 minutes, 90 g of a 1M HCl solution was added to the reaction mixture. Either 1M NaOH or 1M HCl as needed was then added dropwise until the solution pH was between 5 and 7. About 12 g NaCl was then added to the solution. Once the NaCl had dissolved, 1.75 L acetone was slowly added over a period of 30 minutes. The suspension was stirred for about 3 hours. 300 mL ethanol (Ethanol, Alcohol Reagent, denatured anhydrous 94-96%) was added and the solution was stirred for about 30 minutes. The precipitate was filtered under vacuum using a sintered glass funnel through a 0.22 μm PTFE filter membrane. Once all the solution had been filtered, the vacuum was disconnected and 200 mL ethanol was used to rinse the precipitate. The ethanol was then removed by vacuum filtration. This process was repeated an additional 2 times. The product was dried under vacuum at room temp in a vacuum oven. The percent substitution, as determined according to the procedure described in Example 1, was found to be 8.1%.

Example 15

HA-DVS Reaction with 2-mercaptobenzoic acid (HA-DVS10-MBA)

0.5 g vinyl sulfone derivatized HA (approx. 8%, as per Example 14) was added to 27.5 g DI water in a 250 mL round bottom flask. The solution was stirred for about 4 hours at room temperature. 16 g denatured ethanol was added and the mixture was stirred for about 18 hrs at which point the material had dissolved. The flask was then purged with nitrogen and then placed in a water bath (temp=30±2° C.). 0.092 g 2-mercaptobenzoic acid (MBA) in 1.78 g ethanol was then added to the solution of derivatized HA. The pH of the reaction mixture was adjusted to about 9 using 0.25 M NaOH. The solution was stirred for 4 hours after which the pH was adjusted to about 7 using 0.25 M HCl. About 0.25 g NaCl was added to the reaction solution. The solution was stirred until the NaCl had dissolved. 150 mL cold acetone was slowly added to the solution. The reaction mixture was stirred for 1.5 hours. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of MBA substitution was evidenced by peaks at 7.1-7.5 ppm (Ar—H). The MBA molar substitution, as calculated from the integrals at 7.1-7.5 ppm (Ar—H) and 1.7-2 ppm (HA-acetamide), was 10%.

Example 16

HA-DVS Reaction with 4-methylbenzenethiol (HA-DVS10-MBT)

0.5 g vinyl sulfone derivatized HA (approx. 8%, as per Example 14) was added to 27.5 g DI water in a 250 mL round bottom flask. The solution was stirred for about 4 hours at room temperature. About 15.98 g denatured ethanol was added and the mixture was stirred for about 18 hrs at which point the material had dissolved. The flask was then purged with nitrogen and then placed in a water bath (temp=30±2° C.). 0.074 g 4-methylbenzenethiol (MBT) in about 1.78 g ethanol was then added to the solution of derivatized HA. The pH of the reaction mixture was adjusted to about 9.5 using 0.25 M NaOH. The solution was stirred for 4 hours after which the pH was adjusted to about 7 using 0.25 M HCl. About 0.25 g NaCl was added to the reaction solution. The solution was stirred until the NaCl had dissolved. 150 mL cold acetone was slowly added to the solution. The reaction mixture was stirred for 1.5 hours. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of MBT substitution was evidenced by peaks at 2.3-2.5 ppm (Ar—$CH_3$), 7.2-7.6 ppm (Ar—H). The MBT molar substitution, as calculated from the integrals at 7.1-7.5 ppm (Ar—H) and 1.7-2 ppm (HA-acetamide), was 5.0%.

Example 17

HA-DVS Reaction with 4-methoxy-α-toluenethiol (HA-DVS10-MTT)

0.5 g vinyl sulfone derivatized HA (approx. 8%, as per Example 14) was added to 27.5 g DI water in a 250 mL round bottom flask. The solution was stirred for about 4 hours at room temperature. 16 g denatured ethanol was added and the mixture was stirred for about 18 hrs at which point the material had dissolved. The flask was then purged with nitrogen and then placed in a water bath (temp=30±2° C.). About 0.092 g 4-methoxy-α-toluenethiol (MU) in 1.78 g ethanol was then added to the solution of derivatized HA. The pH of the reaction mixture was adjusted to about 9.5 using 0.25 M NaOH. The solution was stirred for 4 hours after which the pH was adjusted to about 7 using 0.25 M HCl. 0.25 g NaCl was added to the reaction solution. The solution was stirred until the NaCl had dissolved. 150 mL cold acetone was slowly added to the solution. The reaction mixture was stirred for 1.5 hours. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of MTT substitution was evidenced by peaks at 6.7-7.0 ppm (Ar—H), 7.1-7.3 ppm (Ar—H). The MTT molar substitution, as calculated from the integrals at 7.1-7.3 ppm (Ar—H) and 1.7-2 ppm (HA-acetamide), was 10.2%.

Example 18

HA-DVS Reaction with Thiophenol (HA-DVS10-thiophenol)

0.5 g vinyl sulfone derivatized HA (approx. 8%, as per Example 14) was added to 27.5 g DI water in a 250 mL round bottom flask. The solution was stirred for about 4 hours at room temperature. 16 g denatured ethanol was added and the mixture was stirred for about 18 hrs at which point the material had dissolved. The flask was then purged with nitrogen and then placed in a water bath (temp=30±2° C.). 0.066 g thiophenol in 1.78 g ethanol was then added to the solution of derivatized HA. The pH of the reaction mixture was adjusted to about 9.5 using 0.25 M NaOH. The solution was stirred for 4 hours after which the pH was adjusted to about 7 using 0.25 M HCl. About 0.25 g NaCl was added to the reaction solution. The solution was stirred until the NaCl had dissolved. 150 mL cold acetone was slowly added to the solution. The reaction mixture was stirred for 1.5 hours. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of thiophenol substitution was evidenced by peaks at 7.1-7.5 ppm (Ar—H). The thiophenol molar substitution, as calculated from the integrals at 7.1-7.5 ppm (Ar—H) and 1.7-2 ppm (HA-acetamide), was 7.6%.

Examples 19A and 19B

Effect of pH on HA-DVS Reaction with 1-pentanethiol (HA-DVS10-pent)

In each of Examples 19A and 19B, 0.5 g vinyl sulfone derivatized HA (approx. 7.5%, as per Example 14) was added to 27.5 g DI water in a 250 mL round bottom flask. The solution was stirred for about 4 hours at room temperature. 16 g denatured ethanol was added and the mixture was stirred for about 18 hrs at which point the material had dissolved. The flask was then purged with nitrogen and then placed in a water bath (temp=30±2° C.). About 0.062 g pentanethiol in about 1.78 g ethanol was then added to the solution of derivatized HA. In Example 19A, the pH was adjusted to about 8.5 while in Example 19B, the pH of the reaction mixture was adjusted to about 9.4 using 0.25 M NaOH. For both reactions, the solution was stirred for 4 hours after which the pH was adjusted to about 7 using 0.25 M HCl. 0.25 g NaCl was added to the reaction solution. The solution was stirred until the NaCl had dissolved. 150 mL cold acetone was slowly added to the solution. The reaction mixture was stirred for 1.5 hours. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of pentanethiol substitution was evidenced by peaks at 0.6-0.8 ppm ($CH_3$—), 1.2-1.6 ppm (—$CH_2$—), 2.4-2.6 ppm (—$CH_2$—S—) and 2.7-2.9 ppm (—S—$CH_2$—). The pentanethiol molar substitution, as calculated from the integrals at 2.3-2.7 ppm (pent-$CH_2$—S—) and 1.7-2 ppm (HA-acetamide), was 3.9% for pH 8.5 reaction and 6.7% for pH 9.5 reaction.

Example 20

DVS Modified HA-(DVS12-800 kDa)

3.5 g sodium hyaluronate (1.4 m3/kg, approx. 800 kDa) was added to a glass 4 L reaction kettle. The lid, overhead stirrer and anchor impellor were attached to the reaction kettle. 350 g deionized water was added to the kettle. The solution was stirred at about 750 rpm for about 18 hrs. About 233 g of a 0.25 M NaOH solution was added to the dissolved sodium hyaluronate. The pH of the solution was measured after 2 min and was found to be 12.91. A freshly prepared solution of 15.5 g divinyl sulfone in 92 g of DI water was then rapidly added to the stirring solution. After 3.25 minutes, 63 g of a 1M HCl solution was added to the reaction mixture. Either 1M NaOH or 1M HCl was then added dropwise as needed until the solution pH was between 5 and 7. About 8.4 g NaCl was then added to the solution. Once the NaCl had dissolved, 1.5 L acetone was slowly added over a period of 30 minutes. The suspension was stirred for about 3 hours. 300 mL ethanol (Ethanol, Alcohol Reagent, Denatured anhydrous 94-96%) was added and the solution was stirred for about 30 minutes. The precipitate was filtered under vacuum using a sintered glass funnel through a 0.22 μm PTFE filter membrane. Once all the solution had been filtered, the vacuum was disconnected and 150 mL ethanol was used to rinse the precipitate. The ethanol was then removed by vacuum filtration. This process was repeated an additional 3 times. The product was dried under vacuum at room temp in a vacuum oven. The percent substitution, as determined according to the procedure described in Example 1, was found to be about 22.2%.

Example 21

HA-DVS Reaction with 3-Mercaptopropionic Acid (HA-DVS12-MPA)

1.0 g vinyl sulfone derivatized HA (approx. 22%, as per Example 20) was added to 100 g DI water in a 250 mL round bottom flask. The solution was stirred overnight until the material had dissolved. The flask was then purged with nitrogen. 0.106 g 3-mercaptopropionic acid (MPA) was added to the solution. After the MPA had dissolved, the pH was adjusted to about 9 using 0.25 M NaOH. The solution was stirred for 4 hours after which the pH was adjusted to about 7 using 0.25 M HCl. 2.4 g NaCl was added to the reaction solution. The solution was stirred until the NaCl had dissolved. 300 mL cold acetone was slowly added to the solution. The reaction mixture was stirred for 1.5 hours. 50 mL ethanol was added and the resultant mixture was stirred for 15 minutes. The precipitate was isolated using vacuum filtration. The precipitate was washed 4 times with 50 mL ethanol in such a manner that the filter funnel did not run dry. The precipitate was dried under vacuum at room temperature. A sample of the material was dissolved in $D_2O$ and the $^1$H-NMR spectrum was measured. The presence of MPA substitution was evidenced by peaks at 2.4-2.6 ppm (—$CH_2$—COOH), 2.7-2.8 ppm (—$CH_2$—S—) and 2.9-3.1 ppm (—S—$CH_2$—). The MPA substitution, as calculated from the integrals at 2.4-2.6 ppm (MPA-$CH_2$) and 1.7-2 ppm (HA-acetamide), was 20.6%.

Example 22

DVS Modified HA-(DVS14-800 kDa)

3.5 g sodium hyaluronate (1.4 m3/kg, approx. 800 kDa) was added to a glass 4 L reaction kettle. The lid, overhead stirrer and anchor impellor were attached to the reaction kettle. 350 g deionized water was added to the kettle. The solution was stirred at about 750 rpm for about 18 hrs. 233 g of a 0.25 M NaOH solution was added to the dissolved sodium hyaluronate. The pH of the solution was measured after 2 min and was found to be 12.87. A freshly prepared solution of 15.5 g divinyl sulfone in 92 g of DI water was then rapidly added to the stirring solution. After 6 minutes, 63 g of a 1M HCl solution was added to the reaction mixture. Either 1M NaOH or 1M HCl was then added dropwise as needed until the solution pH was between 5 and 7. About 8.4 g NaCl was then added to the solution. Once the NaCl had dissolved, 1.5 L acetone was slowly added over a period of 30 minutes. The suspension was stirred for about 3 hours. 3 00 mL ethanol (Ethanol, Alcohol Reagent, denatured anhydrous 94-96%) was added and the solution was stirred for about 30 minutes. The precipitate was filtered under vacuum using a sintered glass funnel through a 0.22 μm PTFE filter membrane. 150 mL ethanol was used to rinse the precipitate. The ethanol was then removed by vacuum filtration. This process was repeated an additional 3 times. The product was dried under vacuum at room temp in a vacuum oven. The percent substitution, as determined by the procedure described in Example 1, was found to be 31.4%.

Example 23

HA-DVS Reaction with 2-mercaptobenzoic Acid (HA-DVS14-MBA)

Figure 4:
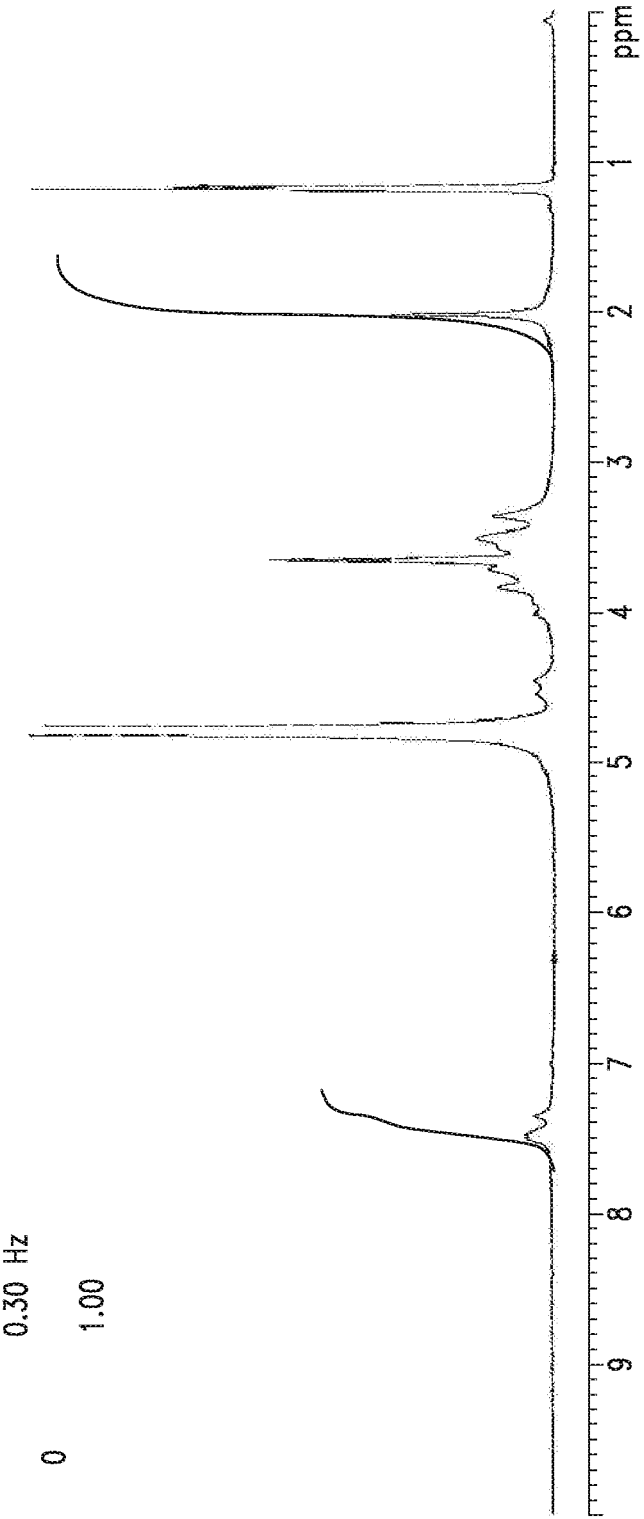
FIG. 4 shows a $^1$H-NMR spectrum of a 2-mercaptobenzoic acid (MBA) modified hyaluronic acid according to the present disclosure.

1.0 g vinyl sulfone derivatized HA (approx. 31%, as per Example 22) was added to 55 g DI water in a 500 mL round bottom flask. The solution was stirred for about 1 hour at room temperature. 32 g denatured ethanol was added and the mixture was stirred for about 18 hrs at which point the material had dissolved. The flask was then purged with nitrogen and then placed in a water bath (temp=30±2° C.). 0.554 g 2-mercaptobenzoic acid (MBA) in 3.55 g ethanol was then added to the derivatized HA solution. The pH of the reaction mixture was adjusted to about 9 using 0.25 M NaOH. The solution was stirred for 4 hours after which the pH was adjusted to about 7 using 0.25 M HCl. 1.32 g NaCl was added to the reaction solution. The solution was stirred until the NaCl had dissolved. 300 mL cold acetone was slowly added to the solution. The reaction mixture was stirred for 1.5 hours. The precipitate was isolated using vacuum filtration. The precipitate was washed 3 times with 50 mL ethanol in such a manner that the filter funnel did not run dry. The precipitate was dried under vacuum at room temperature. A sample of the material was dissolved in $D_2O$ and the $^1$H-NMR spectrum was measured. The presence of MBA substitution was evidenced by peaks at 7.1-7.5 ppm (Ar—H) [FIG. 4]. The MBA molar substitution, as calculated from the integrals at 7.1-7.5 ppm (Ar—H) and 1.7-2 ppm (HA-acetamide) was 35%.

Example 24

HA-DVS Reaction with Mercaptosuccinic Acid (HA-DVS14-MSA)

1.0 g vinyl sulfone derivatized HA (approx. 31%, as per Example 22) was added to 100 g DI water in a 500 mL round bottom flask. The solution was stirred for about 18 hrs at which point the material had dissolved. The flask was then purged with nitrogen. 0.18 g mercaptosuccinic acid (MSA) was then added to the derivatized HA solution. The pH of the reaction mixture was adjusted to about 9 using 0.25 M NaOH. The solution was stirred for 4 hours after which the pH was adjusted to about 7 using 0.25 M HCl. About 2.4 g NaCl was added to the reaction solution. The solution was stirred until the NaCl had dissolved. 300 mL cold acetone was slowly added to the solution. The reaction mixture was stirred for 1.5 hours. 50 mL ethanol was added and the mixture was stirred for 15 minutes. The precipitate was isolated using vacuum filtration. The precipitate was washed 4 times with 50 mL ethanol in such a manner that the filter funnel did not run dry. The precipitate was dried under vacuum at room temperature. A sample of the material was dissolved in $D_2O$ and the $^1$H-NMR spectrum was measured. The presence of MSA substitution was evidenced by peaks at 2.3 to 3.1 ppm. The MSA molar substitution, as calculated from the integrals at 3.0 ppm and 1.7-2 ppm (HA-acetamide) was 33%.

Example 25

HA-DVS Reaction with 9-mercapto-1-nonanol (HA-DVS14-nonanol)

1.0 g vinyl sulfone derivatized HA (approx. 31%, as per Example 22) was added to 55 g DI water in a 500 mL round bottom flask. The solution was stirred for about 1 hour at room temperature. 32 g denatured ethanol was added and the mixture was stirred for about 18 hrs at which point the material had dissolved. The flask was then purged with nitrogen and then placed in a water bath (temp=30±2° C.). 0.63 g 9-mercapto-1-nonanol in 3.55 g ethanol was then added to the solution of derivatized HA. The pH of the reaction mixture was adjusted to about 9 using 0.25 M NaOH. The solution was stirred for 4 hours after which the pH was adjusted to about 7 using 0.25 M HCl. 1.32 g NaCl was added to the reaction solution. The solution was stirred until the NaCl had dissolved. 300 mL cold acetone was slowly added to the solution. The reaction mixture was stirred for 1.5 hours. The precipitate was isolated using vacuum filtration. The precipitate was washed 3 times with 50 mL ethanol in such a manner that the filter funnel did not run dry. The precipitate was dried under vacuum at room temperature. A sample of the material was dissolved in $D_2O$ and the $^1$H-NMR spectrum was measured. The presence of nonanol substitution was evidenced by peaks at 1.1-1.8 ppm (—$CH_2$—), 2.5-2.8 ppm (—$CH_2$—S—) and 2.9-3.1 ppm (—S—$CH_2$—. The nonanol molar substitution, as calculated from the integrals at 2.5-2.8 ppm (—$CH_2$—S—) and 1.7-2 ppm (HA-acetamide), was 37.5%.

Example 26

DVS Reaction with 3-Mercaptopropionic Acid Derivatized HA

[HA-DVS12-MPA] (HA-MPA-DVS)

0.75 g MPA derivatized sodium hyaluronate (see Example 21) was added to a glass 4 L reaction kettle. The lid, overhead stirrer and anchor impellor were attached to the reaction kettle. 75 g deionized water was added to the kettle. The solution was stirred at about 750 rpm for about 18 hrs. 50 g of a 0.25 M NaOH solution was added to the dissolved sodium hyaluronate. The pH of the solution was measured to be 12.85. A freshly prepared solution of 3.3 g divinyl sulfone in 20 g of DI water was then rapidly added to the stirring solution. After 3.25 minutes, 13.5 g of a 1M HCl solution was added to the reaction mixture. Either 1M NaOH or 1M HCl was then added dropwise as needed until the solution pH was between 5 and 7. About 1.8 g NaCl was then added to the solution. Once the NaCl had dissolved, 300 mL acetone was slowly added over a period of 30 minutes. The suspension was stirred for about 3 hours. 50 mL ethanol was added and the solution was stirred for about 30 minutes. The precipitate was filtered under vacuum using a sintered glass funnel. Once all the solution had been filtered, the vacuum was disconnected and 150 mL ethanol was used to rinse the precipitate. The ethanol was then removed by vacuum filtration. This process was repeated an additional 3 times. The product was dried under vacuum at room temperature in a vacuum oven. The percent vinyl sulfone substitution, as determined according to the procedure described in Example 1, was found to be 10.1%.

Example 27

HA-MPA-DVS Reaction with 3-Mercaptopropionic Acid (HA-MPA^2-DVS^2)

0.5 g MPA/vinyl sulfone derivatized HA (see Example 26) was added to 50 g DI water in a 250 mL round bottom flask. The solution was stirred overnight until the material had dissolved. The flask was then purged with nitrogen. 0.048 g 3-mercaptopropionic acid (MPA) was added to the solution. After the MPA had dissolved, the pH was adjusted to about 9 using 0.25 M NaOH. The solution was stirred for 4 hours after which the pH was adjusted to about 7 using 0.25 M HCl. 1.2 g NaCl was added to the reaction solution. The solution was stirred until the NaCl had dissolved. 150 mL cold acetone was slowly added to the solution. The reaction mixture was stirred for 1.5 hours. 25 mL ethanol was added and the resultant mixture was stirred for 15 minutes. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1$H-NMR spectrum was measured. The presence of MPA substitution was evidenced by peaks at 2.4-2.6 ppm (—$CH_2$—COOH), 2.7-2.8 ppm (—$CH_2$—S—) and 2.9-3.1 ppm (—S—$CH_2$—). The MPA substitution, as calculated from the integrals at 2.4-2.6 ppm (MPA-$CH_2$) and 1.7-2 ppm (HA-acetamide) was 33%.

Example 28

DVS Reaction with Thiophenol Derivatized HA [HA-10-Thiophenol-DVS^2]

0.323 g MPA derivatized sodium hyaluronate (see Example 18) was added to a 250 mL round bottom flask. The overhead stirrer and anchor impellor were put in place. 4.62 g deionized water was added to the kettle. The solution was stirred at about 750 rpm for about 18 hrs. 23.48 g of a 0.25 M NaOH solution was added to the dissolved sodium hyaluronate derivative. The pH of the solution was measured to be 12.82. A freshly prepared solution of 0.775 g divinyl sulfone in 4.62 g of DI water was then rapidly added to the stirring solution. After 2.5 minutes, 6.15 g of a 1M HCl solution was added to the reaction mixture. Either 0.25M NaOH or 1M HCl was then added dropwise as needed until the solution pH was between 5 and 7. About 0.858 g NaCl was then added to the solution. Once the NaCl had dissolved, 125 mL acetone was slowly added over a period of 5 minutes. The suspension was stirred for about 3 hours. 25 mL ethanol was added and the solution was stirred for about 30 minutes. The precipitate was filtered under vacuum using a sintered glass funnel. Once all the solution had been filtered, 100 mL ethanol was used to rinse the precipitate. The ethanol was then removed by vacuum filtration. This process was repeated an additional 3 times. The product was dried under vacuum at room temperature in a vacuum oven. The percent vinyl sulfone substitution, as determined according to the procedure described in Example 1, was found to be 13.6%. The thiophenol peaks were observed in the 7.2-7.5 ppm.

Example 29

Crosslinking with a PEG-Dithiol Compound

Approx. 108 mg HA-10-thiophenol-DVS^2 [see Example 28] was weighed into a 20 mL glass scintillation vial. 7.2 mL deionized water was added and the sample was allowed to dissolve overnight. Approx. 65.64 mg PEG[3400]—(SH)2 [Sigma Aldrich] was added to a glass scintillation vial. 2.6 mL deionized water was added to the vial and the sample was mixed until dissolved. The PEG[3400]—(SH)2 solution was added to the HA-10-thiophenol-DVS^2 solution and the pH of the resultant solution was adjusted to greater than pH 10 (pH=10.71) using 0.25 M NaOH. The solution turned to a gel state.

Example 30

Crosslinking with Trimethylolpropane tris(3-mercaptopropionate) [TMP-SH]

Approx. 109 mg HA-10-thiophenol-DVS^2 [see Example 28] was weighed into a 20 mL glass scintillation vial. 7.29 mL deionized water was added and the sample was allowed to dissolve overnight. Approx. 6.1 mg trimethylolpropane tris(3-mercaptopropionate) [TMP-SH] [Sigma Aldrich] was added to a glass scintillation vial. 213 mL deionized water was added to the vial and the sample. The TMP-SH mixture was added to the HA-10-thiophenol-DVS^2 solution and the pH of the resultant solution was adjusted to greater than pH 11 (pH=11.31) using 0.25 M NaOH. The solution turned to a gel state.

Example 31

DVS Reaction with HA [HA-DVS-16-2]

10 g sodium hyaluronate (1.4 m3/kg, approx. 800 kD) was added to a glass 4 L reaction kettle. The lid, overhead stirrer and anchor impellor were attached to the reaction kettle. 1000 g deionized water was added to the kettle. The solution was stirred at about 300 rpm for about 18 hrs. 166.5 g of a 1 M NaOH solution was added to the dissolved sodium hyaluronate. The pH of the solution was measured after 2 min and was found to be greater than 12.5. A freshly prepared solution of 44.2 g divinyl sulfone in 250 g of DI water was then rapidly added to the stirring solution. After 8 minutes, 170 g of a 1M HCl solution was added to the reaction mixture. Either 1M NaOH or 1M HCl was then added dropwise as needed until the solution pH was between 5 and 7. About 24 g NaCl was then added to the solution. Once the NaCl had dissolved, 3 L acetone was slowly added over a period of 40 minutes. The suspension was stirred for about 3 hours. 500 mL ethanol was added and the solution was stirred for about 30 minutes. The precipitate was filtered under vacuum using a sintered glass funnel through a 0.22 μm PTFE filter membrane. Once all the solution had been filtered, the vacuum was disconnected and 200 mL ethanol was used to rinse the precipitate. The ethanol was then removed by vacuum filtration. This process was repeated an additional 3 times. The product was dried under vacuum at room temp in a vacuum oven. The percent substitution, as determined by the procedure described in Example 1, was found to be 72%.

Example 32

HA-DVS Reaction with 3-mercapto-1-propanesulfonate [HA-DVS-16-2-SMPS]

2.0 g vinyl sulfone derivatized HA (as per Example 31) was added to 200 g DI water in a 1 L reaction vessel. The solution was stirred (approx. 300 rpm) overnight until the material had dissolved. The flask was then purged with nitrogen. 1.28 g sodium-3-mercapto-1-propanesulfonate (SMPS) was added to the solution. After the SMPS had dissolved, the pH was adjusted to about 9 using 0.25 M NaOH. The solution was stirred for 4 hours after which the pH was adjusted to about 7 using 0.25 M HCl. 4.8 g NaCl was added to the reaction solution. The solution was stirred until the NaCl had dissolved. 300 mL cold acetone was slowly added to the solution. The reaction mixture was stirred for 1.5 hours. 75 mL ethanol was added and the resultant mixture was stirred for 15 minutes. The precipitate was isolated using vacuum filtration. The precipitate was washed 4 times with 75 mL ethanol in such a manner that the filter funnel did not run dry. The precipitate was dried under vacuum at room temperature. A sample of the material was dissolved in $D_2O$ and the $^1$H-NMR spectrum was measured. The presence of SMPS substitution was evidenced by peaks at 2.0-2.1 ppm (—$CH_2$—), 2.5-2.7 ppm (—$CH_2$—S—) and 2.8-3.0 ppm (—S—$CH_2$—). The SPMS substitution, as calculated from the integrals at 2.5-2.7 ppm (SMPS-$CH_2$—S—) and 1.7-2 ppm (HA-acetamide), was 82%.

Example 33

Crosslinking with Divinyl Sulfone—Single Component

Approx. 105 mg HA-DVS-16-2-SMPS [see Example 32] was weighed into a 20 mL glass scintillation vial. Approx. 2.3 mL deionized water was added to the vial and the sample was allowed to dissolve overnight. An additional 0.26 g DI water was added and the sample was mixed. The pH of the solution was adjusted to approximately pH 13 using 1M NaOH. Approximately 26 μL divinyl sulfone was added to the reaction mixture. The sample was mixed by vortexing and the reaction mixture was left at room temperature until a gel had formed. The gel was removed from the vial and placed in approx. 500 mL deionized water for 1 hour. The water was changed 2 times following an incubation time between 40 to 70 minutes. The water excess water was removed, the gel was transferred to a plastic container and the gel was frozen at −80° C. and then was lyophilized to produce a porous foam structure.

Example 34

Crosslinking with Divinyl Sulfone—Two Component 100 mg HA-DVS-16-2-SMPS [see Example 32] and 100 mg HA-DVS14-nonanol (see Example 25]) is weighed into a 20 mL glass scintillation vial. 5 mL deionized water is added to the vial and the sample is allowed to dissolve overnight. The pH of the solution is adjusted to approximately pH 13 using 1M NaOH. 52 μL divinyl sulfone is added to the reaction mixture. The sample is mixed by vortexing and the reaction mixture is left at room temperature until a gel forms. The gel is removed from the vial and is placed in 500 mL deionized water for 1 hour. The water is changed 2 times following incubation times between about 40 to 70 minutes. The water excess water is removed, the gel is transferred to a plastic container. A portion of the gel is frozen at −80° C. and is then lyophilized to produce a porous foam structure.

Example 35

Crosslinked Particles

Particles of the crosslinked hydrogels (representative examples include Examples 29, 30, 33 and 34) are prepared by passing the crosslinked derivatized polyhydric polymer gel composition through a mesh. The crosslinked gel is transferred to a 20 mL syringe. 5 mL saline or 10 mg/mL hyaluronic acid (approx. 800 kDa) is added to the syringe. The plunger is inserted into the syringe and the gel is extruded through a mesh (mesh with a pore size of approximately 500 μm that is held in a Polycarbonate Filter Holder, 25 mm). The extrusion process is repeated to produce gel particles.

Example 36

DVS Modified HA-(DVS18-800 kDa)

3.5 g sodium hyaluronate (IV=1.4 m3/kg, MW approx. 800 kD) was added to a glass 4 L reaction kettle. The lid, overhead stirrer and anchor impellor were attached to the reaction kettle. 350 g deionized water was added to the kettle. The solution was stirred at about 750 rpm for about 18 hrs. 233 g of a 0.25 M NaOH solution was added to the dissolved sodium hyaluronate. The pH of the solution was measured after 2 min and was found to be 12.92. A freshly prepared solution of 15.5 g divinyl sulfone in 92 g of DI water was then rapidly added to the stirring solution. After 15 minutes, 63 g of a 1M HCl solution was added to the reaction mixture. Either 1M NaOH or 1M HCl was then added dropwise as needed until the solution pH was between 5 and 7. About 8.4 g NaCl was then added to the solution. Once the NaCl had dissolved, 1.5 L acetone was slowly added over a period of 30 minutes. The suspension was stirred for about 3 hours. 300 mL ethanol (Ethanol, Alcohol Reagent, Denatured anhydrous 94-96%) was added and the solution was stirred for about 30 minutes. The precipitate was filtered under vacuum using a sintered glass funnel through a 0.22 μm PTFE filter membrane. Once all the solution had been filtered, the vacuum was disconnected and 150 mL ethanol was used to rinse the precipitate. The ethanol was then removed by vacuum filtration. This process was repeated an additional 3 times. The product was dried under vacuum at room temperature in a vacuum oven. The percent substitution, as determined by the procedure described in Example 1, was found to be 71.3%.

Example 37

HA-DVS Reaction with 3-Mercaptopropionic Acid (HA-DVS18-MPA)

1.0 g vinyl sulfone derivatized HA (approx. 71%, as per Example 36) was added to 100 g DI water in a 500 mL round bottom flask. The solution was stirred at 300 rpm overnight so that all of the material had dissolved. The flask was then purged with nitrogen. 0.25 g 3-mercaptopropionic acid (MPA) was added to the solution. After the MPA had dissolved, the pH was adjusted to about 9 using 0.25 M NaOH. The solution was stirred for 4 hours after which the pH was adjusted to about 7 using 0.25 M HCl. 2.4 g NaCl was added to the reaction solution. The solution was stirred until the NaCl had dissolved. 300 mL cold acetone was slowly added to the solution. The reaction mixture was stirred for 1.5 hours. 50 mL ethanol was added and the resultant mixture was stirred for 15 minutes. The precipitate was isolated using vacuum filtration. The precipitate was washed 4 times with 50 mL ethanol in such a manner that the filter funnel did not run dry. The precipitate was dried under vacuum at room temperature. A sample of the material was dissolved in $D_2O$ and the $^1H$-NMR spectrum was measured. The presence of MPA substitution was evidenced by peaks at 2.4-2.6 ppm ($-CH_2-COOH$), 2.7-2.8 ppm ($-CH_2-S-$) and 2.9-3.1 ppm ($-S-CH_2-$). The MPA substitution, as calculated from the integrals at 2.4-2.6 ppm (MPA-$CH_2$) and 1.7-2 ppm (HA-acetamide), was 79.4%.

Example 38

DVS Reaction with 3-Mercaptopropionic Acid Derivatized HA

[HA-18-MPA-DVS]

0.75 g MPA derivatized sodium hyaluronate (see Example 37) was added to a glass 4 L reaction kettle. The lid, overhead stirrer and anchor impellor were attached to the reaction kettle. 75 g deionized water was added to the kettle. The solution was stirred at about 200 rpm for about 18 hrs. 50 g of a 0.25 M NaOH solution was added to the dissolved sodium hyaluronate. The pH of the solution was measured to be 12.70. A freshly prepared solution of 3.3 g divinyl sulfone in 20 g of DI water was then rapidly added to the stirring solution. After 15 minutes, 13.5 g of a 1M HCl solution was added to the reaction mixture. Either 1M NaOH or 1M HCl was then added dropwise as needed until the solution pH was between 5 and 7. About 1.8 g NaCl was then added to the solution. Once the NaCl had dissolved, 300 mL acetone was slowly added over a period of 30 minutes. The suspension was stirred for about 3 hours. 50 mL ethanol was added and the solution was stirred for about 30 minutes. The precipitate was filtered under vacuum using a sintered glass funnel. Once all the solution had been filtered, the vacuum was disconnected and 150 mL ethanol was used to rinse the precipitate. The ethanol was then removed by vacuum filtration. This process was repeated an additional 3 times. The product was dried under vacuum at room temperature in a vacuum oven. The percent vinyl sulfone substitution, as determined according to the procedure described in Example 1, was found to be 66%.

Example 39

HA-MPA-DVS Reaction with 3-Mercaptopropionic Acid (HA-MPA^2-DVS^2)

0.5 g MPA/vinyl sulfone derivatized HA (see Example 38) was added to 50 g DI water in a 250 mL round bottom flask. The solution was stirred overnight, during which time the material dissolved. The flask was then purged with nitrogen. 0.175 g 3-mercaptopropionic acid (MPA) was added to the solution. After the MPA had dissolved, the pH was adjusted to about 9 using 0.25 M NaOH. The solution was stirred for 4 hours after which the pH was adjusted to about 7 using 0.25 M HCl. 1.2 g NaCl was added to the reaction solution. The solution was stirred until the NaCl had dissolved. 150 mL cold acetone was slowly added to the solution. The reaction mixture was stirred for 1.5 hours. 25 mL ethanol was added and the resultant mixture was stirred for 15 minutes. The precipitate was isolated using vacuum filtration. The precipitate was washed 4 times with 25 mL ethanol in such a manner that the filter funnel did not run dry. The precipitate was dried under vacuum at room temperature. A sample of the material was dissolved in $D_2O$ and the $^1H$-NMR spectrum was measured. The presence of MPA substitution was evidenced by peaks at 2.4-2.6 ppm ($-CH_2-COOH$), 2.7-2.8 ppm ($-CH_2-S-$) and 2.9-3.1 ppm ($-S-CH_2-$). The MPA substitution, as calculated from the integrals at 2.4-2.6 ppm (MPA-$CH_2$) and 1.7-2 ppm (HA-acetamide) was 133%.

Example 40

HA-Based Formulations

Various formulations, as shown in Table 1, are prepared where the numbers listed in Table 1 are weight percent values based on the total weight of a formulation. Each of the following HA derivatives may be used as the "HA derivative" listed in Table 1: (a) thiophenol derivative (representative example 28), (b) 2-mercaptobenzoic acid derivative (representative example 23), (c) mercaptosuccinic acid derivative (representative example 24), (d) sodium 3-mercapto-1-propanesulfonate derivative (representative example 32) and (e) decanethiol derivative (representative example 11). A portion of the gel samples is cast onto a glass sheet or a piece of release liner and allowed to dry at room temperature followed by vacuum drying for at least 12 hours. This produces a film of the formulation. A second portion of the gel samples are placed in a scintillation vial frozen at −80° C. and are then lyophilized. The formulations listed in Table 1 can also comprise 1% (w/w) collagen or gelatin as well as other excipients and buffers. Water or water for injection can be used instead of the saline.

TABLE 1

| Formulation | HA derivative | Gellan gum | Pluronics F127 | HPMC | CMC | PolyAA | Chitosan | Xantham gum | PEG400 | saline |
|---|---|---|---|---|---|---|---|---|---|---|
| 1 | 0.3 | 2 | — | — | — | — | — | — | — | 97.7 |
| 2 | 0.3 | — | 25 | — | — | — | — | — | — | 74.7 |
| 3 | 0.3 | — | — | 0.2 | — | — | — | — | — | 99.5 |
| 4 | 0.3 | — | — | — | 0.2 | — | — | — | — | 99.5 |
| 5 | 0.3 | — | — | — | — | 2.5 | — | — | — | 97.2 |
| 6 | 0.3 | — | — | — | — | — | 3 | — | — | 96.7 |
| 7 | 0.3 | — | — | — | — | — | — | 2 | — | 97.7 |
| 8 | 0.3 | 2 | — | — | — | — | — | — | 1 | 96.7 |
| 9 | 0.3 | — | 25 | — | — | — | — | — | 1 | 73.7 |
| 10 | 0.3 | — | — | 0.2 | — | — | — | — | 1 | 98.5 |
| 11 | 0.3 | — | — | — | 0.2 | — | — | — | 1 | 98.5 |
| 12 | 0.3 | — | — | — | — | 2.5 | — | — | 1 | 96.2 |
| 13 | 0.3 | — | — | — | — | — | 3 | — | 1 | 95.7 |
| 14 | 0.3 | — | — | — | — | — | — | 2 | 1 | 96.7 |
| 15 | 0.2 | 2 | 20 | — | — | — | — | — | — | 77.8 |
| 16 | 0.2 | — | 25 | 0.2 | — | — | — | — | — | 74.6 |
| 17 | 0.2 | — | 25 | — | — | 2 | — | — | — | 72.8 |
| 18 | 0.2 | — | 25 | — | 2 | — | — | — | — | 72.8 |
| 19 | 0.2 | — | 25 | — | — | — | 3 | — | — | 71.8 |
| 20 | 0.2 | — | 25 | — | — | — | — | 2 | — | 72.8 |
| 21 | 0.2 | 2 | 20 | — | — | — | — | — | 1 | 76.8 |
| 22 | 0.2 | — | 25 | 0.2 | — | — | — | — | 1 | 73.6 |
| 23 | 0.2 | — | 25 | — | — | 2 | — | — | 1 | 71.8 |
| 24 | 0.2 | — | 25 | — | 2 | — | — | — | 1 | 71.8 |
| 25 | 0.2 | — | 25 | — | — | — | 3 | — | 1 | 70.8 |
| 26 | 0.2 | — | 25 | — | — | — | — | 2 | 1 | 71.8 |
| 27 | 0.2 | — | — | — | — | — | — | — | — | 99.8 |

HPMC = hydroxypropyl methylcellulose
CMC = sodium carboxymethylcellulose
PolyAA = polyacrylic acid

Example 41

HA-Derivative Formulations

Various formulations, as shown in Table 2, of different HA derivatives, are prepared where the values listed under each ingredient are weight percent values based on the total weight of the formulation. A portion of the samples are cast onto a glass sheet or a piece of release liner using a Gardner knife and allowed to dry at room temperature followed by vacuum drying for at least 12 hours. This produces a film of the formulation. A second portion of the gel samples are placed in a scintillation vial frozen at −80° C. and are then lyophilized to produce a porous solid matrix. A third portion is kept in the solution/gel form. The formulations listed in Table 2 can also comprise 1% (w/w) collagen or gelatin as well as other excipients and buffers. Water or water for injection can be used instead of the saline.

TABLE 2

| Formulation | HA | thiophenol | 1 MBA | MSA | SMPS | Dec | saline |
|---|---|---|---|---|---|---|---|
| 1 | — | 0.2 | — | — | — | — | 99.8 |
| 2 | — | — | 0.2 | — | — | — | 99.8 |
| 3 | — | — | — | 0.2 | — | — | 99.8 |
| 4 | — | — | — | — | 0.2 | — | 99.8 |
| 5 | — | — | — | — | — | 0.2 | 99.8 |
| 6 | — | 0.1 | — | 0.1 | — | — | 99.8 |
| 7 | — | 0.1 | — | — | 0.1 | — | 99.8 |
| 8 | — | — | 0.1 | 0.1 | — | — | 99.8 |
| 9 | — | — | 0.1 | — | 0.1 | — | 99.8 |
| 10 | — | — | — | 0.1 | — | 0.1 | 99.8 |
| 11 | — | — | — | — | 0.1 | 0.1 | 99.8 |
| 12 | 0.1 | 0.1 | — | — | — | — | 99.8 |
| 13 | 0.1 | — | 0.1 | — | — | — | 99.8 |
| 14 | 0.1 | — | — | 0.1 | — | — | 99.8 |
| 15 | 0.1 | — | — | — | 0.1 | — | 99.8 |
| 16 | 0.1 | — | — | — | — | 0.1 | 99.8 |
| 17 | — | 0.1 | — | 0.1 | — | — | 99.8 |
| 18 | — | 0.1 | — | — | 0.1 | — | 99.8 |
| 19 | — | — | 0.1 | 0.1 | — | — | 99.8 |
| 20 | — | — | 0.1 | — | 0.1 | — | 99.8 |
| 21 | — | — | — | 0.1 | — | 0.1 | 99.8 |
| 22 | — | — | — | — | 0.1 | 0.1 | 99.8 |

Example 42

Biologically Active Agent Incorporation

Biologically active agents that are listed in Table 3 are incorporated directly into each of the formulations prepared in Examples 40 and 41. The formulations are prepared in either the gel form, a film form or a lyophilized form. Each formulation contains an active agent as listed in Table 3, in the amount as stated on a weight/weight (w/w) basis or units/gram (U/g) basis or μg/mL basis.

TABLE 3

| Biologically active agent | Amount in final formulation |
|---|---|
| Mitomycin C | 0.2% (w/w) |
| Paclitaxel | 0.1% (w/w) |
| Chlorhexidine gluconate | 2% (w/w) |
| Silver sulfadiazine | 1% (w/w) |
| Silver particles (200-400 nm) | 1.5% (w/w) |
| Lidocaine | 2% (w/w) |
| Bupivacaine | 1% (w/w) |
| Triamcinolone acetonide | 2% (w/w) |
| Triamcinolone hexacetonide | 2% (w/w) |
| Dexamethasone | 2% (w/w) |
| Botox | 5 U/g |
| BMP-7 | 0.5 μg/mL |
| Ciproflaxin | 6% (w/w) |

Example 43

Antibacterial Agent Incorporation

Clindamycin phosphate (1% [w/w]) or metronidazole (1.3% [w/w]) are incorporated directly into the formulations prepared in Example 40 and 41. In another set of formulations, a combination of clindamycin phosphate (0.5% [w/w]) or metronidazole (0.5% [w/w]) is incorporated directly into the formulations prepared in Example 40 and 41. In another set of formulations as prepared in Example 40 and 41, that contain either clindamycin phosphate (1% [w/w]) or metronidazole (1.3% [w/w]), the saline is replaced with a citrate/saline buffer to ensure the pH is maintained in the 4.5 to 6 pH range. The formulations are prepared in either the gel form, a film form or a lyophilized form.

Example 44

Rehydration with Biologically Active Agent

Lyophilized products can be prepared from formulations described in Examples 29, 30, 33, 34, 40 and 41. The lyophilized derivatized polyhydric polymer composition is rehydrated with either BMP-7 (5 μg/mL) or Botox (5 U/mL). The resultant gel is used as a gel and is applied to the tissue of a subject through topical application or through injection.

Example 45

Incorporation of Cells into Gel

Approx. 100 mg of a derivatized hyaluronic acid that contains residual vinyl sulfone groups (representative example as described in Example 28) is weighed into a 20 mL glass scintillation vial. 7 mL saline is added and the sample is allowed to dissolve overnight. Approx. 64 mg PEG[3400]—(SH)2 (Sigma Aldrich, St. Louis, MO, US) is added to a glass scintillation vial. 1.3 mL saline is added to the vial and the sample is mixed until dissolved. The PEG[3400]—(SH)2 solution is added to the derivatized HA sample solution and the pH of the resultant solution is adjusted to pH 8.5 a using 0.25 M NaOH. An aliquot of freshly trypsinized hMSCs cell suspension is mixed with the HA/PEG solution to provide a final cell concentration of 1, 5, 10 and 20×10$^6$ cells/mL. The samples are aliquoted into a 12 well plate. The samples are allowed to gel for 20 min in a 37° C. incubator. 2 mL fresh media is then added to each well.

Example 46

Incorporation of Gel into a Scaffold

Approx. 100 mg of a derivatized hyaluronic acid that contains residual vinyl sulfone groups (representative example as described in Example 28) is weighed into a 20 mL glass scintillation vial. 7 mL saline is added and the sample is allowed to dissolve overnight. Approx. 64 mg PEG[3400]—(SH)2 [Sigma Aldrich] is added to a glass scintillation vial. 1.3 mL saline is added to the vial and the sample is mixed until dissolved. The PEG[3400]—(SH)2 solution is added to the derivatized HA sample solution and the pH of the resultant solution is adjusted to pH 8.5 a using 0.25 M NaOH. The resultant solution is aliquoted onto a porous scaffold and is allowed to soak into the scaffold. Once the scaffold is saturated, the scaffold is placed in an incubator (37° C.) until the crosslinking reaction is completed. The porous scaffolds used for gel incorporation are an electrospun polydioxanone fabric and a 3D-printed polylactide scaffold with pores of approximately 200-500 μm.

Example 47

Incorporation of Gel/Cell Matrix into a Scaffold

A gel/cell matrix, as prepared in Example 45, is aliquoted onto a porous scaffold prior to gelation and is allowed to soak into the scaffold. Once the scaffold is saturated, the scaffold is placed in an incubator (37° C.) until the crosslinking reaction is completed. The porous scaffolds used for gel incorporation are an electrospun polydioxanone fabric and a 3D-printed polylactide-co-glycolide scaffold with pores of approximately 200-500 μm. The porous scaffold/hydrogel/cell complexes are placed in a well of a 12 well culture plate that contains fresh media Example 48

Electrospinning of HA-Derivative

A 15 mg/mL solution of a hyaluronic acid derivative is prepared by adding approximately 90 mg hyaluronic acid derivative to 3 mL deionized water. The sample is allowed to dissolve overnight. 3 mL dimethylformamide (DMF) is added to the sample and the sample is vortexed several times over a 30 minute period. The solution is transferred to a 5 mL syringe that has a needle tip with a 0.3 mm internal diameter. The syringe pump is set at 60 mL/min. The applied voltage is set at 22 kV with the distance from the tip to the collector being 15 cm. A piece of heavy aluminum foil is connected to the ground wire and the foils is submerged into a shallow bath that contains ethanol. The resulting electrospun derivatized polyhydric polymer composition is carefully removed and the sample is placed in the vacuum oven to remove residual solvent.

Example 49

Formation of Shaped Hydrogels

Approx. 100 mg of a derivatized hyaluronic acid that contained residual vinyl sulfone groups (representative example as described in Example 28) is weighed into a 20 mL glass scintillation vial. 7 mL saline is added and the sample is allowed to dissolve overnight. Approx. 64 mg PEG[3400]—(SH)2 [Sigma Aldrich] is added to a glass scintillation vial. 1.3 mL saline is added to the vial and the sample is mixed until dissolved. The PEG[3400]—(SH)2 solution is added to the derivatized HA sample solution and the pH of the resultant solution is adjusted to pH 8 a using 0.25 M NaOH. 30 mg of a drug (e.g., dexamethasone, triamcinolone acetonide, budesonide, flunisolide, ciproflaxin) was mixed into the solution. Using a syringe with a piece of silastic tubing of a known diameter attached to the needle, the solution is drawn up into the silastic tubing. Once the tubing is almost filled, the open end is bent over and held closed with a clamp. The tube is placed in an incubator (37° C.) overnight to complete the crosslinking reaction. The clamp is then removed and the gel in the tubing is dried in a vacuum oven. The dried crosslinked derivatized polyhydric polymer composition is removed from the tubing by carefully slicing the tubing. The dried crosslinked derivatized polyhydric polymer composition is then cut to the desired length (e.g. 2 to 4 mm and 1 to 2 cm). The solution preparation can use 60% (v/v) water and 40% (ethanol) in place of 100% water. Dried crosslinked derivatized polyhydric polymer composition without the drug are also prepared.

Example 50

Synthesis of Divinyl Sulfone Derivatized HA—Different Molecular Weights

The synthesis of divinyl sulfone derivatized HA using different starting HA molecular weights were performed using a similar method as described in Example 1. The specific molecular weights, reaction conditions and vinyl sulfone substitution obtained are as set forth in Table 4:

TABLE 4

|  | Rxn1 | Rxn1 | Rxn3 |
| --- | --- | --- | --- |
| Approx. Mw (kD) | 2,300 | 200 | 510 |
| HA (g) | 2.5 | 5 | 5 |
| Water (g) | 500 | 500 | 500 |
| DVS (g) | 10.6 | 21.2 | 21.2 |
| DVS water (g) | 66 | 132 | 132 |
| Stir speed (rpm) | 200-250 | 200-250 | 200-250 |
| Reaction pH | >12.5 | >12.5 | >12.5 |
| Reaction time (min) | 1.25 | 1.25 | 1.25 |
| NaCl (g) | 4 | 12 | 12 |
| Acetone (mL) | 2000 | 2000 | 1750 |
| Ethanol (mL) | 200 | 400 | 400 |
| Ethanol wash (mL) | 100 | 200 | 200 |
| Substitution (%) | 8.1 | 6.4 | 9.3 |

Example 51

DVS Reaction with HA-MSA (HA-DVS12-MSA-DVS)

0.75 g MPA derivatized sodium hyaluronate (see Example 24) was added to a 250 round bottom flask. An overhead stirrer and anchor impellor were attached to the reaction flask. 75 g deionized water was added to the kettle. The solution was stirred at about 750 rpm for about 18 hrs. 50 g of a 0.25 M NaOH solution was added to the dissolved sodium hyaluronate. The pH of the solution was measured to be about 12.8. A freshly prepared solution of 3.3 g divinyl sulfone in 20 g of DI water was then rapidly added to the stirring solution. After 3.25 minutes, 13.5 g of a 1M HCl solution was added to the reaction mixture. Either 1M NaOH or 1M HCl was then added dropwise as needed until the solution pH was between 5 and 7. About 1.8 g NaCl was then added to the solution. Once the NaCl had dissolved, 300 mL acetone was slowly added over a period of 30 minutes. The suspension was stirred for about 3 hours. 50 mL ethanol was added and the solution was stirred for about 30 minutes. The precipitate was filtered under vacuum using a sintered glass funnel. Once all the solution had been filtered, the vacuum was disconnected and 50 mL ethanol was used to rinse the precipitate. The ethanol was then removed by vacuum filtration. This process was repeated an additional 3 times. The product was dried under vacuum at room temperature in a vacuum oven. The percent vinyl sulfone substitution, as determined according to the procedure described in Example 1, was found to be 47.8%.

Example 52

MPA Reaction with HA-MSA-DVS (HA-DVS12-MSA-MPA)

0.5 g HA-MSA-DVS (Example 51) was added to 50 g DI water in a 250 mL round bottom flask. The solution was stirred for about 18 hrs at which point the derivatized polyhydric polymer had dissolved. The flask was then purged with nitrogen. 0.191 g 3-Mercaptopropionoic acid (MPA) was then added to the derivatized HA solution. The pH of the reaction mixture was adjusted to about 9 using 0.25 M NaOH. The solution was stirred for 4 hours after which the pH was adjusted to about 7 using 0.25 M HCl. About 1.8 g NaCl was added to the reaction solution. The solution was stirred until the NaCl had dissolved. 200 mL cold acetone was slowly added to the solution. The reaction mixture was stirred for 1.5 hours. 50 mL ethanol was added and the mixture was stirred for 15 minutes. The precipitate was isolated using vacuum filtration. The precipitate was washed 4 times with 25 mL ethanol in such a manner that the filter funnel did not run dry. The precipitate was dried under vacuum at room temperature. A sample of the derivatized polyhydric polymer was dissolved in $D_2O$ and the $^1$H-NMR spectrum was measured. The presence of MPA and MSA substitution was evidenced by peaks at 2.1 to 3.2 ppm.

Example 53

DVS Modified HA—HA-DVS-37

11.33 g sodium hyaluronate (1.4 m3/kg, approx. 800 kDa) was added to a glass 5 L reaction kettle. The lid, overhead stirrer and anchor impellor were attached to the reaction kettle. 1133 g deionized water was added to the kettle. The temperature controller for the Bioreactor heater (Chemglass CLS-1380-19V) was set to 25° C. The solution was stirred at about 300 rpm for approximately 18 hrs. The stirring speed was increased to 750 rpm. 35 g of a 1M NaOH solution was then added to the dissolved sodium hyaluronate. The pH of the solution was measured after 2 min and was found to be 12.5. The ph was adjusted to 12.32 using 1M HCl solution. A freshly prepared solution of 50 g divinyl sulfone in 282.5 g of DI water was then rapidly added to the stirring solution. The pH was monitored and adjusted with 1M NaOH to maintain pH range of 12.2-12.3 over the course of the reaction time of ten (10) minutes. After 10 minutes, 35 g of a 1M HCl solution was added to the reaction mixture and the pH of the reaction mixture was adjusted to a value between 5 and 7. About 19.5 g NaCl was then added to the solution. Once the NaCl had dissolved, 2 L acetone was slowly added over a period of <30 minutes. The suspension was stirred for about 3 hours. 400 mL ethanol was added and the solution was stirred for about 30 minutes. The precipitate was filtered under vacuum using a sintered glass funnel. Once all the solution had been filtered, the vacuum was disconnected and 200 mL ethanol was used to rinse the precipitate. The ethanol was then removed by vacuum filtration. This process was repeated an additional 3 times with each aliquot standing in static ethanol for five (5) minutes prior to applying vacuum. The product was used for reactions described below. The percent substitution was found to be 31% by the following NMR method. Approx. 10-20 mg of the dried sample was added to a vial. $D_2O$ was added to the sample to make the final concentration of the solution about 6 mg/mL. The sample was shaken on an orbital shaker until dissolved. Once dissolved, the sample was transferred into a NMR tube and the $^1$H-NMR spectrum of the sample was recorded on a NMR spectrometer. The spectrum was printed out with the specific peaks in the 6.0-6.4 ppm (2 peaks from the 2 $CH_2$=protons from the vinyl sulfone residue), the 6.6-7.0 ppm (CH peak of vinyl group) and 1.7-2.0 ppm (singlet from the 3 $CH_3$ protons from the N-acetyl group of the HA) regions being integrated. The percent modification is calculated on molar ratio of the vinyl CH protons (6.8-7 ppm) to the acetamide (1.7-2.0 ppm) protons.

Example 54

HA-DVS Reaction with Mercaptosuccinic Acid (MSA) (HA-DVS-37-MSA)

Figure 5:
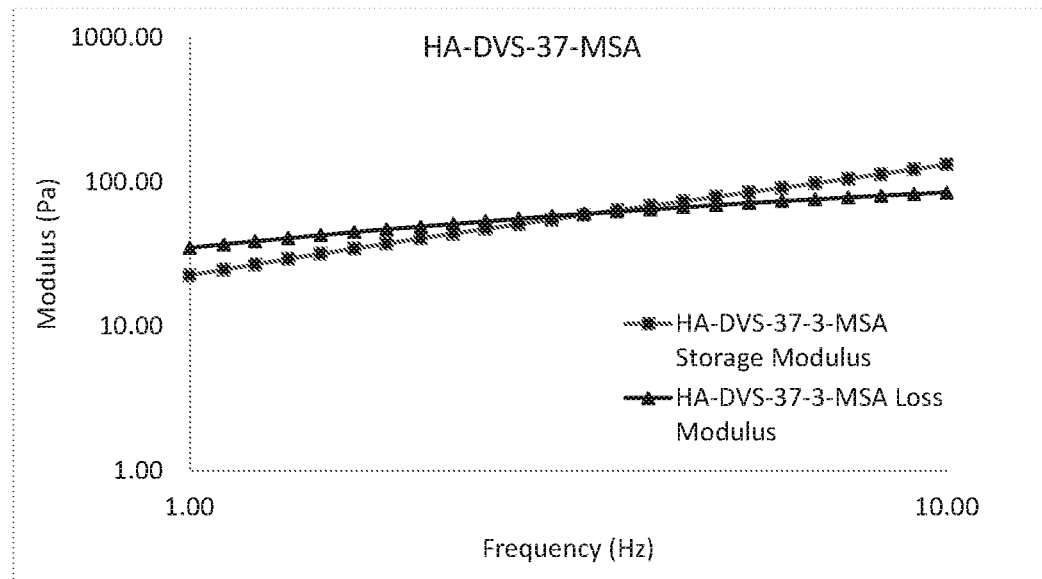
FIG. 5 is a graph showing a characteristic of an exemplary derivatized polymer disclosed herein.

The vinyl sulfone derivatized HA from Example 53 was added to 1200 g DI water in a 5 L reaction kettle. The temperature controller for the Bioreactor heater (Chemglass CLS-1380-19V) was set to 25° C. The solution was stirred for about 18 hrs at 300 rpm at which point the material had dissolved. The stirring speed was then increased to 500 rpm. 2.696 g mercaptosuccinic acid (MSA) was then added to the derivatized HA solution and allowed to stir for ten (10) minutes. The pH of the reaction mixture was adjusted to about 9 using 1 M NaOH. The solution was stirred for 4 hours after which the pH was adjusted to about 7 using 1M HCl. About 20.64 g NaCl was added to the reaction solution. The solution was stirred until the NaCl had dissolved. 2 L cold acetone was slowly added to the solution. The reaction mixture was stirred for 1.5 hours. 400 mL ethanol was added and the mixture was stirred for 15 minutes. The precipitate was isolated using vacuum filtration. Once all the solution had been filtered, the vacuum was disconnected and 200 mL ethanol was used to rinse the precipitate. The ethanol was then removed by vacuum filtration. This process was repeated an additional 3 times with each aliquot standing in static ethanol for five (5) minutes prior to applying vacuum. The product was dried under vacuum at room temp conditions. A sample of the material was dissolved in $D_2O$ and the $^1$H-NMR spectrum was measured. The presence of MSA substitution was evidenced by peaks at 2.3 to 3.1 ppm. The MSA molar substitution, as calculated from the integrals at 3.0 ppm and 1.7-2 ppm (HA-acetamide) was 20.6%. Rheology results for a 2% (w/v) solution were as following for flow viscosity (0.1-1000 1/s) and frequency testing (1-10 Hz). See Tables 5 and 6, and FIG. 5.

TABLE 5

| Shear Rate (1/s) | HA-DVS-37-3-MSA Average (cP) |
| --- | --- |
| 0.1 | 9510 |
| 1.15 | 8063 |
| 105 | 1136 |
| 1,000 | 215 |

TABLE 6

| | HA-DVS-37-3-MSA | |
| --- | --- | --- |
| Frequency | Storage Modulus Average | Loss Modulus Average |
| 10.00 | 132.33 | 84.67 |
| 4.96 | 78.87 | 69.13 |
| 2.46 | 47.30 | 53.53 |
| 1.00 | 22.57 | 35.00 |

Example 55

HA-DVS Reaction with Thiophenol (HA-DVS-37-THIO)

Figure 6:
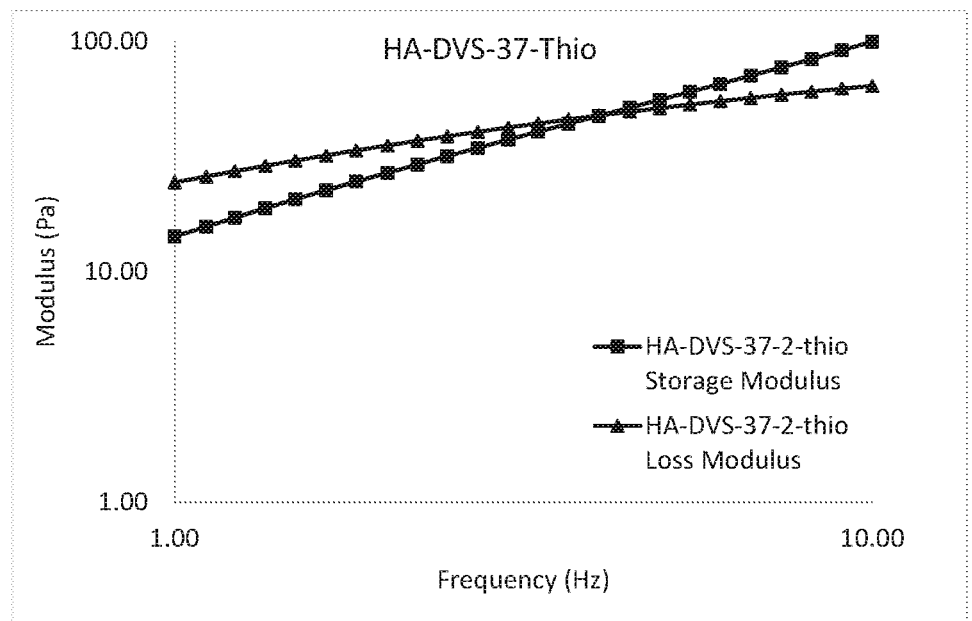
FIG. 6 is a graph showing a characteristic of an exemplary derivatized polymer disclosed herein.

The vinyl sulfone derivatized HA reaction product (produced in the same manner as Example 53) was added to 660 g DI water in a 5 L reaction kettle. The solution was stirred for about 1 hr at 300 rpm at 30° C. 426.06 g ethanol was then added and the solution was stirred for about 18 hrs at 300 rpm at 30° C. The stirring speed was then increased to 500 rpm. 5.935 g Thiophenol was then added to the derivatized HA solution and allowed to stir for ten (10) minutes. The pH of the reaction mixture was monitored and adjusted to about 9 using 1 M NaOH. The solution was stirred for 2 hours after which the pH was adjusted to about 7 using 1M HCl. About 9 g NaCl was added to the reaction solution. The solution was stirred until the NaCl had dissolved. 1 L cold acetone was slowly added to the solution. The reaction mixture was stirred for 1.5 hours. The precipitate was isolated using vacuum filtration. Once all the solution had been filtered, the vacuum was disconnected and 200 mL ethanol was used to rinse the precipitate. The ethanol was then removed by vacuum filtration. This process was repeated an additional 3 times with each aliquot standing in static ethanol for five (5) minutes prior to applying vacuum. The product was dried under vacuum at room temp conditions. A sample of the material was dissolved in $D_2O$ and the $^1$H-NMR spectrum was measured. The thiophenol peaks were observed in the 7.2-7.5 ppm. The thiophenol molar substitution was calculated at 32.8%. Rheology results for a 2% (w/v) solution were as following for flow viscosity (0.1-1000 1/s) and frequency testing (1-10 Hz). See Tables 7 and 8 and FIG. 6.

TABLE 7

| Shear Rate (1/s) | HA-DVS-37-2-THIO Average (cP) |
| --- | --- |
| 0.1 | 4003 |
| 1.15 | 3443 |
| 105 | 682 |
| 1,000 | 145 |

TABLE 8

| | HA-DVS-37-2-THIO | |
| --- | --- | --- |
| Frequency | Storage Modulus Average | Loss Modulus Average |
| 10.00 | 99.57 | 64.00 |
| 4.96 | 55.63 | 51.27 |
| 2.46 | 31.70 | 38.70 |
| 1.00 | 14.20 | 24.40 |

HA-DVS Reaction with Mercaptobenzoic Acid (MBA) (HA-DVS-37-MBA)

Figure 7:
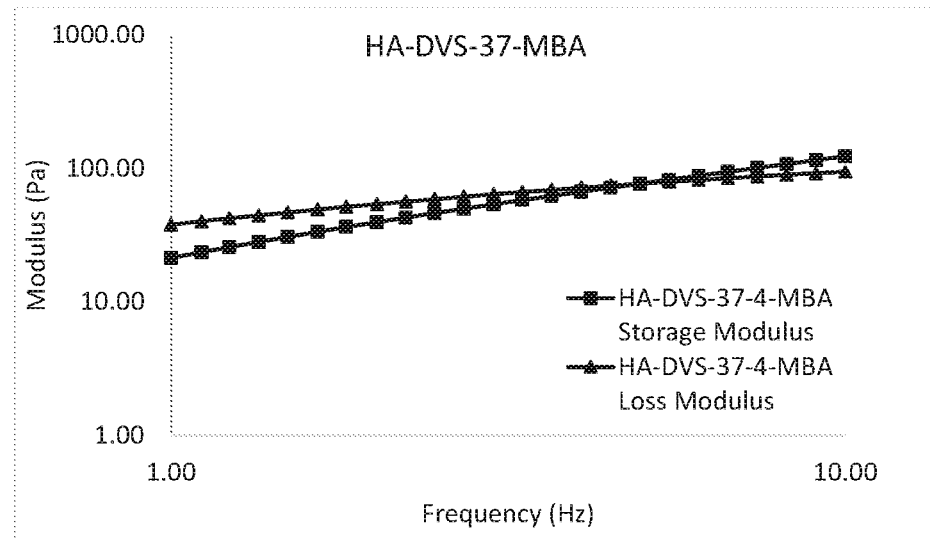
FIG. 7 is a graph showing a characteristic of an exemplary derivatized polymer disclosed herein.

The vinyl sulfone derivatized HA reaction (produced in the same manner as Example 53) was added to 660 g DI water in a 5 L reaction kettle. The solution was stirred for about 1 hr at 300 rpm at 30° C. 426.06 g Ethanol was then added and the solution was stirred for about 18 hrs at 300 rpm at 30° C. The stirring speed was then increased to 500 rpm. 8.305 g MBA was then added to the derivatized HA solution and allowed to stir for ten (10) minutes. The pH of the reaction mixture was monitored and adjusted to about 9 using 1 M NaOH. The solution was stirred for 2 hours after which the pH was adjusted to about 7 using 1M HCl. About 9 g NaCl was added to the reaction solution. The solution was stirred until the NaCl had dissolved. 1 L cold acetone was slowly added to the solution. The reaction mixture was stirred for 1.5 hours. The precipitate was isolated using vacuum filtration. Once all the solution had been filtered, the vacuum was disconnected and 200 mL ethanol was used to rinse the precipitate. The ethanol was then removed by vacuum filtration. This process was repeated an additional 3 times with each aliquot standing in static ethanol for five (5) minutes prior to applying vacuum. The product was dried under vacuum at room temp conditions. A sample of the material was dissolved in $D_2O$ and the $^1$H-NMR spectrum was measured. The presence of MBA substitution was evidenced by peaks at 7.1-7.5 ppm (Ar—H). The MBA molar substitution, as calculated from the integrals at 7.1-7.5 ppm (Ar—H) and 1.7-2 ppm (HA-acetamide), was 23.3%. Rheology results for a 2% (w/v) solution were as following for flow viscosity (0.1-1000 1/s) and frequency testing (1-10 Hz). See Tables 9 and 10, and FIG. 7.

TABLE 9

| Shear Rate (1/s) | HA-DVS-37-4-MBA Average (cP) |
| --- | --- |
| 0.1 | 9420 |
| 1.15 | 8167 |
| 105 | 1237 |
| 1,000 | 230 |

TABLE 10

| | HA-DVS-37-4-MBA | |
| --- | --- | --- |
| Frequency | Storage Modulus Average | Loss Modulus Average |
| 10.00 | 123.00 | 94.23 |
| 4.96 | 76.70 | 76.70 |
| 2.46 | 46.20 | 58.93 |
| 1.00 | 21.37 | 37.87 |

Example 57

HA-DVS Reaction with 3-mercapto-1-propanesulfonate (HA-DVS-37-SMPS)

Five (5) grams of vinyl sulfone derivatized HA (produced in the same manner as Example 53) was added to 500 g DI water in a 5 L reaction kettle. The temperature controller for the Bioreactor heater (Chemglass CLS-1380-19V) was set to 25° C. The solution was stirred for about 18 hrs at 300 rpm at which point the material had dissolved. The stirring speed was then increased to 500 rpm. 1.244 g 3-mercapto-1-propanesulfonate) was then added to the derivatized HA solution and allowed to stir for ten (10) minutes. The pH of the reaction mixture was adjusted to about 9 using 1 M NaOH. The solution was stirred for 4 hours after which the pH was adjusted to about 7 using 1M HCl. About 8.6 g NaCl was added to the reaction solution. The solution was stirred until the NaCl had dissolved. 750 ml cold acetone was slowly added to the solution. The reaction mixture was stirred for 1.5 hours. 150 mL ethanol was added and the mixture was stirred for 15 minutes. The precipitate was isolated using vacuum filtration. Once all the solution had been filtered, the vacuum was disconnected and 100 mL ethanol was used to rinse the precipitate. The ethanol was then removed by vacuum filtration. This process was repeated an additional 3 times with each aliquot standing in static ethanol for five (5) minutes prior to applying vacuum. The product was dried under vacuum at room temp conditions. A sample of the material was dissolved in $D_2O$ and the $^1$H-NMR spectrum was measured. The presence of SMPS substitution was evidenced by peaks at 2.0-2.1 ppm (—$CH_2$—), 2.5-2.7 ppm (—$CH_2$—S—) and 2.8-3.0 ppm (—S—$CH_2$—). The SMPS substitution, as calculated from the integrals at 2.5-2.7 ppm (SMPS-$CH_2$—S—) and 1.7-2 ppm (HA-acetamide), was 26.18%.

Example 58

DVS Modified HA—HA-DVS-36

11.33 g sodium hyaluronate (1.4 m3/kg, approx. 800 kDa) was added to a glass 5 L reaction kettle. The lid, overhead stirrer and anchor impellor were attached to the reaction kettle. 1133 g deionized water was added to the kettle. The temperature controller for the Bioreactor heater (Chemglass CLS-1380-19V) was set to 25° C. The solution was stirred at about 300 rpm for approximately 18 hrs. The stirring speed was increased to 750 rpm. 35 g of a 1M NaOH solution was then added to the dissolved sodium hyaluronate. The pH of the solution was measured after 2 min and was found to be 12.5. The ph was adjusted to 12.32 using 1M HCl solution. A freshly prepared solution of 50 g divinyl sulfone in 282.5 g of DI water was then rapidly added to the stirring solution. The pH was monitored and adjusted with 1M NaOH to maintain pH range of 12.2-12.3 over the course of the reaction time of twenty (20) minutes. After 20 minutes, 35 g of a 1M HCl solution was added to the reaction mixture and pH was adjusted to a value between 5 and 7. About 19.5 g NaCl was then added to the solution. Once the NaCl had dissolved, 2 L acetone was slowly added over a period of <30 minutes. The suspension was stirred for about 3 hours. 400 mL ethanol was added and the solution was stirred for about 30 minutes. The precipitate was filtered under vacuum using a sintered glass funnel. Once all the solution had been filtered, the vacuum was disconnected and 200 mL ethanol was used to rinse the precipitate. The ethanol was then removed by vacuum filtration. This process was repeated an additional 3 times with each aliquot standing in static ethanol for five (5) minutes prior to applying vacuum. The product was immediately dissolved for the reaction described in Example 59. The percent substitution was found to be 51.6% by the following NMR method. Approx. 10-20 mg of the dried sample was added to a vial. $D_2O$ was added to the sample to make the final concentration of the solution about 6 mg/mL. The sample was shaken on an orbital shaker until dissolved. Once dissolved, the sample was transferred into a NMR tube and the $^1$H-NMR spectrum of the sample was recorded on a NMR spectrometer. The spectrum was printed out with the specific peaks in the 6.0-6.4 ppm (2 peaks from the 2 $CH_2$=protons from the vinyl sulfone residue), the 6.6-7.0 ppm (CH peak of vinyl group) and 1.7-2.0 ppm (singlet from the 3 $CH_3$ protons from the N-acetyl group of the HA) regions being integrated. The percent modification is calculated on molar ratio of the vinyl CH protons (6.8-7.0 ppm) to the acetamide (1.7-2.0 ppm) protons.

Example 59

HA-DVS Reaction with Mercaptosuccinic acid (MSA) (HA-DVS-36-MSA)

Figure 8:
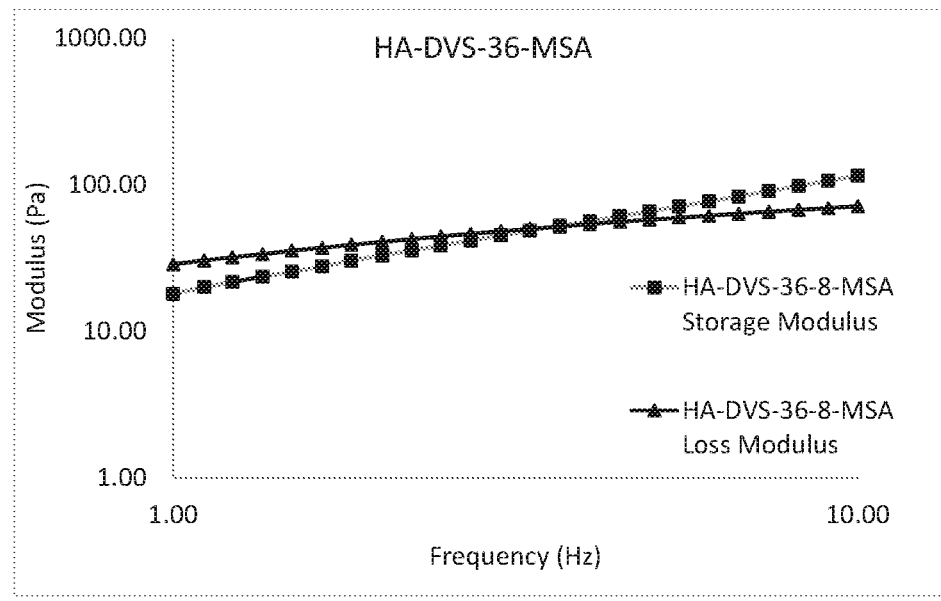
FIG. 8 is a graph showing a characteristic of an exemplary derivatized polymer disclosed herein.

The vinyl sulfone derivatized HA from Example 58 was added to 1200 g DI water in a 5 L reaction kettle. The temperature controller for the Bioreactor heater (Chemglass CLS-1380-19V) was set to 25° C. The solution was stirred for about 18 hrs at 300 rpm at which point the material had dissolved. The stirring speed was then increased to 500 rpm. 4.953 g mercaptosuccinic acid (MSA) was then added to the derivatized HA solution and allowed to stir for ten (10) minutes. The pH of the reaction mixture was adjusted to about 9 using 1 M NaOH. The solution was stirred for 4 hours after which the pH was adjusted to about 7 using 1M HCl. About 20.64 g NaCl was added to the reaction solution. The solution was stirred until the NaCl had dissolved. 2 L cold acetone was slowly added to the solution. The reaction mixture was stirred for 1.5 hours. 400 mL ethanol was added and the mixture was stirred for 15 minutes. The precipitate was isolated using vacuum filtration. Once all the solution had been filtered, the vacuum was disconnected and 200 mL ethanol was used to rinse the precipitate. The ethanol was then removed by vacuum filtration. This process was repeated an additional 3 times with each aliquot standing in static ethanol for five (5) minutes prior to applying vacuum. The product was dried under vacuum at room temp conditions. A sample of the material was dissolved in $D_2O$ and the $^1$H-NMR spectrum was measured. The presence of MSA substitution was evidenced by peaks at 2.3 to 3.1 ppm. The MSA molar substitution, as calculated from the integrals at 3.0 ppm and 1.7-2 ppm (HA-acetamide) was 33.2%. Rheology results for a 2% (w/v) solution were as following for flow viscosity (0.1-1000 1/s) and frequency testing (1-10 Hz). See Tables 11 and 12 and FIG. 8.

TABLE 11

| Shear Rate (1/s) | HA-DVS-36-MSA Average |
|---|---|
| 0.1 | 10667 |
| 1.15 | 8923 |
| 11 | 4503 |
| 105 | 1237 |
| 1,000 | 231 |

TABLE 12

| | HA-DVS-36-MSA | |
|---|---|---|
| Frequency | Storage Modulus Average | Loss Modulus Average |
| 10.00 | 115.33 | 71.50 |
| 4.96 | 65.77 | 57.87 |
| 2.46 | 38.50 | 44.40 |
| 1.00 | 18.07 | 28.73 |

Example 60

HA-DVS Reaction with Thiophenol (HA-DVS-36-THIO)

Figure 9:
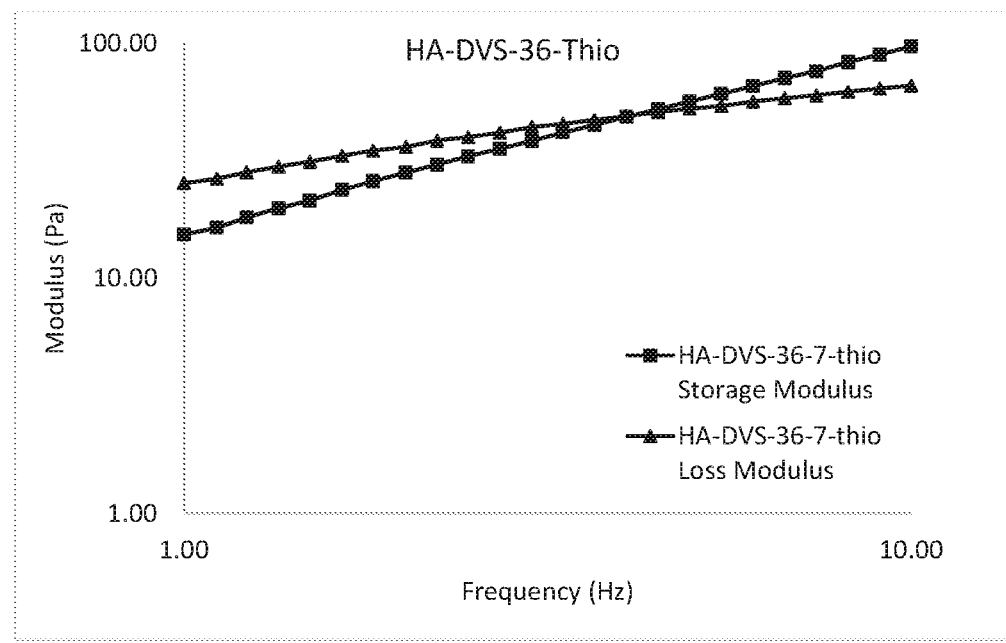
FIG. 9 is a graph showing a characteristic of an exemplary derivatized polymer disclosed herein.

The vinyl sulfone derivatized HA reaction product (produced in the same manner as Example 58) was added to 660 g DI water in a 5 L reaction kettle. The solution was stirred for about 1 hr at 300 rpm at 30° C. 426.06 g Ethanol was then added and the solution was stirred for about 18 hrs at 300 rpm at 30° C. The stirring speed was then increased to 500 rpm. 10.881 g Thiophenol was then added to the derivatized HA solution and allowed to stir for ten (10) minutes. The pH of the reaction mixture was monitored and adjusted to about 9 using 1 M NaOH. The solution was stirred for 2 hours after which the pH was adjusted to about 7 using 1M HCl. About 9 g NaCl was added to the reaction solution. The solution was stirred until the NaCl had dissolved. 1 L cold acetone was slowly added to the solution. The reaction mixture was stirred for 1.5 hours. The precipitate was isolated using vacuum filtration. Once all the solution had been filtered, the vacuum was disconnected and 200 mL ethanol was used to rinse the precipitate. The ethanol was then removed by vacuum filtration. This process was repeated with an additional 3 times with each aliquot standing in static ethanol for five (5) minutes prior to applying vacuum. The product was dried under vacuum at room temp conditions. A sample of the material was dissolved in $D_2O$ and the $^1$H-NMR spectrum was measured. The thiophenol peaks were observed in the 7.2-7.5 ppm. The thiophenol molar substitution was calculated at 50%. Rheology results for a 2% (w/v) solution were as following for flow viscosity (0.1-1000 1/s) and frequency testing (1-10 Hz). See Tables 13 and 14, and FIG. 9.

TABLE 13

| Shear Rate (1/s) | HA-DVS-36-thio Average (cP) |
|---|---|
| 0.1 | 8880 |
| 1.15 | 7467 |
| 11 | 3850 |
| 105 | 1090 |
| 1,000 | 209 |

TABLE 14

| | HA-DVS-36-Thio | |
|---|---|---|
| Frequency | Storage Modulus Average | Loss Modulus Average |
| 10.00 | 97.27 | 66.13 |
| 4.96 | 56.70 | 52.80 |
| 2.46 | 33.10 | 39.97 |
| 1.00 | 15.40 | 25.43 |

Example 61

HA-DVS Reaction with Mercaptobenzoic Acid (MBA) (HA-DVS-36-MBA)

Figure 10:
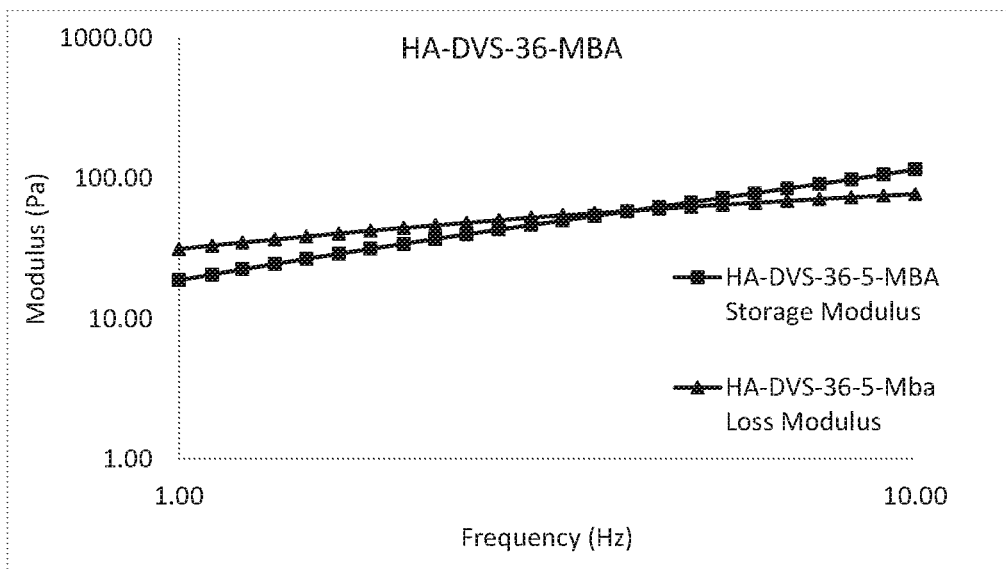
FIG. 10 is a graph showing a characteristic of an exemplary derivatized polymer disclosed herein.

The vinyl sulfone derivatized HA reaction product (produced in the same manner as Example 58) was added to 660 g DI water in a 5 L reaction kettle. The solution was stirred for about 1 hr at 300 rpm at 30° C. 426.06 g ethanol was then added and the solution was stirred for about 18 hrs at 300 rpm at 30° C. The stirring speed was then increased to 500 rpm. 15.227 g MBA was then added to the derivatized HA solution and allowed to stir for ten (10) minutes. The pH of the reaction mixture was monitored and adjusted to about 9 using 1 M NaOH. The solution was stirred for 2 hours after which the pH was adjusted to about 7 using 1M HCl. About 9 g NaCl was added to the reaction solution. The solution was stirred until the NaCl had dissolved. 1 L cold acetone was slowly added to the solution. The reaction mixture was stirred for 1.5 hours. The precipitate was isolated using vacuum filtration. Once all the solution had been filtered, the vacuum was disconnected and 200 mL ethanol was used to rinse the precipitate. The ethanol was then removed by vacuum filtration. This process was repeated an additional 3 times with each aliquot standing in static ethanol for five (5) minutes prior to applying vacuum. The product was dried under vacuum at room temp conditions. A sample of the material was dissolved in $D_2O$ and the $^1$H-NMR spectrum was measured. The presence of MBA substitution was evidenced by peaks at 7.1-7.5 ppm (Ar—H). The MBA molar substitution, as calculated from the integrals at 7.1-7.5 ppm (Ar—H) and 1.7-2 ppm (HA-acetamide), was 52.5%. Rheology results for a 2% (w/v) solution were as following for flow viscosity (0.1-1000 1/s) and frequency testing (1-10 Hz). See Table 15 and FIG. 10.

TABLE 15

| | HA-DVS-36-5-MBA | |
|---|---|---|
| Frequency | Storage Modulus Average | Loss Modulus Average |
| 10.00 | 116.00 | 77.50 |
| 4.96 | 67.67 | 63.03 |
| 2.46 | 40.07 | 48.53 |
| 1.00 | 18.90 | 31.47 |

Example 62

HA-DVS Reaction with 3-mercapto-1-propanesulfonate (HA-DVS-36-SMPS)

Figure 11:
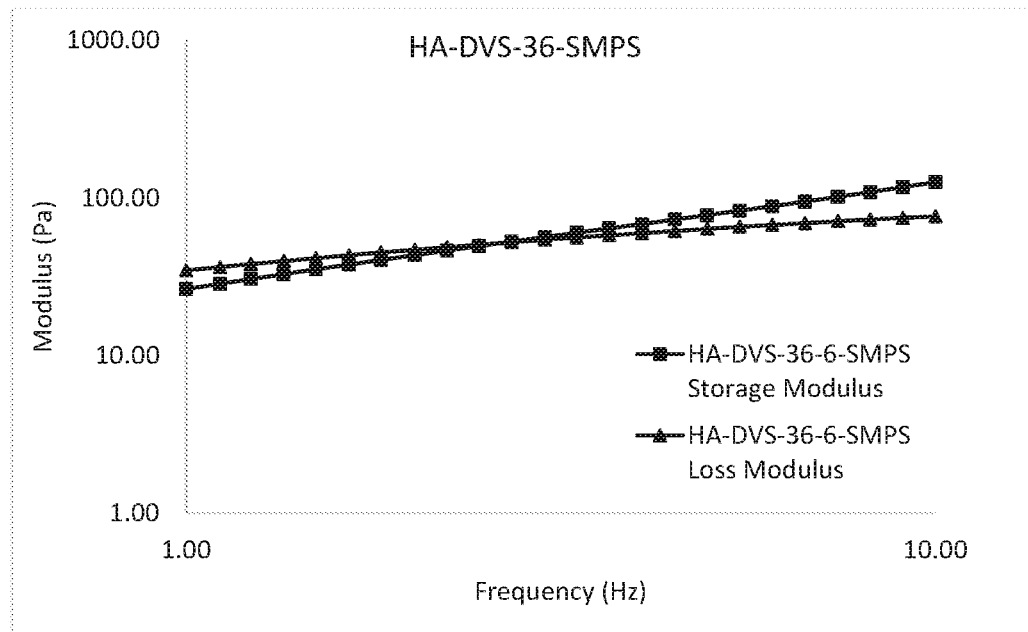
FIG. 11 is a graph showing a characteristic of an exemplary derivatized polymer disclosed herein.

The vinyl sulfone derivatized HA product (produced in the same manner as example 58) was added to 1200 g DI water in a 5 L reaction kettle. The temperature controller for the Bioreactor heater (Chemglass CLS-1380-19V) was set to 25° C. The solution was stirred for about 18 hrs at 300 rpm at which point the material had dissolved. The stirring speed was then increased to 500 rpm. 6.40 g 3-mercapto-1-propanesulfonate) was then added to the derivatized HA solution and allowed to stir for ten (10) minutes. The pH of the reaction mixture was adjusted to about 9 using 1 M NaOH. The solution was stirred for 4 hours after which the pH was adjusted to about 7 using 1M HCl. About 20.64 g NaCl was added to the reaction solution. The solution was stirred until the NaCl had dissolved. 2 L cold acetone was slowly added to the solution. The reaction mixture was stirred for 1.5 hours. 400 mL ethanol was added and the mixture was stirred for 15 minutes. The precipitate was isolated using vacuum filtration. Once all the solution had been filtered, the vacuum was disconnected and 200 mL ethanol was used to rinse the precipitate. The ethanol was then removed by vacuum filtration. This process was repeated an additional 3 times with each aliquot standing in static ethanol for five (5) minutes prior to applying vacuum. The product was dried under vacuum at room temp conditions. A sample of the material was dissolved in $D_2O$ and the $^1$H-NMR spectrum was measured. The presence of SMPS substitution was evidenced by peaks at 2.0-2.1 ppm (—$CH_2$—), 2.5-2.7 ppm (—$CH_2$—S—) and 2.8-3.0 ppm (—S—$CH_2$—). The SMPS substitution, as calculated from the integrals at 2.5-2.7 ppm (SMPS-$CH_2$—S—) and 1.7-2 ppm (HA-acetamide), was 54.3%. Rheology results for a 2% (w/v) solution were as following for flow viscosity (0.1-1000 1/s) and frequency testing (1-10 Hz). See Tables 16 and 17 and FIG. 11.

TABLE 16

| Shear Rate (1/s) | HA-DVS-36-SMPS Average (cP) |
|---|---|
| 0.1 | 9673 |
| 1.15 | 7433 |
| 11 | 3443 |
| 105 | 951 |
| 1,000 | 190 |

TABLE 17

| | HA-DVS-36-SMPS | |
|---|---|---|
| Frequency | Storage Modulus Average | Loss Modulus Average |
| 10.00 | 126.13 | 76.53 |
| 4.96 | 77.77 | 63.73 |
| 2.46 | 49.50 | 50.63 |
| 1.00 | 26.43 | 34.73 |

Example 63

DVS Modified HA—HA-DVS-37 L Lot 1 with Lower MW Sodium Hyaluronate 11.33 g sodium hyaluronate (0.62 m3/kg) was added to a glass 5 L reaction kettle. The lid, overhead stirrer and anchor impellor were attached to the reaction kettle. 1133 g deionized water was added to the kettle. The temperature controller for the Bioreactor heater (Chemglass CLS-1380-19V) was set to 25° C. The solution was stirred at about 300 rpm for approximately 18 hrs. The stirring speed was increased to 750 rpm. 30 g of a 1M NaOH solution was then added to the dissolved sodium hyaluronate. The pH of the solution was measured after 2 min and was found to be 12.26. The ph was adjusted to 12.30 using 1M HCl solution. A freshly prepared solution of 50 g divinyl sulfone in 282.5 g of DI water was then rapidly added to the stirring solution. The pH was monitored and adjusted with 1M NaOH to maintain pH range of 12.2-12.3 over the course of the reaction time of ten (10) minutes. After 10 minutes, 27 g of a 1M HCl solution was added to the reaction mixture and pH was adjusted to a value between 5 and 7. About 19.5 g NaCl was then added to the solution. Once the NaCl had dissolved, 2 L acetone was slowly added over a period of <30 minutes. The suspension was stirred for about 3 hours. 500 mL ethanol was added and the solution was stirred for about 30 minutes. An additional 500 ml of cold acetone was added to ensure everything had precipitated. The precipitate was filtered under vacuum using a sintered glass funnel through a 0.22 µm PTFE filter membrane. Once all the solution had been filtered, the vacuum was disconnected and 200 mL ethanol was used to rinse the precipitate. The ethanol was then removed by vacuum filtration. This process was repeated an additional 3 times with each aliquot standing in static ethanol for five (5) minutes prior to applying vacuum. The product was immediately dissolved for the reaction described in Example 64. The percent substitution, as determined by the following NMR method, was found to be 25.1%. Approx. 10-20 mg of the dried sample was added to a vial. $D_2O$ was added to the sample to make the final concentration of the solution about 6 mg/mL. The sample was shaken on an orbital shaker until dissolved. Once dissolved, the sample was transferred into a NMR tube and the ¹H-NMR spectrum of the sample was recorded on a NMR spectrometer. The spectrum was printed out with the specific peaks in the 6.0-6.4 ppm (2 peaks from the 2 $CH_2$=protons from the vinyl sulfone residue), the 6.6-7.0 ppm (CH peak of vinyl group) and 1.7-2.0 ppm (singlet from the 3 $CH_3$ protons from the N-acetyl group of the HA) regions being integrated. The percent modification is calculated on molar ratio of the vinyl CH protons (6.8-7 ppm) to the acetamide (1.7-2.0 ppm) protons.

Example 64

HA-DVS Reaction with Thiophenol (HA-DVS-37 L-THIO)

Figure 12:
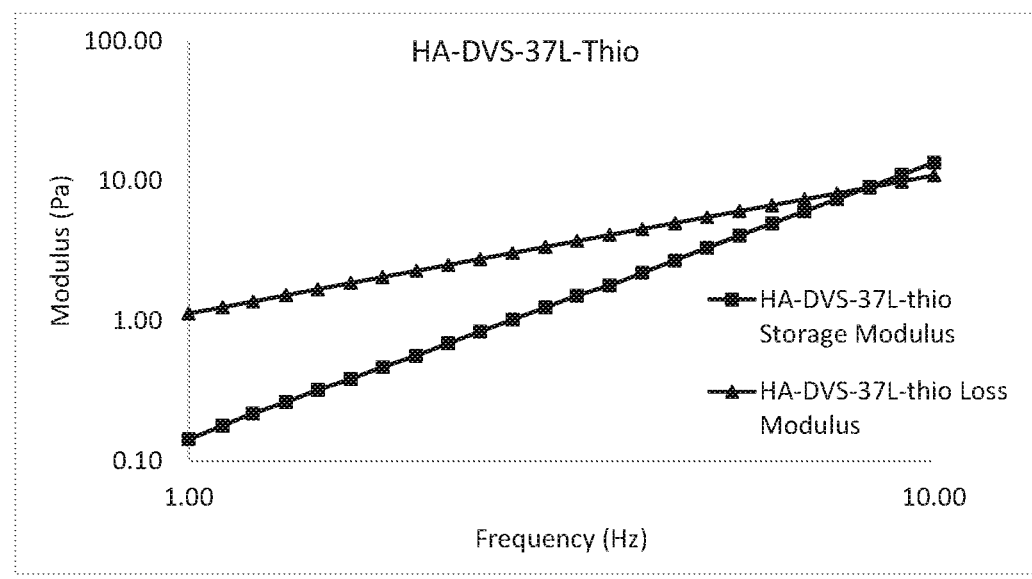
FIG. 12 is a graph showing a characteristic of an exemplary derivatized polymer disclosed herein.

The vinyl sulfone derivatized HA reaction product described in Example 63 was added to 660 g DI water in a 5 L reaction kettle. The solution was stirred for about 1 hr at 300 rpm at 30° C. 426.06 g ethanol was then added and the solution was stirred for about 18 hrs at 300 rpm at 30° C. The stirring speed was then increased to 500 rpm. 5.935 g Thiophenol was then added to the derivatized HA solution and allowed to stir for ten (10) minutes. The pH of the reaction mixture was monitored and adjusted to about 9 using 1 M NaOH. The solution was stirred for 2 hours after which the pH was adjusted to about 7 using 1M HCl. About 9 g NaCl was added to the reaction solution and stirred until the NaCl had dissolved. 1 L cold acetone was slowly added to the solution. The reaction mixture was stirred for 1.5 hours. The precipitate was isolated using vacuum filtration. Once all the solution had been filtered, the vacuum was disconnected and 200 mL ethanol was used to rinse the precipitate. The ethanol was then removed by vacuum filtration. This process was repeated an additional 3 times with each aliquot standing in static ethanol for five (5) minutes prior to applying vacuum. The product was dried under vacuum at room temp conditions. A sample of the material was dissolved in $D_2O$ and the ¹H-NMR spectrum was measured. The thiophenol peaks were observed in the 7.2-7.5 ppm. The thiophenol molar substitution was calculated at 24.4%. Rheology results for a 2% (w/v) solution were as following for flow viscosity (0.1-1000 1/s) and frequency testing (1-10 Hz). See Tables 18 and 19 and FIG. 12.

TABLE 18

| Shear Rate (1/s) | HA-DVS-37L-Thio Average (cP) |
|---|---|
| 0.1 | 1154 |
| 1.15 | 218 |
| 11 | 200 |
| 1,000 | 123 |

TABLE 19

| | HA-DVS-37L-thio | |
|---|---|---|
| Frequency | Storage Modulus Average | Loss Modulus Average |
| 10.00 | 13.50 | 10.97 |
| 4.96 | 3.33 | 5.51 |
| 2.46 | 0.84 | 2.77 |
| 1.00 | 0.14 | 1.13 |

Example 65

Concentration Effect on Rheological Properties of Sodium Hyaluronate Derivatives Sodium Hyaluronate (Shiseido 1.4 m3/kg, approx. 800 kDa) and the derivatives described in Examples 54, 55, 56, 60, 61, 62, and 63 were dissolved in deionized $H_2O$ into 2% (w/v), 1% (w/v), and 0.5% (w/v) solutions. Flow curve viscosity (0.1-1000 1/s) testing was performed to produce the following results.

TABLE 20

Flow Curve Viscosity Values of Derivatives described in Examples 54, 55, and 56

| | Viscosity (cP) | | | Viscosity (cP) | | | Viscosity (cP) | | |
|---|---|---|---|---|---|---|---|---|---|
| Frequency (1/s) | HA-DVS-37-MBA 2% | HA-DVS-37-MBA 1% | HA-DVS-37-MBA 0.5% | HA-DVS-37-Thio 2% | HA-DVS-37-Thio 1% | HA-DVS-37-Thio 0.5% | HA-DVS-37-MSA 2% | HA-DVS-37-MSA 1% | HA-DVS-37-MSA 0.5% |
| 0.1 | 9420 | 807 | 86 | 4003 | 869 | 94 | 9510 | 1162 | 108 |
| 1.15 | 8167 | 991 | 176 | 3443 | 937 | 160 | 8063 | 1237 | 195 |
| 11 | 4330 | 775 | 165 | 2067 | 715 | 146 | 4063 | 872 | 180 |
| 105 | 1237 | 339 | 100 | 682 | 307 | 87 | 1136 | 352 | 101 |
| 1,000 | 230 | 89 | 36 | 145 | 81 | 31 | 215 | 90 | 34 |

TABLE 21

Flow Curve Viscosity Values of Derivatives described in Examples 59, 60, 61 and 62

| | Viscosity (cP) | | | Viscosity (cP) | | |
|---|---|---|---|---|---|---|
| Frequency (1/s) | HA-DVS-36-MBA 2% | HA-DVS-36-MBA 1% | HA-DVS-36-MBA 0.5% | HA-DVS-36-SMPS 2% | HA-DVS-36-SMPS 1% | HA-DVS-36-SMPS 0.5% |
| 0.1 | 16667 | 849 | 208 | 9673 | 1487 | 158 |
| 1.15 | 11893 | 864 | 204 | 7433 | 1460 | 272 |
| 11 | 5590 | 644 | 169 | 3443 | 924 | 218 |
| 105 | 1453 | 275 | 95 | 951 | 341 | 108 |
| 1,000 | 262 | 74 | 32 | 190 | 86 | 35 |

TABLE 21-continued

Flow Curve Viscosity Values of Derivatives
described in Examples 59, 60, 61 and 62

| | Viscosity (cP) | | | Viscosity (cP) | | |
|---|---|---|---|---|---|---|
| Frequency (1/s) | HA-DVS-36-Thio 2% | HA-DVS-36-Thio 1% | HA-DVS-36-Thio 0.5% | HA-DVS-36-MSA 2% | HA-DVS-36-MSA 1% | HA-DVS-36-MSA 0.5% |
| 0.1 | 8880 | 782 | 151 | 10667 | 794 | 175 |
| 1.15 | 7467 | 813 | 183 | 8923 | 882 | 205 |
| 11 | 3850 | 617 | 163 | 4503 | 661 | 178 |
| 105 | 1090 | 269 | 94 | 1237 | 281 | 99 |
| 1,000 | 209 | 73 | 33 | 231 | 75 | 34 |

REFERENCE TABLE 22

Sodium Hyaluronate (Shiseido 1.4 m3/kg, approx. 800 kDa)

| Frequency | Viscosity (cP) | | |
|---|---|---|---|
| (1/s) | HA 2% | HA 1% | HA 0.5% |
| 0.1 | 11,500 | 1413 | 16 |
| 1.15 | 10,500 | 1543 | 242 |
| 11 | 6,110 | 1113 | 227 |
| 105 | 1810 | 433 | 125 |
| 1,000 | 332 | 102 | 40 |

Example 66

Ultraviolet Curing as Crosslinking Mechanism for Hyaluronic Acid

Functionalized HA-DVS polymers synthesized in methods disclosed herein (e.g., Example 58) with ~50% derivatization was diluted to a 2% (w/v) solution in DI water and allowed to dissolve overnight. This solution was combined with photoinitiator at a loading percentage of 2.5% with either 1) 2-Hydroxy-4(2-hydroxyethoxy)-2-methylpropiohenone (Irgacure 2959, Sigma-Aldrich Corp., St. Louis, MO, USA) 2) Irgacure 2959 (Sigma-Aldrich Corp., St. Louis, MO, USA) dissolved in ethanol or 3) Omnirad 380 P1108420 (Phenylbis(2,4,6-trimethylbenzoyl)phosphine oxide; Sigma-Aldrich Corp., St. Louis, MO, USA). Each sample was mixed using a mixer, Flacktek DAC 150.1 FVZ-K (Flacktek, Inc, 1708 Hwy. 11 Bldg. G|Landrum, SC 29356), with 2 cycles of mixing each of duration 30 sec at 2000 rpm. Solutions were clamped between glass plates with 1⁄32"-3⁄32" spaces and placed under ultraviolet light (365 nm longwave UV) for ten (10) minute intervals.

Example 67

Ultraviolet Curing as Crosslinking Mechanism for Hyaluronic Acid and Hyaluronic Based Derivatives Functionalized HA-DVS polymers, were synthesized as disclosed herein, for example, Example 58, with ~50% derivation and reacted with mercaptobenzoic acid produced in similar methods to Example 61 (HA-DVS-16-MBA) and was diluted to a 4% (w/v) solution in DI water and allowed to dissolve overnight. The dissolved solution was combined in the following HA-DVS to HA-DVS-MBA volume ratios: 25/75, 50/50 and 75/25 and mixed using the Flacktek DAC 150.1 FVZ-K with 2 cycles of mixing each of duration 30 sec at 2000 rpm. The photoinitiator Irgacure 2959 was tested at 2.5% and 7.5% loading for both the 75/25 and 25/75 ratios. The photoiniator TPO-L (Ethyl (2,4,6-trimethylbenzoyl) phenylphosphinate, BASF Corporation, 1609 Biddle Avenue, Wyandotte, MI 48192, USA) was tested at 7.5% for the 75/25 and 25/75 ratios. Solutions were clamped between glass plates with 1⁄32"-3⁄32" spacers and placed under ultraviolet light (365 nm longwave UV) for ten (10) minute intervals. Crosslinked films were produced.

Example 68

Cell Culture of Primary Human Dermal Fibroblasts

Primary human dermal fibroblasts (HDFs) (ATCC PCS-201-012, American Type Culture Collection, Manassas, VA, US) were cultured in Fibroblast Basal Medium (PCS-201-030) supplemented with Fibroblast growth kit-low serum (ATCC PCS-201-041) and Penicillin-Streptomycin-Amphotericin B solution (ATCC PCS-999-02). The fibroblast growth kit-low serum constituents and final concentration were: L-glutamine: (7.5 mM), rh FGF basic (5 ng/mL), rh Insulin (5 µg/mL), Hydrocortisone (1 µg/mL), ascorbic acid (50 µg/mL), and fetal bovine serum (2%). HDFs were cultured for a minimum of five (5) days prior to cell passaging/seeding for experimentation purposes. The cell passaging procedure consisted of rinsing cell flasks for two (2) times with Dulbeco's phosphate buffered saline (1×, DPBS, ATCC 30-2200). Trypsin/EDTA Solution (ATCC PCS-999-003) was then applied for 4-8 minutes incubated at 37° C. until the majority of cells had dislodged from the flask surface. Trypsin Neutralizing Solution (ATCC PCS-999-004) was then applied to the solution and the entire amount centrifuged for five (5) minutes. The trypsin/neutralizing solution was then aspirated and the pellet resuspended in medium. An aliquot of the resuspended cell solution was diluted with Trypan Blue (0.4% solution) (Gibco 15250061) at a ratio of 1:1 and counted using a hemocytometer to determine the initial cell concentration.

Example 69

Figure 13:
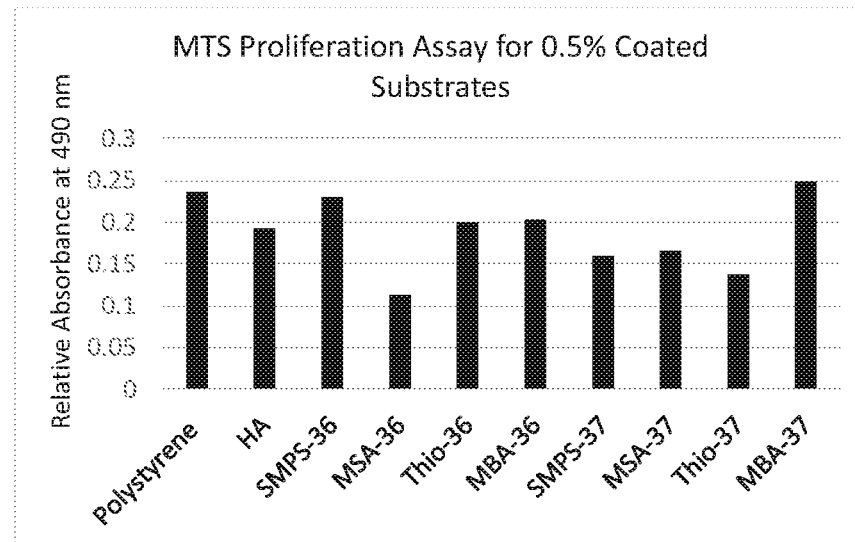
FIG. 13 is a graph showing cellular growth on exemplary derivatized polymers disclosed herein.

Polystyrene cell plates (48 wells) were coated with either 2%, 1% or 0.5% solutions of deionized H2O and Sodium Hyaluronate or the polymer derivatives described in Examples 54, 55, 56, 57, 59, 60, 61, and 62. The plates were allowed to dry for 24-48 hours under laminar flow conditions. The sodium hyaluronate and derivatives as described herein were then crosslinked with 2% FeCl$_3$ solution in deionized H2O for 5-15 minutes and rinsed with Dulbecco's Phosphate Buffered Saline DPBS. The resulting films were allowed to dry under laminar flow conditions for an additional 12-24 hours. Isopropyl alcohol (IPA) was applied to the films and then rinsed with DPBS to remove any residual IPA. Human dermal fibroblasts (HDFs) cultured and passaged as described in Example 68 were seeded at a concentration of 2.5×104 cells/ml. The HDFs were cultured for five days after which CellTiter 96® AQueous One Solution Cell Proliferation Assay (MTS, Promega, Madison WI) was applied in order to indirectly measure the metabolic activity the viable cells. The relative absorbance level was measured at 490 nm on the BioTek ELx808 microplate reader and represented in FIG. 13. Results indicated HDF presence and cell viability support of sodium hyaluronate derivatives.

Example 70

Figure 14:
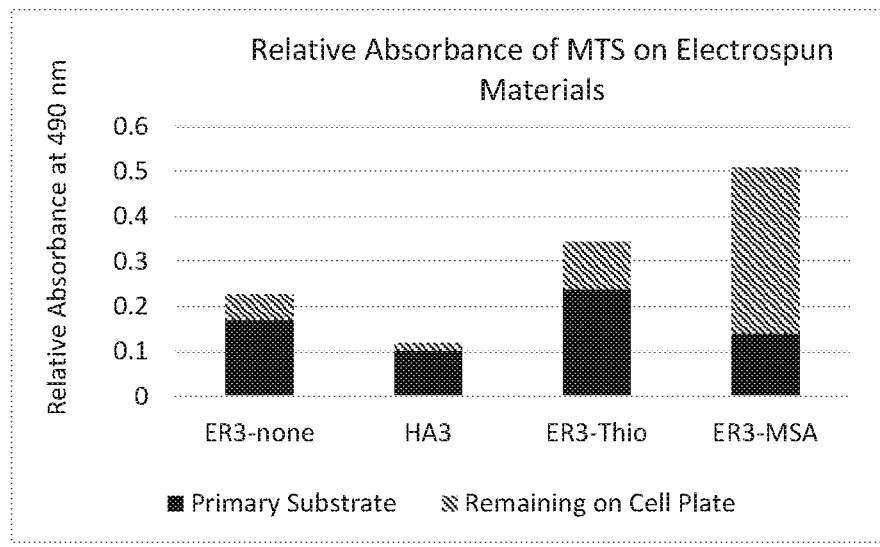
FIG. 14 is a graph showing cellular growth on electrospun articles comprising exemplary derivatized polymers disclosed herein.

Co-spun (Poly(lactic-co-glycolic acid) (PLGA) (Purasorb PLG1017) and polydioxanone (PDO) (Resomer X 206S) electrospun substrates were coated with 2% (w/v) solutions with either sodium hyaluronate (Shiseido 1.4 m3/kg, approx. 800 kDa, Shiseido Co., Ltd. Frontier Science Business Division, 1-6-2 Higashi-shimbashi, Minato-ku, Tokyo 105-8310, Japan), sodium hyaluronate derivatized with thiophenol (THIO) as described herein, or sodium hyaluronate derivatized with mercaptosuccinic acid (MSA), as described herein. The coated electrospun matrices were allowed to dry at atmospheric conditions and then were crosslinked using a 2% (w/v) solution of FeCl3 and deionized H2O. Samples of the electrospun matrices were placed for five (5) minutes in 2% FeCl3 solution on an orbital shaker and then They were then transferred to DPBS and rinsed twice for five minutes each prior to drying. Control electrospun material without coating was treated under the same cross-linking conditions. After drying, the electrospun samples were punched into ~0.95 cm2 samples and rinsed in 100% isopropyl alcohol and then rinsed again in DPBS and allowed to dry under a sterile laminar hood. The samples were then placed within 48 well polystyrene cell plates and hydrated with 100 µl DPBS and seeded with cells at 1×104 cells/ml and incubated at 37º C, 5% CO2 cell culture conditions for seven (7) days. Analysis included CellTiter 96® AQueous One Solution Cell Proliferation Assay (MTS, Promega, Madison WI) for both 1) the electrospun substrate which was transferred to another plate in order to isolate the cells attached to the electrospun substrate and 2) the cells remaining on the polystyrene surface that had migrated or proliferated onto the polystyrene well during the seven (7) day incubation period. See FIG. 14. Additionally, for the case of the electrospun substrates, phalloidin (phalloidin-tetramethylrhodamine B isothiocyanate) (Sigma Aldrich P-1951, St. Louis MO) staining for f-actin with DAPI (4',6-diamidino-2-phenylindole, dihydrochloride) staining confirmed the cells' presence and morphology on the electrospun substrates. See FIG. 14. Results indicate that the electrospun materials with the derivatized materials support HDF viability and do not indicate a cytotoxic response to surrounding HDF cells that may not be attached to the electrospun substrate.

Example 71

Biologically Active Agents Release from Sodium Hyaluronate Cross-Linked Derivatives Sodium hyaluronate (1.4 m3/kg, approx. 800 kDa) and derivatives of HA comprising mercaptobenzoic acid, thiophenol, and mercaptosuccinic acid (as disclosed in Examples 59, 60 and 61) were diluted to 4% (w/v) concentrations in deionized water and mixed with mometasone furoate (Sigma Aldrich PHR 1400-500 mg) at 0.5% (w/w) loading. The polymers were crosslinked using the addition of 2% $FeCl_3$ solution (crosslinking agent) in deionized water for 1:1 crosslinking of carboxyl groups of sodium hyaluronate and chloride of $FeCl_3$, and pH of the resulting gels was adjusted to 6.5-7.5 using 0.25M NaOH solution. The release study buffer applied to each sample consisted of 2% (w/v) sodium dodecyl sulfate (SDS) dissolved in phosphate buffered saline (pH 7.4, Sigma P3813). All samples were incubated at 37° C. and sampled for testing over 168 hours. For each timepoint, 0.5 ml of the sample was combined with 1 ml MeOH and then filtered through a 0.45 µm filter prior to analyzing using HPLC with a C18 column and 25:75 DI water:methanol as mobile phase at 1 ml/min flow rate. The chromatogram was collected using a photodiode array detector at 265 nm and the amount of mometasone furoate released was calculated from integral value of peak at the retention time of 3.3 minutes based on calibration performed previously. See Table 23 for results.

TABLE 23

| | % MF Released | | | |
|---|---|---|---|---|
| Hours | HA | MBA | Thio | MSA |
| 0 | 0 | 0 | 0 | 0 |
| 1 | 13.80 | 11.87 | 31.33 | 29.15 |
| 2 | 17.22 | 13.09 | 30.65 | 30.48 |
| 4 | 18.92 | 14.38 | 29.96 | 31.74 |
| 6 | 19.86 | 14.55 | 29.07 | 30.82 |
| 24 | 21.86 | 15.57 | 29.55 | 32.56 |
| 48 | 21.63 | 15.76 | 28.08 | 32.56 |
| 72 | 21.89 | 16.60 | 29.30 | 33.16 |
| 168 | 22.16 | 16.66 | 28.50 | 38.27 |

Example 72

Vancomycin Hydrochloride Release from Sodium Hyaluronate Cross-linked Derivatives Sodium hyaluronate (1.4 m3/kg, approx. 800 kDa) and HA derivatives comprising mercaptosuccinic acid and thiophenol, as described in Example 59 and 60 were diluted to 4% (w/v) concentrations in deionized water and mixed with vancomycin hydrochloride (Sigma Aldrich PHR1732) at 10% (w/w) loading. The polymers were crosslinked using the addition of 2% $FeCl_3$ solution (crosslinking agent) in deionized water for 1:1 linking of carboxyl groups of sodium hyaluronate and chloride of $FeCl_3$ and pH of the gels was adjusted to 6.5-7.5 using 0.25M NaOH solution. The release study buffer applied to each sample consisted of phosphate buffered saline (pH 7.4, Sigma P3813). All samples were incubated at 37° C. and sampled for testing over 24 hours. For each timepoint, 0.25 ml of the sample was combined with 5 ml $H_2O$ and then filtered through a 0.45 µm filter prior to analyzing using HPLC with a C18 column and 85:15 phosphate buffer (pH 3.0):methanol as mobile phase at 0.8 ml/min flow rate. The chromatogram was collected using a photodiode array detector at 205 nm and the amount of vancomycin hydrochloride released was calculated from integral value of peak at the retention time of 11.3 minutes based on calibration performed previously.

Summary results based on HPLC analysis are presented in Table 24.

TABLE 24

| | % Vancomycin Hydrochloride Release | | | |
|---|---|---|---|---|
| time (hours) | Vancomycin | HA | MSA | Thio |
| 0 | 0.00 | 0.00 | 0.00 | 0.00 |
| 1 | 98.03 | 32.83 | 60.20 | 75.71 |

TABLE 24-continued

| % Vancomycin Hydrochloride Release | | | | |
|---|---|---|---|---|
| time (hours) | Vancomycin | HA | MSA | Thio |
| 3 | 95.40 | 38.43 | 61.37 | 76.78 |
| 6 | 92.08 | 39.24 | 61.10 | 77.57 |
| 24 | 90.70 | 63.46 | 68.03 | 79.29 |
| 96 | 72.11 | 69.75 | 65.74 | 68.00 |

Example 73

Bupivicaine Release from Sodium Hyaluronate Cross-Linked Derivatives

Sodium hyaluronate (1.4 m3/kg, approx. 800 kDa) and HA derivatives comprising mercaptosuccinic acid and thiophenol, as described in Example 60 and 61, were diluted to 4% (w/v) concentrations in deionized water and mixed with bupivacaine hydrochloride monohydrate (Sigma Aldrich B5274). The polymers were crosslinked using the addition of 2% $FeCl_3$ solution in deionized water for 1:1 linking of carboxyl groups of sodium hyaluronate and chloride of FeCl3 and pH of the gels was adjusted to 6.5-7.5 using 0.25M NaOH solution. The release study buffer applied to each sample consisted of 2% (w/v) sodium dodecyl sulfate (SDS) dissolved in Phosphate buffered saline (pH 7.4, Sigma P3813). All samples were incubated at 37° C. and sampled for testing over 96 hours. For each timepoint, 0.25 ml of the sample was combined with 5 ml MeOH and then filtered through a 0.45 μm filter prior to analyzing using HPLC with a C18 column and 30:70 phosphate buffer (pH 5.0):methanol as mobile phase at 0.6 ml/min flow rate. The chromatogram was collected using a photodiode array detector at 205 nm and the amount of bupivacaine released was calculated from integral value of peak at the retention time of 7.1 minutes based on calibration performed previously. See Table 25.

TABLE 25

| % Bupivacaine Released | | | | |
|---|---|---|---|---|
| time (hours) | Bupivacaine | HA | MBA | Thio |
| 0 | 0.00 | 0.00 | 0.00 | 0.00 |
| 1 | 72.54 | 47.28 | 60.90 | 71.91 |
| 3 | 70.10 | 52.89 | 64.78 | 74.21 |
| 6 | 71.43 | 54.06 | 67.06 | 77.13 |
| 24 | 83.46 | 58.56 | 74.03 | 79.73 |

Example 74

Poly(lactic-co-glycolic acid) (PLGA) (Purasorb PLG1017) and polydioxanone (PDO) (Resomer X 206S) were dissolved in hexafluoro-2-propanol (HFIP) at 8-9% (w/v) concentration at approximately 50° C. Following cooling to room temperature, the solutions were loaded into syringes and connected into an alternating needle array of the two polymer solutions. This alternating array enabled the co-spinning or the PLGA and PDO as separate fibers that were intertwined with each other. A rotating drum collector was set to 140 RPM and the voltage set to 25 kV for the electrospinning process. The distance from the needle to collector was 19.5 cm. The syringe pumps were run in the range of 10 ml/hour to 20 ml/hour. After an electrospun sheet was produced, it was placed under heated vacuum (40° C.) for drying purposes.

Example 75

Poly(lactic-co-glycolic add) (PLGA) (Purasorb PLG1017) and polydioxanone (PDO) (Resomer X 206S) were dissolved in hexafluoro-2-propanol (HFIP) at 8-9% (w/v) concentration at approximately 50° C. Polyethylene Glycol (PEG) 35000 (Sigma Aldrich 81310) was dissolved in HFIP at 16% (w/v) concentration at room temperature conditions (~25° C.). Following cooling to room temperature, all solutions were loaded into syringes and connected into a sequential needle array of the three polymer solutions such that each polymer solution was electrosprayed separately but onto the same rotating drum. A rotating drum collector was set to 140 RPM and the voltage set to 25 kV for the electrospinning process. The distance from the needle to collector was 18.0 cm. The syringe pumps were run in the range of 8 ml/hour to 20 ml/hour. After an electrospun sheet was produced, it was placed under heated vacuum (40° C.) for drying purposes. The electrospun sheet had separate fibers of PLGA, PDO and PEG 35,000 within the same sheet.

Example 76

Co-spun electrospun substrates as described in Example 74 were submersed into 1%, or 0.5% HA derivative (as described in examples 56 and 61) aqueous solutions and sonicated for 30 s increments up to two (2) minutes. The samples were then dried under room temperature/room humidity conditions. The primary attributes of interest included the rate and uniformity of substrate wetting during and following sonication.

Example 77

Co-spun electrospun substrates as described in Examples 72 and 73 were coated with 2% HA or a HA derivative (as described in examples 54-57, 59-62) aqueous solutions. The solution was applied to the surface of the electrospun material and a compressive force was applied to the electrospun substrates to work the derivative solutions into the substrate. Excess HA or HA derivative solution was skimmed from the surface of the substrate. The substrates were then dried at room temperature/room humidity conditions. The primary attribute of interest was material wettability.

Example 78

HA or a HA derivative (as described in examples 59-61) was dissolved in DI water in the concentrations of 2%, 4%, 8%, or 12% (w/v). Some samples were combined with a 2% (w/v) $FeCl_3$ crosslinking solution. All samples were placed within a mold and frozen >12 hours at −80° C. and then dried/lyophilized at room temperature vacuum conditions >24 hours. Attributes of interest included mold conformity following drying and material rehydration behavior when introduced to an aqueous solution.

Example 79

HA or HA derivatives (as described in examples 59-61) were dissolved in DI water in the concentrations of 2%, 4%, 8%, or 12% (w/v). They were then combined with chitosan lactate (Heppe Medical Chitosan 43003) (1% or 2% (w/v) in DI water) at varying ratios of the mass of HA or HA derivative to the mass of chitosan lactate at ratios of 95/5, 90/10, 80/20, or 50/50. Some samples were combined with a 2% (w/v) FeCl$_3$ crosslinking solution. All samples were placed within a mold and frozen >12 hours at −80° C. and then dried/lyophilized at room temperature vacuum conditions >24 hours. Attributes of interest included mold conformity following drying and material rehydration behavior when introduced to an aqueous solution.

Example 80

HA or HA derivative solid forms (as described in examples 54 and 59) were mixed with chitosan lactate (Heppe Medical Chitosan 43003) (1% or 2% (w/v) in DI water) at varying ratios of the mass of HA or HA Derivative to the mass of chitosan lactate at ratios of 95/5, 90/10, 80/20, or 50/50. Some samples were combined with a 2% FeCl$_3$ crosslinking solution. All samples were placed within a mold and frozen >12 hours at −80° C. and then dried/lyophilized at room temperature vacuum conditions >24 hours. Attributes of interest included mold conformity following drying and material rehydration behavior when introduced to an aqueous solution.

All references disclosed herein, including patent references and non-patent references, are hereby incorporated by reference in their entirety as if each was incorporated individually.

It is to be understood that the terminology used herein is for the purpose of describing specific aspects only and is not intended to be limiting. It is further to be understood that unless specifically defined herein, the terminology used herein is to be given its traditional meaning as known in the relevant art.

Reference throughout this specification to "one aspect" or "an aspect" and variations thereof means that a particular feature, structure, or characteristic described in connection with the aspect is included in at least one aspect. Thus, the appearances of the phrases "in one aspect" or "in an aspect" in various places throughout this specification are not necessarily all referring to the same aspect. Furthermore, the particular features, structures, or characteristics may be combined in any suitable manner in one or more aspects.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an aspect that includes all of the associated items or ideas and one or more other alternative aspects that include fewer than all of the associated items or ideas.

Unless the context requires otherwise, throughout the specification and claims that follow, the word "comprise" and synonyms and variants thereof such as "have" and "include," as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed disclosure.

Any headings used within this document are only being utilized to expedite its review by the reader, and should not be construed as limiting the disclosure or claims in any manner. Thus, the headings and Abstract of the Disclosure provided herein are for convenience only and do not interpret the scope or meaning of the aspects.

Where a range of values is provided herein, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the presently described disclosure. The publications discussed above and throughout the text are provided solely for their disclosure prior to the filing date of the present application. Nothing herein is to be construed as an admission that the inventors are not entitled to antedate any referenced publication by virtue of prior disclosure.

All patents, publications, scientific articles, web sites, and other documents and materials referenced or mentioned herein are indicative of the levels of skill of those skilled in the art to which the disclosure pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

In general, in the following claims, the terms used should not be construed to limit the claims to the specific aspects disclosed in the specification and the claims, but should be construed to include all possible aspects along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

Other nonlimiting aspects are within the following claims. The patent may not be interpreted to be limited to the specific examples or nonlimiting aspects or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A coating for a medical device, comprising, a hyaluronic acid polymer derivative comprising one or more modified hydroxyl groups, wherein the hyaluronic acid polymer derivative has the formula:
A) HA-(OCH$_2$CH$_2$SO$_2$CH$_2$CH$_2$—X—R$^1$—Y)$_n$, where HA is hyaluronic acid, X is S or NH, R$^1$ is an aromatic moiety, and Y is one or more of H, a carboxylic acid group or a salt or ester thereof, a hydroxyl group, a sulfonic acid group or a salt thereof, or an amine group, and n is the number of modified hydroxyl groups where n≥1; or
B) (Y—R$^2$—X—CH$_2$CH$_2$SO$_2$CH$_2$CH$_2$O)$_m$-HA-(OCH$_2$CH$_2$SO$_2$CH$_2$CH$_2$—X—R$^1$—Y)$_n$, where HA is hyaluronic acid, X is S or NH, R$^1$ and R$^2$ are each a substituted or unsubstituted C$_1$-C$_{20}$ aliphatic or aromatic moiety, wherein R$^1$ and R$^2$ are different from each other, Y may be the same or different, and Y is one or more of H, a carboxylic acid group or a salt or ester thereof, a hydroxyl group, a sulfonic acid group or a salt thereof, or an amine group, and n≥1 and m≥1; or

---

SEQUENCE LISTING

```
Sequence total quantity: 6
SEQ ID NO: 1            moltype = AA  length = 24
FEATURE                 Location/Qualifiers
source                  1..24
                        mol_type = protein
                        organism = synthetic construct
SEQUENCE: 1
KIPKASSVPT ELSAISTLYL SGGC                                               24

SEQ ID NO: 2            moltype = AA  length = 4
FEATURE                 Location/Qualifiers
source                  1..4
                        mol_type = protein
                        organism = synthetic construct
SEQUENCE: 2
RGDS                                                                     4

SEQ ID NO: 3            moltype = AA  length = 5
FEATURE                 Location/Qualifiers
source                  1..5
                        mol_type = protein
                        organism = synthetic construct
SEQUENCE: 3
IKVAV                                                                    5

SEQ ID NO: 4            moltype = AA  length = 12
FEATURE                 Location/Qualifiers
source                  1..12
                        mol_type = protein
                        organism = synthetic construct
SEQUENCE: 4
GRKKRRQRRR PQ                                                            12

SEQ ID NO: 5            moltype = AA  length = 19
FEATURE                 Location/Qualifiers
source                  1..19
                        mol_type = protein
                        organism = synthetic construct
SEQUENCE: 5
CSRARKQAAS IKVAVSADR                                                     19

SEQ ID NO: 6            moltype = AA  length = 5
FEATURE                 Location/Qualifiers
source                  1..5
                        mol_type = protein
                        organism = synthetic construct
UNSURE                  4
                        note = X is any amino acid except proline
SEQUENCE: 6
VPGXG                                                                    5
```

C) $(CH_2=CH-SO_2CH_2CH_2O)_m$-HA-$(OCH_2CH_2SO_2CH_2CH_2-X-R^1-Y)_n$, where HA is hyaluronic acid, X is S or NH, $R^1$ is a substituted or unsubstituted $C_1$-$C_{20}$ aliphatic or aromatic moiety, and Y is one or more of H, a carboxylic acid group or salt or ester thereof, a hydroxyl group, a sulfonic acid group or a salt thereof, or an amine group, and $n \geq 1$ and $m \geq 1$, wherein the coating, when hydrated, increases the lubricity of a coated medical device.

2. The coating of claim 1, wherein the coating is cross-linked.

3. The coating of claim 2, wherein the coating is cross-linked with a bisepoxide.

4. A medical device comprising at least one surface and the coating of claim 1, wherein at least a portion of the at least one surface of the medical device is contacted by the coating.

5. The medical device of claim 4, wherein the medical device is a hernia or surgical mesh.

6. The medical device of claim 4 wherein the medical device is a catheter.

7. The medical device of claim 4, wherein the device or the coating or both, further comprises a biologically active agent.

8. The medical device of claim 4, wherein the device or the coating or both, further comprises a photoinitiator.

9. A medical device comprising at least one surface and the coating of claim 2, wherein at least a portion of the at least one surface of the medical device is contacted by the coating.

10. The medical device of claim 9, wherein the medical device is a hernia or surgical mesh.

11. The medical device of claim 9, wherein the medical device is a catheter.

12. The medical device of claim 9, wherein the device or the coating or both, further comprises a biologically active agent.

13. The medical device of claim 9, wherein the device or the coating or both, further comprises a photoinitiator.

14. A medical device comprising at least one surface and the coating of claim 3, wherein at least a portion of the at least one surface of the medical device is contacted by the coating.

15. The medical device of claim 14, wherein the medical device is a hernia or surgical mesh.

16. The medical device of claim 14, wherein the medical device is a catheter.

17. The medical device of claim 14, wherein the device or the coating or both, further comprises a biologically active agent.

18. The medical device of claim 14, wherein the device or the coating or both, further comprises a photoinitiator.

* * * * *